United States Patent
Chou et al.

(10) Patent No.: US 11,927,560 B2
(45) Date of Patent: *Mar. 12, 2024

(54) BIO/CHEMICAL MATERIAL EXTRACTION AND ASSAY

(71) Applicant: Essenlix Corporation, Monmouth Junction, NJ (US)

(72) Inventors: Stephen Y. Chou, Princeton, NJ (US); Wei Ding, East Windsor, NJ (US); Yufan Zhang, Monmouth Junction, NJ (US)

(73) Assignee: Essenlix Corporation, Monmouth Junction, NJ (US)

( * ) Notice: Subject to any disclaimer, the term of this patent is extended or adjusted under 35 U.S.C. 154(b) by 983 days.

This patent is subject to a terminal disclaimer.

(21) Appl. No.: 16/484,256

(22) PCT Filed: Feb. 8, 2018

(86) PCT No.: PCT/US2018/017501
§ 371 (c)(1),
(2) Date: Aug. 7, 2019

(87) PCT Pub. No.: WO2018/148469
PCT Pub. Date: Aug. 16, 2018

(65) Prior Publication Data
US 2020/0033288 A1     Jan. 30, 2020

Related U.S. Application Data

(60) Provisional application No. 62/463,578, filed on Feb. 24, 2017, provisional application No. 62/460,062, (Continued)

(51) Int. Cl.
*G01N 27/403* (2006.01)
*B01L 3/00* (2006.01)
(Continued)

(52) U.S. Cl.
CPC ...... *G01N 27/403* (2013.01); *B01L 3/502761* (2013.01); *G01N 1/2813* (2013.01);
(Continued)

(58) Field of Classification Search
CPC .... G01N 27/403; G01N 1/2813; G01N 1/286; G01N 1/38; G01N 21/8483;
(Continued)

(56) References Cited

U.S. PATENT DOCUMENTS

| 3,368,872 A | 2/1968 | Natelson |
| 3,447,863 A | 6/1969 | Patterson |

(Continued)

FOREIGN PATENT DOCUMENTS

| AU | 198813789 A | 9/1988 |
| AU | 619459 B | 1/1992 |

(Continued)

OTHER PUBLICATIONS

Van Vliet, Dillys et al., Prediction of asthma exacerbations in children by innovative exhaled inflammatory markers: Results of a longitudinal study, PLOS One, Mar. 23, 2015, vol. 10. No. 3, e0119434.

(Continued)

*Primary Examiner* — Dennis White

(57) ABSTRACT

Described are methods and devices that can accelerate the process and quantify the parameters for bio/chemical material samples. In some embodiments, a QMAX (Q: quantification; M: magnifying; A: adding reagents; X: acceleration) device having two or more electrodes capable of accelerating the electrical measurement process of the samples. In addition, the electrical measurement technology of the QMAX device enables for extraction, separation, and purification of sample components, such as but not limited to nucleic acids. In some embodiments, the QMAX device (Continued)

includes a plate for hosting a small sensing chip to facilitate a bio/chemical sensing of the sensing chip.

140 Claims, 18 Drawing Sheets

Related U.S. Application Data filed on Feb. 16, 2017, provisional application No. 62/459,232, filed on Feb. 15, 2017, provisional application No. 62/457,133, filed on Feb. 9, 2017, provisional application No. 62/456,552, filed on Feb. 8, 2017, provisional application No. 62/456,504, filed on Feb. 8, 2017.

(51) Int. Cl.
  *G01N 1/28* (2006.01)
  *G01N 1/38* (2006.01)
  *G01N 21/84* (2006.01)
  *G01N 33/49* (2006.01)
  *G01N 33/543* (2006.01)
  *G01N 35/00* (2006.01)

(52) U.S. Cl.
  CPC .............. *G01N 1/286* (2013.01); *G01N 1/38* (2013.01); *G01N 21/8483* (2013.01); *G01N 33/4905* (2013.01); *G01N 33/5438* (2013.01); *G01N 35/00* (2013.01); *B01L 2200/0668* (2013.01); *B01L 2300/0645* (2013.01); *B01L 2300/0816* (2013.01); *B01L 2300/0887* (2013.01); *B01L 2400/0415* (2013.01)

(58) Field of Classification Search
  CPC ........... G01N 33/4905; G01N 33/5438; G01N 35/00; B01L 3/502761; B01L 2200/0668; B01L 2300/0645; B01L 2300/0816; B01L 2300/0887; B01L 2400/0415
  See application file for complete search history.

(56) References Cited

U.S. PATENT DOCUMENTS

| | | | |
|---|---|---|---|
| 3,895,661 A | 7/1975 | Praglin et al. |
| 3,925,166 A | 12/1975 | Blume |
| 3,992,158 A | 11/1976 | Przybylowicz et al. |
| 4,022,521 A | 5/1977 | Hall et al. |
| 4,066,412 A | 1/1978 | Johnson et al. |
| 4,088,448 A | 5/1978 | Lilja et al. |
| 4,171,866 A | 10/1979 | Tolles |
| 4,233,029 A | 11/1980 | Columbus |
| 4,255,384 A | 3/1981 | Kitajima et al. |
| 4,258,001 A | 3/1981 | Pierce et al. |
| 4,329,054 A | 5/1982 | Bachalo |
| 4,402,614 A | 9/1983 | Porath |
| 4,427,294 A | 1/1984 | Pietro |
| 4,430,436 A | 2/1984 | Koyama et al. |
| 4,596,695 A | 6/1986 | Cottingham |
| 4,745,075 A | 5/1988 | Hadfield et al. |
| 4,806,311 A | 2/1989 | Greenquist |
| 4,883,642 A | 11/1989 | Bisconte |
| 4,906,439 A | 3/1990 | Grenner |
| 4,911,782 A | 3/1990 | Brown |
| 4,950,455 A | 8/1990 | Smith |
| 5,002,736 A | 3/1991 | Babbitt et al. |
| 5,039,487 A | 8/1991 | Smith |
| 5,096,836 A | 3/1992 | Macho et al. |
| 5,122,284 A | 6/1992 | Braynin et al. |
| 5,132,097 A | 7/1992 | Van Deusen et al. |
| 5,169,601 A | 12/1992 | Ohta et al. |
| 5,188,968 A | 2/1993 | Kano et al. |
| 5,223,219 A | 6/1993 | Subramanian et al. |
| 5,281,540 A | 1/1994 | Merkh et al. |
| 5,306,467 A | 4/1994 | Douglas-Hamilton et al. |
| 5,321,975 A | 6/1994 | Wardlaw |
| 5,362,648 A | 11/1994 | Koreyasu et al. |
| 5,413,732 A | 5/1995 | Buhl et al. |
| 5,427,959 A | 6/1995 | Nishimura et al. |
| 5,431,880 A | 7/1995 | Kramer |
| 5,591,403 A | 1/1997 | Gavin et al. |
| 5,623,415 A | 4/1997 | O'Bryan et al. |
| 5,753,456 A | 5/1998 | Naqui et al. |
| 5,768,407 A | 6/1998 | Shen et al. |
| 5,858,648 A | 1/1999 | Steel et al. |
| 5,879,628 A | 3/1999 | Ridgeway et al. |
| 5,888,834 A | 3/1999 | Ishikawa et al. |
| 5,939,326 A | 8/1999 | Chupp et al. |
| 5,948,686 A | 9/1999 | Wardlaw |
| 6,004,821 A | 12/1999 | Evine et al. |
| 6,016,367 A | 1/2000 | Benedetti et al. |
| 6,017,767 A | 1/2000 | Chandler |
| 6,022,734 A | 2/2000 | Wardlaw |
| 6,106,778 A | 8/2000 | Oku et al. |
| 6,180,314 B1 | 1/2001 | Berndt |
| 6,235,536 B1 | 5/2001 | Wardlaw |
| 6,350,613 B1 | 2/2002 | Wardlaw et al. |
| 6,358,475 B1 | 3/2002 | Berndt |
| 6,429,027 B1 | 8/2002 | Chee et al. |
| 6,503,760 B2 | 1/2003 | Malmqvist et al. |
| 6,551,554 B1 | 4/2003 | Vermeiden et al. |
| 6,623,701 B1 | 9/2003 | Eichele et al. |
| 6,632,652 B1 | 10/2003 | Austin et al. |
| 6,714,287 B2 | 3/2004 | Berndt |
| 6,723,290 B1 | 4/2004 | Wardlaw |
| 6,844,201 B2 | 1/2005 | Malmqvist et al. |
| 6,866,823 B2 | 3/2005 | Wardlaw |
| 6,869,570 B2 | 3/2005 | Wardlaw |
| 6,893,850 B2 | 5/2005 | Ostuni et al. |
| 6,921,514 B1 | 7/2005 | Vetter et al. |
| 6,929,953 B1 | 8/2005 | Wardlaw |
| 6,939,032 B2 | 9/2005 | Cosby et al. |
| 7,101,341 B2 | 9/2006 | Tsukashima et al. |
| 7,179,423 B2 | 2/2007 | Bohm et al. |
| 7,282,367 B2 | 10/2007 | Kawamura |
| 7,393,658 B2 | 7/2008 | Carbonell et al. |
| 7,410,617 B2 | 8/2008 | Sakamoto |
| 7,410,807 B2 | 8/2008 | D'Aurora |
| 7,468,160 B2 | 12/2008 | Thompson et al. |
| 7,510,841 B2 | 3/2009 | Stuelpnagel et al. |
| 7,510,848 B2 | 3/2009 | Hammond et al. |
| 7,547,424 B2 | 6/2009 | Haab et al. |
| 7,731,901 B2 | 6/2010 | Wardlaw |
| 7,738,094 B2 | 6/2010 | Goldberg |
| 7,850,916 B2 | 12/2010 | Wardlaw |
| 7,862,773 B2 | 1/2011 | Ibrahim |
| 7,863,411 B2 | 1/2011 | Hammond et al. |
| 7,897,376 B2 | 3/2011 | Porter et al. |
| 7,901,897 B2 | 3/2011 | Stuelpnagel et al. |
| 7,903,241 B2 | 3/2011 | Wardlaw et al. |
| 7,929,121 B2 | 4/2011 | Wardlaw et al. |
| 7,929,122 B2 | 4/2011 | Wardlaw et al. |
| 7,943,093 B2 | 5/2011 | Adrien et al. |
| 7,951,599 B2 | 5/2011 | Levine et al. |
| 7,995,194 B2 | 8/2011 | Wardlaw et al. |
| 8,045,165 B2 | 10/2011 | Wardlaw et al. |
| 8,058,073 B2 | 11/2011 | Chiapperi et al. |
| 8,077,296 B2 | 12/2011 | Wardlaw et al. |
| 8,081,303 B2 | 12/2011 | Levine et al. |
| 8,133,738 B2 | 3/2012 | Levine et al. |
| 8,158,434 B2 | 4/2012 | Wardlaw |
| 8,221,985 B2 | 7/2012 | Wardlaw et al. |
| 8,241,572 B2 | 8/2012 | Wardlaw |
| 8,269,954 B2 | 9/2012 | Levine et al. |
| 8,284,384 B2 | 10/2012 | Levine et al. |
| 8,287,820 B2 | 10/2012 | Williams et al. |
| 8,310,658 B2 | 11/2012 | Wardlaw et al. |
| 8,310,659 B2 | 11/2012 | Wardlaw et al. |
| 8,319,954 B2 | 11/2012 | Wardlaw et al. |
| 8,326,008 B2 | 12/2012 | Lalpuria et al. |
| 8,338,579 B2 | 12/2012 | Adams et al. |
| 8,361,799 B2 | 1/2013 | Levine et al. |

(56) References Cited

U.S. PATENT DOCUMENTS

| | | |
|---|---|---|
| 8,367,012 B2 | 2/2013 | Wardlaw |
| 8,462,332 B2 | 6/2013 | Pugia et al. |
| 8,467,063 B2 | 6/2013 | Wardlaw et al. |
| 8,472,693 B2 | 6/2013 | Davis et al. |
| 8,481,282 B2 | 7/2013 | Levine et al. |
| 8,502,963 B2 | 8/2013 | Levine et al. |
| 8,513,032 B2 | 8/2013 | Jablonski et al. |
| 8,569,076 B2 | 10/2013 | Wardlaw et al. |
| 8,594,768 B2 | 11/2013 | Phillips et al. |
| 8,604,161 B2 | 12/2013 | Hammond et al. |
| 8,628,952 B2 | 1/2014 | Stuelpnagel et al. |
| 8,633,013 B2 | 1/2014 | Kaiser et al. |
| 8,638,427 B2 | 1/2014 | Wardlaw et al. |
| 8,717,673 B2 | 5/2014 | Selvin et al. |
| 8,741,630 B2 | 6/2014 | Dickinson et al. |
| 8,750,966 B2 | 6/2014 | Phillips et al. |
| 8,778,687 B2 | 7/2014 | Levine et al. |
| 8,781,203 B2 | 7/2014 | Davis et al. |
| 8,796,186 B2 | 8/2014 | Shirazi |
| 8,797,527 B2 | 8/2014 | Hukari et al. |
| 8,835,186 B2 | 9/2014 | Jablonski et al. |
| 8,837,803 B2 | 9/2014 | Wang et al. |
| 8,842,264 B2 | 9/2014 | Wardlaw et al. |
| 8,885,154 B2 | 11/2014 | Wardlaw et al. |
| 8,906,700 B2 | 12/2014 | Lim et al. |
| 8,911,815 B2 | 12/2014 | Kram et al. |
| 8,974,732 B2 | 3/2015 | Lalpuria et al. |
| 8,994,930 B2 | 3/2015 | Evine et al. |
| 9,023,641 B2 | 5/2015 | Rodriguez et al. |
| 9,044,268 B2 | 6/2015 | Phillips et al. |
| 9,046,473 B2 | 6/2015 | Evine et al. |
| 9,084,995 B2 | 7/2015 | Wardlaw |
| 9,086,408 B2 | 7/2015 | Egan et al. |
| 9,097,640 B2 | 8/2015 | Goldberg et al. |
| 9,199,233 B2 | 12/2015 | Wardlaw |
| 9,274,094 B2 | 3/2016 | Wardlaw et al. |
| 9,291,617 B2 | 3/2016 | Levine et al. |
| 9,322,835 B2 | 4/2016 | Wardlaw |
| 9,347,962 B2 | 5/2016 | Salsman |
| 9,354,159 B2 | 5/2016 | Vaartstra |
| 9,395,365 B2 | 7/2016 | Levine et al. |
| 9,469,871 B2 | 10/2016 | Bearinger et al. |
| 9,523,670 B2 | 12/2016 | Mueller et al. |
| 9,696,252 B2 | 7/2017 | Wardlaw |
| 2001/0055882 A1 | 12/2001 | Ostuni |
| 2003/0068614 A1 | 4/2003 | Cima et al. |
| 2003/0107946 A1 | 6/2003 | Cosby et al. |
| 2003/0109059 A1 | 6/2003 | Adrien et al. |
| 2004/0131345 A1 | 7/2004 | Kylberg et al. |
| 2004/0156755 A1 | 8/2004 | Levine |
| 2004/0214310 A1 | 10/2004 | Parker et al. |
| 2004/0259162 A1 | 12/2004 | Kappel et al. |
| 2005/0000811 A1* | 1/2005 | Luka ............. B01L 3/50255 |
| | | 204/600 |
| 2005/0026161 A1 | 2/2005 | Jablonski et al. |
| 2005/0032138 A1 | 2/2005 | Lathrop et al. |
| 2005/0158880 A1 | 7/2005 | Ostuni et al. |
| 2005/0233352 A1 | 10/2005 | Zoval |
| 2005/0254995 A1 | 11/2005 | Sostek et al. |
| 2006/0015157 A1 | 1/2006 | Leong |
| 2006/0051253 A1 | 3/2006 | Gousepohl |
| 2006/0062440 A1 | 3/2006 | Hollars et al. |
| 2006/0062695 A1 | 3/2006 | Haab et al. |
| 2006/0090658 A1 | 5/2006 | Phillips |
| 2006/0160134 A1 | 7/2006 | Melker et al. |
| 2007/0087442 A1 | 4/2007 | Wardlaw |
| 2007/0243117 A1 | 10/2007 | Wardlaw |
| 2008/0028962 A1 | 2/2008 | Phillips et al. |
| 2008/0214947 A1 | 9/2008 | Hunt et al. |
| 2008/0274564 A1 | 11/2008 | D'Aurora |
| 2008/0286152 A1 | 11/2008 | Schmidt et al. |
| 2009/0211344 A1 | 8/2009 | Wang |
| 2009/0227472 A1 | 9/2009 | Stuelpnagel et al. |
| 2009/0233329 A1 | 9/2009 | Rodriguez et al. |
| 2009/0246781 A1 | 10/2009 | Klem et al. |
| 2009/0258371 A1 | 10/2009 | Wardlaw et al. |
| 2009/0298716 A1 | 12/2009 | Stuelpnagel et al. |
| 2010/0081583 A1 | 4/2010 | Shirazi |
| 2010/0085067 A1 | 4/2010 | Gabriel et al. |
| 2010/0151593 A1 | 6/2010 | D'Aurora |
| 2010/0216248 A1 | 8/2010 | Wardlaw |
| 2010/0255605 A1 | 10/2010 | Wardlaw |
| 2010/0272345 A1 | 10/2010 | Wardlaw |
| 2010/0273244 A1 | 10/2010 | Wardlaw |
| 2010/0291562 A1 | 11/2010 | Adler |
| 2011/0009297 A1 | 1/2011 | Jones et al. |
| 2011/0206557 A1 | 8/2011 | Phan et al. |
| 2011/0294198 A1 | 12/2011 | Wardlaw |
| 2012/0034647 A1 | 2/2012 | Herzog et al. |
| 2012/0107799 A1 | 5/2012 | Daum |
| 2012/0108787 A1 | 5/2012 | Lue |
| 2012/0157332 A1 | 6/2012 | Kumar et al. |
| 2012/0300293 A1 | 11/2012 | Selvin et al. |
| 2013/0008789 A1* | 1/2013 | Ronaghi et al. .......... B03C 7/02 |
| | | 204/451 |
| 2013/0065788 A1 | 3/2013 | Glezer et al. |
| 2013/0102018 A1 | 4/2013 | Schentag et al. |
| 2013/0157288 A1 | 6/2013 | Kilfeather et al. |
| 2013/0209332 A1 | 8/2013 | Wardlaw |
| 2013/0265054 A1 | 10/2013 | Lowery et al. |
| 2013/0309679 A1 | 11/2013 | Ismagilov et al. |
| 2013/0331298 A1 | 12/2013 | Rea |
| 2014/0315242 A1 | 10/2014 | Rodriguez et al. |
| 2014/0353157 A1* | 12/2014 | Hoffmeyer ........ B01L 3/502792 |
| | | 204/601 |
| 2014/0368631 A1 | 12/2014 | Wardlaw et al. |
| 2015/0036131 A1 | 2/2015 | Salsman |
| 2015/0253321 A1 | 9/2015 | Chou et al. |
| 2015/0317506 A1 | 11/2015 | Xie et al. |
| 2015/0323519 A1 | 11/2015 | Wardlaw |
| 2016/0025637 A1 | 1/2016 | Halverson et al. |
| 2016/0033496 A1 | 2/2016 | Chou et al. |
| 2016/0245797 A1 | 8/2016 | Ahmad et al. |
| 2016/0266091 A1 | 9/2016 | Levine et al. |
| 2017/0021356 A1 | 1/2017 | Dority et al. |
| 2017/0038401 A1 | 2/2017 | Holmes et al. |
| 2017/0045504 A1 | 2/2017 | Bloom |

FOREIGN PATENT DOCUMENTS

| | | | |
|---|---|---|---|
| CN | 1299466 | | 6/2001 |
| CN | 1302229 | | 7/2001 |
| CN | 1166950 | | 9/2004 |
| CN | 1188217 | | 2/2005 |
| CN | 102027369 | | 4/2011 |
| EP | 261667 | A2 | 3/1988 |
| EP | 291153 | A1 | 11/1988 |
| EP | 261667 | A3 | 5/1989 |
| EP | 291153 | B1 | 6/1992 |
| EP | 261667 | B1 | 2/1993 |
| EP | 0961110 | | 12/1999 |
| EP | 1949310 | A2 | 7/2008 |
| EP | 2290100 | | 3/2011 |
| EP | 1949310 | A4 | 11/2011 |
| EP | 2439515 | | 4/2012 |
| EP | 2554987 | | 2/2013 |
| EP | 3026433 | | 6/2016 |
| EP | 1949310 | B1 | 2/2019 |
| WO | 1991020009 | | 12/1991 |
| WO | 1999044743 | | 9/1999 |
| WO | 1999045385 | | 9/1999 |
| WO | 2001073124 | A2 | 10/2001 |
| WO | WO-0173124 | A2 * | 10/2001 ............. C12Q 1/001 |
| WO | 2003062920 | | 7/2003 |
| WO | 2005114145 | | 12/2005 |
| WO | 2005100539 | | 1/2006 |
| WO | 2007112332 | | 10/2007 |
| WO | 2009117652 | | 9/2009 |
| WO | 2009117664 | | 9/2009 |
| WO | 2009117678 | | 9/2009 |
| WO | 2009117682 | | 9/2009 |
| WO | 2009124186 | | 10/2009 |
| WO | 2009124190 | | 10/2009 |
| WO | 2009126800 | | 10/2009 |

(56) References Cited

FOREIGN PATENT DOCUMENTS

| WO | 2010115026 | 10/2010 |
| WO | 2014055559 | 4/2014 |
| WO | 2014089468 | 6/2014 |
| WO | 2014183049 | 11/2014 |
| WO | 2014205576 | 12/2014 |
| WO | 2017027643 A1 | 2/2017 |
| WO | 2017048871 | 3/2017 |

OTHER PUBLICATIONS

Written Opinion for PCT/US2018/017713 established by ISA/KR, dated Jun. 20, 2018.

* cited by examiner

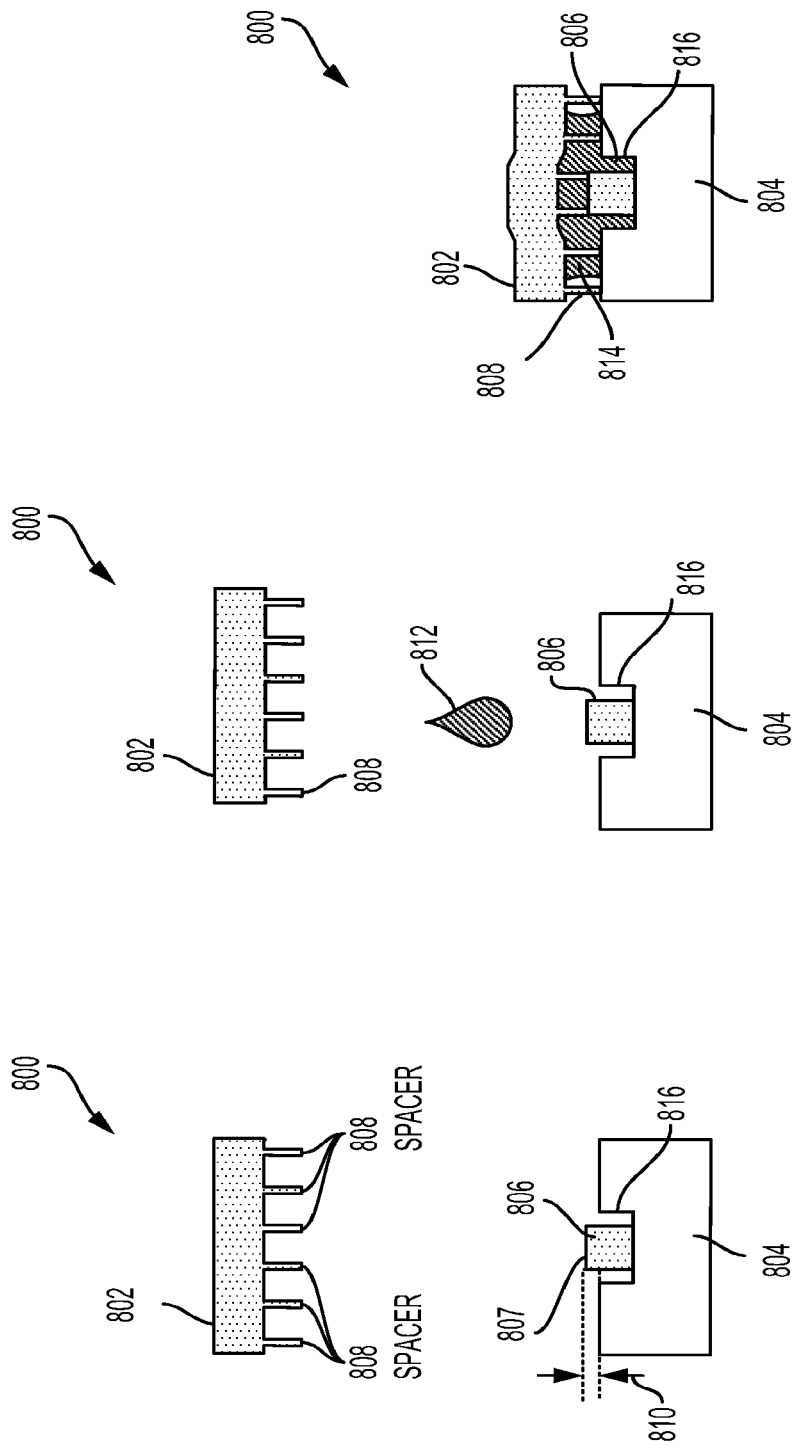

BIO/CHEMICAL MATERIAL EXTRACTION AND ASSAY

CROSS-REFERENCE TO RELATED APPLICATIONS

This application is a § 371 national stage application of International Application PCT/US2018/017501 filed on Feb. 8, 2018, which claims the benefit of priority to U.S. Provisional Application No. 62/456,552, filed on Feb. 8, 2017, U.S. Provisional Application No. 62/459,232, filed on Feb. 15, 2017, and U.S. Provisional Application No. 62/463,578, filed on Feb. 24, 2017, U.S. Provisional Application No. 62/456,504, filed on Feb. 8, 2017, U.S. Provisional Application No. 62/460,062, filed on Feb. 16, 2017, and U.S. Provisional Application No. 62/457,133, filed on Feb. 9, 2017, the contents of which are relied upon and incorporated herein by reference in their entirety. The entire disclosure of any publication or patent document mentioned herein is entirely incorporated by reference.

FIELD OF THE DISCLOSURE

This disclosure relates generally to systems and methods of performing bio/chemical material extraction and assay.

BACKGROUND OF THE DISCLOSURE

In many chemical and/or biological assays and testing (e.g. immunoassay, nucleotide assay, blood panel analysis, etc.), there are needs for methods and devices that can accelerate the process and quantify the parameters (e.g. analyte concentration, the sample volume, etc.), simplify the sample collection and measurement processes, handle samples with small volumes, perform entire assays in a short amount of time (e.g. less than a minute), allow results to be analyzed automatically (e.g. by a mobile phone), and allow non-professionals to perform the assay her/himself. The present disclosure relates to the methods, devices, and systems that uses detection of electronic signals (electrical measurement) to address these needs.

Among other things, early identification of coagulopathy has important clinical implications for managing patients who are critically ill, severely injured, or on anticoagulation therapy. Rapid and accurate assessments are essential to ensure that patients prone to blood clots—as well as those who have difficulty clotting—receive appropriate care to their conditions. Traditional tests (prothrombin time (PT) and activated partial thromboplastin time (aPTT) test) need to be conducted in a professional testing facility and require up to 10 mL blood. Consequently, a simple and portable assay that is fast, easy to use, and/or inexpensive is desirable.

Further, in biological and chemical assays (e.g. diagnostic testing), often a small chip (e.g., 3 mm×3 mm×0.5 mm, Length×Height×Thickness) is used. In many situations, it is desirable to use hands to handle a sensing chip and a fluid sample to be analyzed by the sensing chip. When a sensing chip has a dimension small compared with the fingers of hands, the sensing chip can be difficult to be handled by the hands. Furthermore, when a fluid sample is dropped on a sensing chip that is small in dimension (e.g. a few millimeters in size), the fluid sample can overflow, making a mess. Moreover, when the fluid sample is deposited on a chip, there are needs to measure the volume, change the shape, and/or detect analytes of a sample or a part of the sample, quickly and simply.

SUMMARY OF THE DISCLOSURE

As discussed above, there are needs for methods and devices that can accelerate the process and quantify the parameters for bio/chemical material samples. According to some embodiments, the present disclosure describe a QMAX (Q: quantification; M: magnifying; A: adding reagents; X: acceleration) device having two or more electrodes that accelerates the electrical measurement process. In addition, among other things, the electrical measurement technology of the current disclosure can also be used for the extraction, separation, and purification of sample components, such as but not limited to nucleic acids. For example, while traditional nucleic acid extraction assays (e.g. ethanol precipitation and phenol-chloroform extraction) in plates or tubes are complex, time-consuming, laborious and requires lab setups and significant amount of sample (typically >100 uL), extraction with the devices and methods herein discussed can overcome the shortcomings discussed above.

In some embodiments, the present disclosure describes devices, systems, and methods of a QMAX device having a plate for hosting a small sensing chip to facilitate a bio/chemical sensing of the sensing chip. The QMAX device of the present disclosure can allow easy, fast, operation of using the small chip and can enable a person to handle samples with his or her hands and without the need for additional sample volume measuring device.

In some embodiments, the exemplary embodiments disclosed herein are applicable to embodiments including but not limited to: bio/chemical assays, QMAX cards and systems, QMAX with hinges, notches, recessed edges and sliders, assays and devices with uniform sample thickness, smartphone detection systems, cloud computing designs, various detection methods, labels, capture agents and detection agents, analytes, diseases, applications, and samples; the various embodiments are disclosed, described, and/or referred to in PCT Application No. PCT/US2016/045437, which was filed on Aug. 10, 2016, PCT Application No. PCT/US2016/051775, which was filed on Sep. 14, 2016, and PCT Application No. PCT/US2016/051794, which was filed on Sep. 14, 2016, all of which are hereby incorporated by reference in their entireties and for all purposes.

BRIEF DESCRIPTION OF THE DRAWINGS

The foregoing summary, as well as the following detailed description of embodiments, is better understood when read in conjunction with the appended drawings. For the purpose of illustrating the present disclosure, the drawings show example embodiments of the disclosure; the disclosure, however, is not limited to the specific methods and instrumentalities disclosed. In the figures that present experimental data points, the lines that connect the data points are for guiding a viewing of the data only and have no other means. In the drawings:

FIGS. 8A-C illustrate a QMAX device configured to carry a sensing chip for performing bio/chemical assay of a fluid sample, according to some embodiments;

DETAILED DESCRIPTION

Described herein are computer-readable storage mediums, systems, and methods for performing bio/chemical material extraction and assay. The following detailed description illustrates some embodiments of the present disclosure by way of example and not by way of limitation. The section headings and any subtitles used herein are for organizational purposes only and are not to be construed as limiting the subject matter described in any way. The contents under a section heading and/or subtitle are not limited to the section heading and/or subtitle, but apply to the entire description of the present invention.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card does not include spacers; and the terms refer to a device that includes a first plate and a second plate that are movable relative to each other into different configurations (including an open configuration and a closed configuration), and that includes spacers (except some embodiments of the COF card) that regulate the spacing between the first and second plates. The term "X-plate" refers to one of the first and second plates in a CROF card, where the spacers are fixed to this plate. More descriptions of the COF Card, CROF Card, and X-plate are given in the provisional application Ser. No. 62/456,065, filed on Feb. 7, 2017, which is incorporated herein by reference in its entirety for all purposes.

Figure 1A:
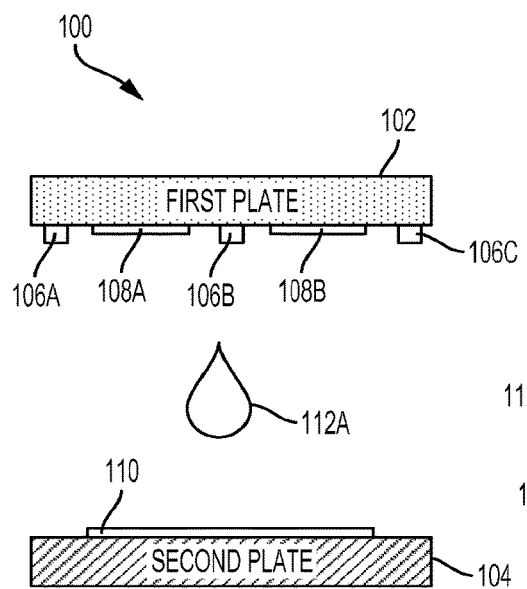
FIGS. 1A-B illustrate a QMAX (Q: quantification; M: magnifying; A: adding reagents; X: acceleration) device configured to permit bio/chemical material extraction and assay, according to some embodiments.
Figure 1B:
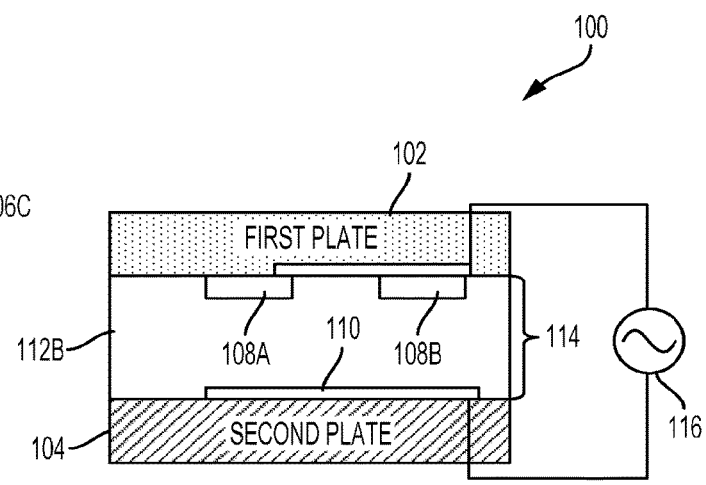

FIGS. 1A-B illustrate a QMAX (Q: quantification; M: magnifying; A: adding reagents; X: acceleration; also known as compressed regulated open flow (CROF)) device 100 configured to permit bio/chemical material extraction and assay, according to some embodiments. In some embodiments, QMAX device 100 includes first plate 102 (also referred to as "substrate" in the present disclosure), second plate 104 (also referred to as "X-plate" in the present disclosure), spacers 106A-C (also referred to as "pillars" in the present disclosure), and electrodes 108A-B and 110. In some embodiments, to enable bio/chemical material extraction and assay, first plate 102 and second plate 104 are movable relative to each other to configure QMAX device 100 into a plurality of different configurations including an open configuration, as shown in FIG. 1A, and a closed configuration, as shown in FIG. 1B.

FIG. 1A illustrates a sectional view of QMAX device 100 in the open configuration, according to some embodiments. In the open configuration, first plate 102 and second plate 104 are partially or entirely separated apart, allowing a fluid sample 112A, i.e., a bio/chemical material, to be deposited on either one or both of first plate 102 and second plate 104. In some embodiments, the surface of first plate 102 facing second plate 104 is defined as inner surface 118 of first plate 102; the surface of second plate 104 that faces first plate 102 is similarly defined as inner surface 120 of second plate 104. Each of inner surfaces 118 and 120 include a sample contact area for contacting fluid sample 112A, such as but not limited to blood. The sample contact area of each of inner surfaces 118 and 120 occupies a part of the entirety of each inner surfaces 118 and 120, respectively. In some embodiments, fluid sample 112A can be deposited on first plate 102, second plate 104, or both first plate 102 and second plate 104. In some embodiments, liquid sample 112A deposited on first plate 102 or second plate 104 has an unknown or unmeasured volume.

In some embodiments, as shown in FIG. 1A, first plate 102 can include spacers 106A-C that are fixed on inner surface 118 of first plate 102 and that allow QMAX device 100 to be configured into a closed configuration, as will be described below with respect to FIG. 1B. Alternatively, spacers 106A-C can be fixed on inner surface 120 of second plate 104. In some embodiments, spacers 106A-C can be fixed on both inner surfaces 118 and 120. In some embodiments, spacers 106A-C are fixed on one or both inner surfaces 118 and 120 by directly embossing or injection molding of first plate 102 or second plate 104. In some embodiments, spacers 106A-C can be composed of materials selected from one of polystyrene, PMMA, PC, COC, COP, or another plastic.

In some embodiments, spacers 106A-C can each have a predetermined substantially uniform height. In some embodiments, in the open configuration of FIG. 1A, the gap between first plate 102 and second plate 104 is not regulated by spacers 106A-C, which allows fluid sample 112A to be easily deposited on one or both of inner surfaces 118 and 120. In some embodiments, at least one of spacers 106A-C is positioned inside the sample contact area of one or both of inner surfaces 118 and 120. In some embodiments, all of spacers 106A-C are positioned inside the sample contact area. In some embodiments, spacers 106A-C are not fixed to either first plate 102 or second plate 104, and are instead mixed into fluid sample 112A.

In some embodiments, each of spacers 106A-C may have a pillar shape with a cross-sectional shape selected from round, polygonal, circular, square, rectangular, oval, elliptical, or a combination thereof. In some embodiments, each of spacers 106A-C may have a pillar shape with a substantially flat top surface. In some embodiments, the sidewall corners of spacers 106A-C have a round shape with a radius of curvature of at least 1 um.

In some embodiments, the ratio of the lateral dimension to height of each of spacers 106A-C is at least about 1. In some embodiments, spacers 106A-C have a density of at least 100/mm2 or at least 1000/mm2.

In some embodiments, the minimum lateral dimension of spacers 106A-C is less than or substantially equal to the minimum dimension of an analyte in fluid sample 112A. In some embodiments, the minimum lateral dimension of spacers 106A-C is between about 0.5 um-100 um or about 0.5 um-10 um.

In some embodiments, the inter-spacer distance of spacers 106A-C is substantially periodic. In some embodiments, the inter-spacer distance of spacers 106A-C is between about 5 um-200 um, about 7 um-50 um, about 50 um-120 um, or 120 um-200 um.

In some embodiments, to configure QMAX device 100 for use in bio/chemical assay and extraction, each of first plate 102 and second plate 104 can include one or more electrodes that are positioned at inner surface 118 of first plate 102 and inner surface 120 of second plate 104. In some embodiments, the electrodes are attached to inner surface 118 of first plate 102 and inner surface 120 of second plate 104. For example, as shown in FIG. 1A, electrodes 108A-B are attached to inner surface 118 of first plate 102 and electrode 110 is attached to inner surface 120 of second plate 104. In some embodiments, there is only one electrode attached to each of first plate 102 and second plate 104. In some embodiments, there are a plurality of electrodes attached to each of first plate 102 and second plate 104. In some embodiments, at least one of spacers 106A-C include the electrode, e.g., electrode 108A. In some embodiments, one or more of electrodes 108A-B and 110 are placed on the outside surface of one or both of first plate 102 or second plate 104. In some embodiments, all of electrodes 108A-B and 110 are placed on the outside surface of one or both of first plate 102 and second plate 104. In some embodiment, at least one of electrodes 108A-C is placed on the outer surface of first plate 102 and at least one of electrode 110 is placed on inner surface 120 of second plate 104, or vice versa. In some embodiments, electrodes 108A-B and 110 are made from conductive material.

In some embodiments, the conductive material can be metals such as but not limited to: gold, copper, silver, aluminum, alloys thereof, or mixtures thereof. In some embodiments, the conductive material can be conductive metallic oxide or metallic compound that is selected from the group consisting of: indium tin oxide (ITO), zinc oxide (ZnO), titanium oxide (TiOx), molybdenum dioxide (MoO2), lithium fluoride (LiF), and a combination thereof.

In some embodiments, the conductive material that make up the electrodes can be conductive small molecule and conductive polymer that is selected from poly(3,4-ethylene-dioxythiophene) poly(styrenesulfonate) (PECOT:PSS), fullerene derivatives (as C60), aluminum tris (8-hydroxy-quinoline)(Alq3), and a combination thereof.

FIG. 1B illustrates a sectional view of QMAX device 100 in the closed configuration, according to some embodiments. In some embodiments, one or more of the outer surfaces of first plate 102 and second plate 104 in the open configuration of FIG. 1A can be pressed towards each other such that inner surfaces 118 and 120 of first plate 102 and second plate 104, respectively, are pressed against each other in the closed configuration of FIG. 1B. In some embodiments, gap 114 between first plate 102 and second plate 104 are regulated by at least one spacer 106A-C (not shown in FIG. 1B).

In some embodiments, first plate 102 and second plate 104 can be pressed together after fluid sample 112A is deposited to compress at least part of fluid sample 112A into a layer of fluid sample 112B having a substantially uniform thickness and being stagnant relative to first plate 102 and second plate 104. In some embodiments, the layer of fluid sample 112B is confined by inner surfaces 118 and 120, and uniform thickness of the layer is regulated by the substantially uniform height of spacers 106A-C and the first and second plates 102 and 104. In some embodiments, the uniform thickness of layer of fluid sample 112B is the same as gap 114; in some embodiments, the thickness of layer of fluid sample 112B and gap 114 are the same as the height of spacers 106A-C. In some embodiments, layer fluid sample 112B has a uniform thickness over a lateral area that is at least 1 mm2. In some embodiments, liquid sample 112A has an unknown volume and QMAX 102 as configured in the closed configuration of FIG. 1B can compress liquid sample 112A in layer 112B having a uniform height, which may correspond to a known volume over a sample contact area.

In some embodiments, the height of spacers 106A-C is less than about 1 cm, about 200 um, 100 um, about 10 um, about 5 um, about 1 um, or about 0.1 um. In some embodiments, the height of spacers 106A-C is greater than about 0.01 um, about 0.1 um, about 1 um, about 5 um, about 10 um, about 100 um, about 200 um, or about 1 cm. In some embodiments, the height of spacers is between about 0.01 um and 1 cm such as between about 0.01 um-200 um, about 0.01 um-5 um, about 5 um-10 um, about 10 um-100 um, or about 100 um-1 cm.

As discussed above, layer of fluid sample 112B is a layer of having a substantially uniform thickness regulated by spacers 106A-C, in some embodiments. Therefore, the average thickness of the substantially uniform thickness can be the height of spacers 106A-C, as discussed above. In some embodiments, the average thickness of layer of fluid sample 112B is less than about 1 cm, about 200 um, 100 um, about 10 um, about 5 um, about 1 um, or about 0.1 um. In some embodiments, the average thickness of layer of fluid sample 112B can is greater than about 0.01 um, about 0.1 um, about 1 um, about 5 um, about 10 um, about 100 um, about 200 um, or about 1 cm. In some embodiments, the average thickness of layer of fluid sample 112B is between about 0.01 um and 1 cm such as between about 0.01 um-200 um, about 0.01 um-5 um, about 5 um-10 um, about 10 um-100 um, or about 100 um-1 cm. In some embodiments, the average thickness of the layer of uniform thickness is about equal to a minimum dimension of an analyte in fluid sample 112A.

In some embodiments, when fluid sample 112A is a blood sample (e.g., whole blood), the average thickness of layer of fluid sample 112B is about 1.8 um-3.8 um, about 1.8 um-2 um, about 2 um-2.2 um, about 2.2 um-2.6 um, or about 2.6 um-3.8 um.

As shown in FIG. 1B, in the closed configuration, electrodes 108A-B and 110 are in contact with at least part of layer of fluid sample 112B. For the sake of simplicity, first plate 102 is shown as having two electrodes 108A and 108B and second plate 104 is shown as having one electrode 110. In some embodiments, however, electrodes 108A-B can be representative of only one electrode or a plurality of electrodes (e.g., three or four electrodes or more); similarly, electrode 110 can be representative of only one electrode or a plurality of electrodes. In some embodiments, at least one of first plate 102 and second plate 104 is flexible such that one or both of first plate 102 and second plate 104 can bend slightly while compressing layer of fluid sample 112B in the closed configuration of FIG. 1B.

In some embodiments, QMAX device 100 includes a power source 116, such as but not limited to an electricity source that provides alternative current (AC) or direct current (DC). In some embodiments, power source 116 is operably connected to electrodes 108A-B and 110, which are in contact with the layer of the fluid sample 112B that is pressed into a layer of substantially uniform thickness. In some embodiments, power source 116 can provide a first electric potential at electrodes 108A-B and a second electric potential at electrode 110 to induce a voltage between electrodes 108A-B and 110 such that electrodes 108A-B and 110 are in ionic communication with layer of fluid sample 112B compressed into a layer of uniform thickness.

In some embodiments, the electrical potentials applied by power source 116 can be less than about 1000V, about 500V, about 220V, about 200V, about 150V, about 110V, about 100V, about 50V, about 10V, about 5V, about 1V, about 0.5V, about 0.2V, or about 0.1V. In some embodiments, the electrical potentials to be applied by power source 116 can be selected based on a type of electric property being measured or electrical characteristics of layer of fluid sample 112B being measured.

In some embodiments, when power source 116 provides AC, the frequency of the AC is less than about 1 GHz, about 1 MHz, about 100 kHz, about 10 kHz, about 1000 Hz, about 100 Hz, or about 10 Hz. In some embodiments, the frequency of the AC can be varied between any two of the frequencies listed above, including between 10 kHz and 1 MHz.

In some embodiments, once powered by power source 116, electrodes 108A-B and 110 are in ionic communication with layer of fluid sample 112B compressed into a layer of uniform thickness. As such, electros pass between electrodes 108A-B and electrode 110 to enable electrodes 108A-B and electrode 110 to detect one or more electric properties of fluid sample 112B to enable bio/chemical assay and extraction. For example, electrodes 108A-B and 110 can be configured to detect electric properties such as one or more of conductivity, current, potential, resistance, impedance, and capacitance as well as permittivity of fluid sample 112B in the layer of uniform thickness.

In some embodiments, the width of each of electrodes 108A-B and 110 can be at least about 2 times, about 5 times, about 10 times, about 50 times, about 100 times, about 500 time, or about 1000 times larger than the height of each of electrodes 108A-B and 110, respectively. In some embodiments, the width of each of electrodes 108A-B and 110 can be less than about 2000 times, about 1000 times, about 500 times, about 100 times, about 50 times, about 10 time, or about 5 times larger than the height of each of electrodes 108A-B and 110, respectively. In some embodiments, the width of each of electrodes 108A-B and 110 can be about 2-1000 times, about 5-500 times, or about 50-100 times larger than the height of each of electrodes 108A-B and 110, respectively.

In some embodiments, the width of each of electrodes 108A-B and 110 can be at least about 1 nm, about 10 nm, about 50 nm, about 100 nm, about 500 nm, about 1 um, about 10 um, about 50 um, about 100 um, about 500 um, about 1 mm, about 5 mm, about 10 mm, about 50 mm, or about 100 mm. In some embodiments, the width of each of electrodes 108A-B and 110 can be less than about 100 mm, about 50 mm, about 10 mm, about 5 mm, about 1 mm, about 500 um, about 50 um, about 10 um, about 1 um, about 500 nm, about 100 nm, about 50 nm, about 10 nm, or about 1 nm. In some embodiments, the width of each of electrodes 108A-B and 110 can be between about 1 nm-100 mm, about 1 nm-100 um, about 50 um-100 um, about 100 um-500 um, about 500 um-1 mm, about 1 mm-5 mm, about 5 mm-10 mm, or about 10 mm-100 mm.

In some embodiments, the height of each of electrodes 108A-B and 110 can be at least about 1 nm, about 10 nm, about 50 nm, about 100 nm, about 500 nm, about 1 um, about 10 um, about 50 um, about 100 um, about 500 um, about 1 mm, about 5 mm, or about 10 mm. In some embodiments, the height of each of electrodes 108A-B and 110 can be less than about 10 mm, about 5 mm, about 1 mm, about 500 um, about 50 um, about 10 um, about 1 um, about 500 nm, about 100 nm, about 50 nm, about 10 nm, or about 1 nm. In some embodiments, the height of each of electrodes 108A-B and 110 can be between about 1 nm-10 mm, about 1 nm-100 um, about 50 um-100 um, about 100 um-500 um, about 500 um-1 mm, or about 1 mm-5 mm.

In some embodiments, the width of each of electrodes 108A-B and 110 can be at least about 2 times, about 5 times, about 10 times, about 50 times, about 100 times, about 500 time, or about 1000 times larger than the gap between any two adjacent electrodes of electrodes 108A-B and 110, such as between electrodes 108A-B. In some embodiments, the width of each of electrodes 108A-B and 110 can be less than about 2000 times, about 1000 times, about 500 times, about 100 times, about 50 times, about 10 time, or about 5 times larger than the gap between any two adjacent electrodes of electrodes 108A-B and 110. In some embodiments, the width of each of electrodes 108A-B and 110 can be about 2-1000 times, about 5-500 times, or about 50-100 times larger than the gap between any two adjacent electrodes of electrodes 108A-B and 110.

In some embodiments, the gap between any two adjacent electrodes of electrodes 108A-B and 110 can be at least about 1 nm, about 10 nm, about 50 nm, about 100 nm, about 500 nm, about 1 um, about 10 um, about 50 um, about 100 um, about 500 um, about 1 mm, about 5 mm, about 10 mm, about 50 mm, or about 100 mm. In some embodiments, the gap between any two adjacent electrodes of electrodes 108A-B and 110 can be less than about 100 mm, about 50 mm, about 10 mm, about 5 mm, about 1 mm, about 500 um, about 50 um, about 10 um, about 1 um, about 500 nm, about 100 nm, about 50 nm, about 10 nm, or about 1 nm. In some embodiments, the gap between any two adjacent electrodes of electrodes 108A-B and 110 can be between about 1 nm-100 mm, about 1 nm-100 um, about 50 um-100 um, about 100 um-500 um, about 500 um-1 mm, about 1 mm-5 mm, about 5 mm-10 mm, or about 10 mm-100 mm.

In some embodiments, QMAX device 100 includes a measuring unit electrically coupled to at least one of electrodes 108A-B and 110 to measure one or more electric properties (e.g., electrical conductance or capacitance or both) being detected by electrodes 108A-B and 110. In some embodiments, the measuring unit can be an electric circuit electrically coupled to at least two of electrodes 108A-B and 110 to measure a permittivity of layer of fluid sample 112B. For example, to measure the permittivity of fluid sample 112B, the measuring unit can be configured to measure capacitance between electrodes 108A-B and electrode 110 to derive the permittivity of fluid sample 112B because capacitance is proportional to the permittivity.

In some embodiments, the measuring unit can be configured to measure the one or more electric properties of fluid sample 112B (being compressed into the uniform thickness) for a predetermined number of times at predetermined time periods. In some embodiments, the predetermined time periods include at times of two or more of about 10 s, about 30 s, about 60 s, about 2 min, about 3 min, about 5 min, about 8 min, about 10 min, about 15 min, about 20 min, about 30 min, etc., after fluid sample 112A is compressed into a layer of fluid sample 112B as shown in FIG. 1B.

In some embodiments where fluid samples 112A-B is a blood sample, QMAX device 100 can be configured to measure and assess coagulation properties of the blood sample. For example, QMAX device 100 may include a calculation unit configured to calculate one or both of a prothrombin time (PT) and an activated partial thromboplastin time (aPTT) based on the permittivity of fluid sample 112B being measured. In some embodiments, fluid sample 112A includes a blood sample such as whole blood or blood serum. In some embodiments, fluid sample is whole blood without dilution by liquid. In some embodiments, the blood sample includes added Ca2+. In some embodiments, the blood sample with added $Ca^{2+}$ and/or citrate salt or acid can be used as controls.

In some embodiments, to measure coagulation properties of the blood sample, a coagulation regulator can be added to the blood sample. For example, the blood sample may include citrate salt or acid for anti-coagulation purposes. In some embodiments, the blood sample includes added anticoagulant corn trypsin inhibitor (CTI). In some embodiments, the blood sample further includes added anticoagulant penicillins. In some embodiments, the blood sample includes added Activator cephalin. In some embodiments, the blood sample includes added Activator Tissue Factors (ATF). In some embodiments, the coagulation regulator can be pre-deposited and dried on one or both of inner surfaces 118 and 120. Such a coagulation regulator can be any of the regulators discussed above including, without limitation, peptides, proteins (e.g., Tissue Factors), or small molecules (e.g., ions, antibiotics, and other drugs). In some embodiments, to enable QMAX device 100 to more accurately measure coagulation properties of the blood sample, QMAX device 100 includes a temperature controller unit that is added outside of first plate 102 and second plate 104. The temperature controller can be configured to control the temperature during coagulation process in the range of 0° C. to 100° C., with a preferred temperature of 37° C.

In some embodiments, fluid sample 112A can be a biological sample selected from amniotic fluid, aqueous humour, vitreous humour, blood (e.g., whole blood, fractionated blood, plasma, or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, sebum, semen, sputum, sweat, synovial fluid, tears, vomit, urine or exhaled condensate.

In some embodiments, fluid sample 112A can be a biological sample, an environmental sample, a chemical sample, or a clinical sample. In some embodiments, fluid sample 112A can be bodily fluid such as blood, saliva, or urine.

In some embodiments, fluid sample 112A includes at least one analyte. In some embodiments, fluid sample 112A includes a plurality of analytes. In some embodiments, the at least one analyte can be a protein, nucleic acid, a cell, or a metabolite.

In some embodiments, the plurality of analytes are analytes selected from the group consisting of sodium (Na+), potassium (K+), calcium (Ca2+), bicarbonate (HCO3-), magnesium (Mg2+), chloride (Cl-), and hydrogen phosphate (HPO42-).9. In some embodiments, the plurality of analytes are macromolecules selected from the group consisting of carbohydrates (monosaccharides, disaccharides, and polysaccharides), glucose, and sucrose.

In some embodiments, the plurality of analytes are nucleic acid including a polymer of any length composed of nucleotides, e.g., deoxyribonucleotides or ribonucleotides, or compounds produced synthetically (e.g., PNA as described in U.S. Pat. No. 5,948,902) which can hybridize with naturally occurring nucleic acids in a sequence specific manner analogous to that of two naturally occurring nucleic acids, e.g., can participate in Watson-Crick base pairing interactions.

In some embodiments, the plurality of analytes are proteins including a polymeric form of amino acids of any length. In some embodiments, the length of amino acids can be more than about 2, about 5, about 10, about 20, about 50, about 100, about 200, about 500, about 1000, or about 2000. In some embodiments, the length of amino acids can be less than about 2000, about 1000, about 500, about 200, about 100, about 50, about 20, about 10, or about 5. In some embodiments, the length of amino acids can be between about 2 and 2000.

In some embodiments, the plurality of analytes are proteins that can include coded and non-coded amino acids, chemically or bio/chemically modified or derivatized amino acids, and polypeptides having modified peptide backbones. In some embodiments, the term protein can refer to fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

In some embodiments, the plurality of analytes are polypeptides that are post-translationally modified in a cell, e.g., glycosylated, cleaved, secreted, prenylated, carboxylated, phosphorylated, etc., and polypeptides with secondary or tertiary structure, and polypeptides that are strongly bound, e.g., covalently or non-covalently, to other moieties, e.g., other polypeptides, atoms, cofactors, etc.

In some embodiments, the plurality of analytes are cells including prokaryotes and eukaryotes, including bone cells, cartilage cells, nerve cells, epithelial cell, muscle cells, secretory cell, adipose cells, blood cells, conductive cells, connective cells, glandular cells, storage cells, supportive cells, etc.

In some embodiments, the plurality of analytes can include bacteria such as coccus, *bacillus, vibrio*, spirillum, spirochete, etc.

In some embodiments, QMAX device 100 can be configured to include a location marker included on a surface of or inside of first plate 802 or second plate 804 to provide information of the location of the location marker. For example, the location may indicate a sample area. In some embodiments, one or more of first plate 102 and second plate 104 can include a scale marker that provides information of a lateral dimension of the respective plate or fluid sample 112B. In some embodiments, the scale marker can be positioned on either an inner surface or an outer surface of the first plate 102 or the second plate 104. In some embodiments, one or more of first plate 102 and second plate 104 can include an imaging marker, on an inner surface or inside of first plate 102 or second plate 104, that can be configured to aid in imaging of fluid sample 112B, as will be further described with respect to FIGS. 8A-C. In some embodiments, one or more of spacers 106A-C functions as a location marker, a scale marker, an imaging marker, or a combination thereof. For example, spacers 106A and 106B may be placed at an inter-spacer distance to indicate scale, a location of a particular part of first plate 102 or second plate 104, and/or function as a guide post for imaging purposes.

In some embodiments, to enable first plate 102 and second plate 104 to be capable of being configured in the open configuration of FIG. 1A and the closed configuration of FIG. 1B, first plate 102 can be connected to second plate 104 to enable first plate 102 to fold over second plate 104. In some embodiments, first plate 102 and second plate 104 can be made from a single piece of material that is configured to be changed from the open configuration to the closed configuration by folding first plate 102 and second plates 104.

In some embodiments, first plate 102 and second plate 104 are connected by a hinge configured to allow folding along the hinge to configure the first plate 102 and second plate 104 in the open and closed configurations. In some embodiments, the hinge is a separate material from first plate 102 and second plate 104.

FIGS. 2-6 illustrate QMAX devices similar to QMAX device 100 of FIGS. 1A-B, but with varying placement and amount of electrodes, according to some embodiments. It should be noted, that for clarity purposes, not all the components as described with respect to FIGS. 1A-B are shown in all of FIGS. 2-6. For example, spacers 106A-C, as described with respect to FIGS. 1A-B, are not shown in FIGS. 2-6. The specific design of the QMAX devices of FIGS. 2-6 and their components can vary and the presence or absence of the certain components, such as spacers 106A-C, can be inferred from the design of the experiments and the descriptions for the specific QMAX devices.

Figure 2A:
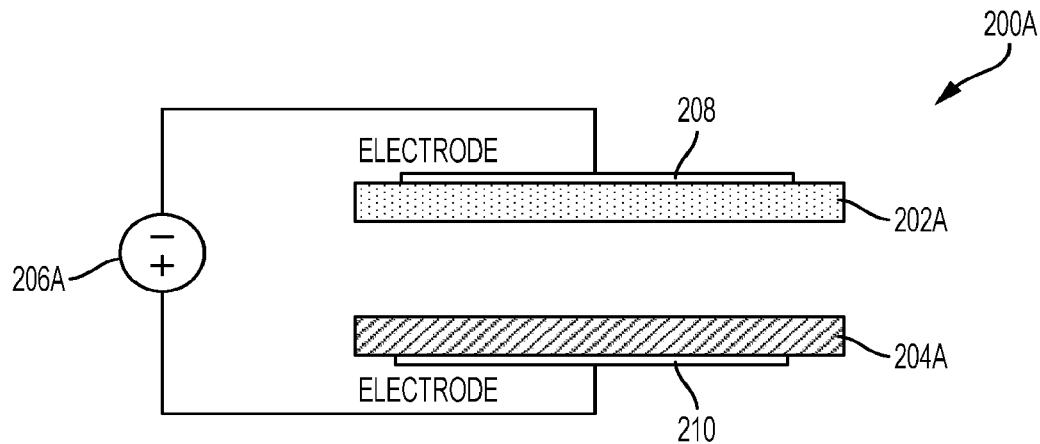
FIGS. 2A-C illustrate QMAX devices having electrodes not positioned at either of the inner surfaces of a first plate and a second plate, according to some embodiments.
Figure 2B:
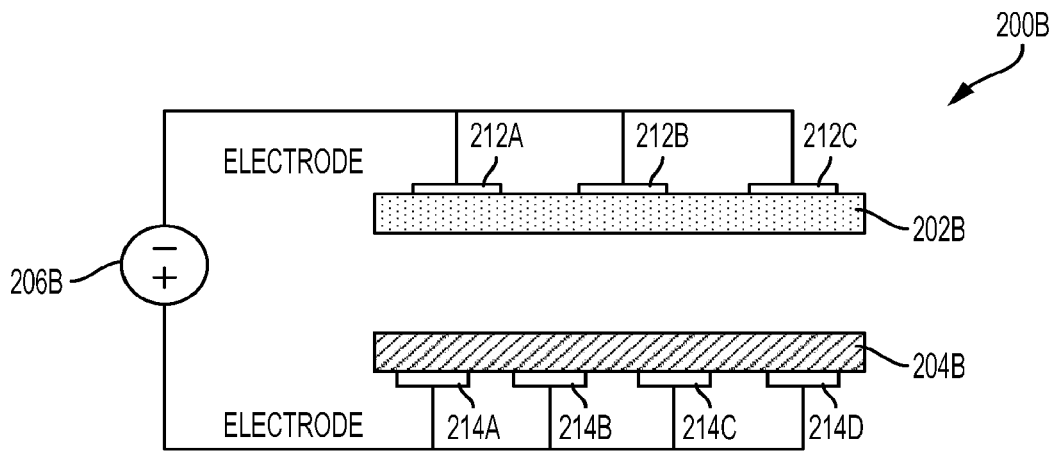
Figure 2C:
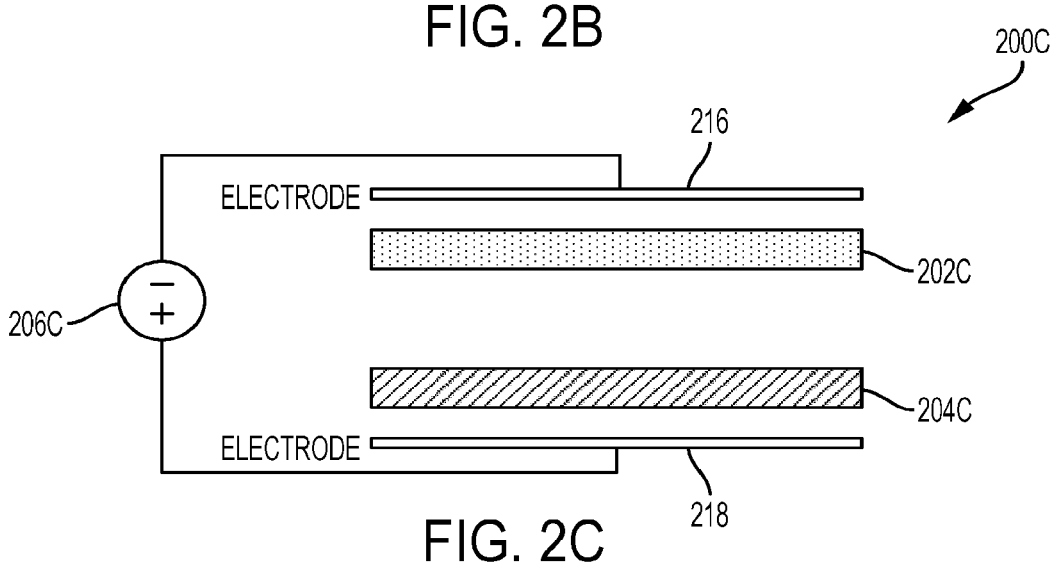

FIGS. 2A-C illustrate QMAX devices 200A-C having electrodes not positioned at either of the inner surfaces of first plate 202A-C and second plate 204A-C, according to some embodiments. Therefore, FIGS. 2A-C show QMAX devices 200A-C that are functional without current flow. In some embodiments, a power source 206A-C (e.g., a voltage source (DC or AC) or a current source (DC or AC)) applies power to at least two electrodes of each of QMAX devices 200A-C, respectively, with each electrode being outside of QMAX devices 200A-C. Here, the term "outside" refers to space outside QMAX devices 200A-C when respective first plate 202A-C and second plate 204A-C are in the closed configuration.

In FIG. 2A, QMAX device 200A includes two electrodes 208 and 210 positioned outside of and in contact with the outer surfaces of first plate 202A and second plate 204A, respectively. In FIG. 2B, QMAX device 200B includes a plurality of electrodes 212A-C and a plurality of electrodes 214A-D that are each dis-continuous (e.g. an array), outside, and in contact with the outer surfaces of first plate 202B and second plate 204B, respectively. As shown in FIGS. 2A-B, each of first plate 202A-B and second plate 204A-B can include only one electrode or a plurality of electrodes, according to some embodiments. In FIG. 2C, QMAX device 200C includes electrodes 216 and 218 that are separate, outside first plate 202C and second plate 204C, and not in contact with either of first plate 202C and second plate 204C. In some embodiments, such as that depicted in FIG. 2C, none of the electrodes of the QMAX device is in physical contact with either of the first or second plates of the QMAX device.

Figure 3A:
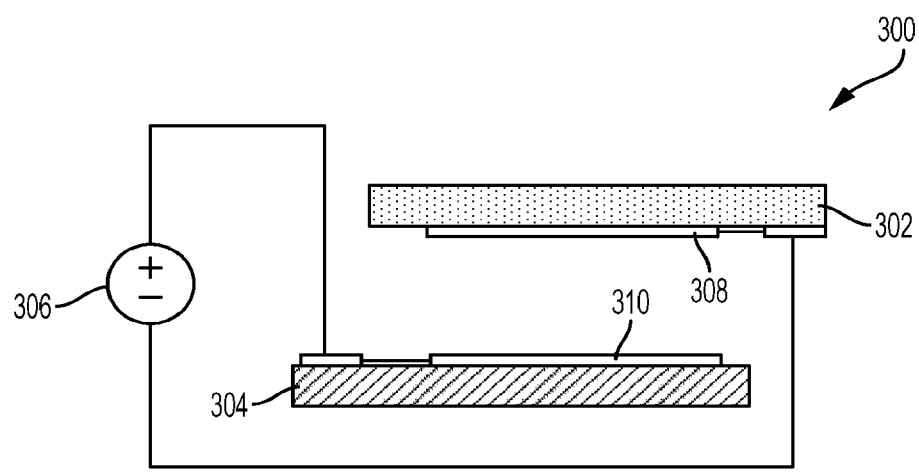
FIGS. 3A-B illustrates a QMAX device that is functional with current flow, according to some embodiments.
Figure 3B:
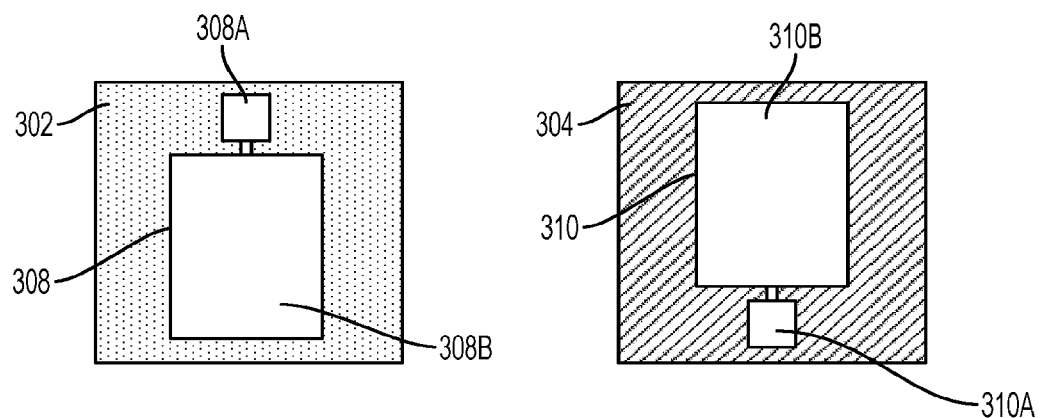

FIGS. 3A-B illustrate a QMAX device 300 that is functional with current flow, according to some embodiments. As described with respect to FIGS. 1A-B, QMAX device 300 can include similarly named components: first plate 302, second plate 304, power source 306, and electrodes 308 and 310. In some embodiments, FIG. 3A shows a sectional view of QMAX device 300 where first plate 302 has at least one electrode 308 on its inner surface and second plate 304 has at least one electrode 310 on its inner surface. In some embodiments, when power source 306 is DC, at least one of electrodes 308 and 310 connects to the anode of power source 306 and at least one of electrodes 308 and 310 connects to the cathode of power source 306.

As shown in a FIG. 3B, each of electrodes 308 and 310 have two pads: contact pad 308A and measurement pad 308B for electrode 308; and contact pad 310A and measurement pad 310B for electrode 310. In some embodiments, as shown in FIG. 3A, each of contact pads 308A and 310A are electrically connected to the outside power source 306. In some embodiments, when QMAX device 300 is configured into the closed configuration after a sample liquid is deposited, measurement pads 308B and 310B are in contact with the fluid sample. In some embodiments, the entirety of measurement pads 308B and 310B are in contact with the fluid sample. In some embodiments, only a portion of each of measurement pads 308B and 310B is in contact with the fluid sample. In some embodiments, each of electrodes 308 and 310 has only respective measurement pads 308B and 310B, each of which is directly connected to the power source 306 with wires. As described above with respect to FIGS. 1A-B, electrodes 308 and 310, (e.g., measurement pads 308B and 310B), can be configured to measure one or more electric properties of the fluid sample compressed into a layer of substantially uniform thickness once power source 306 is applied to electrodes 308 and 310 via, for example, contact pads 308A and 310A. Therefore, QMAX device 300 can be configured to perform bio/chemical material assay via electrical measurements.

Figure 4A:
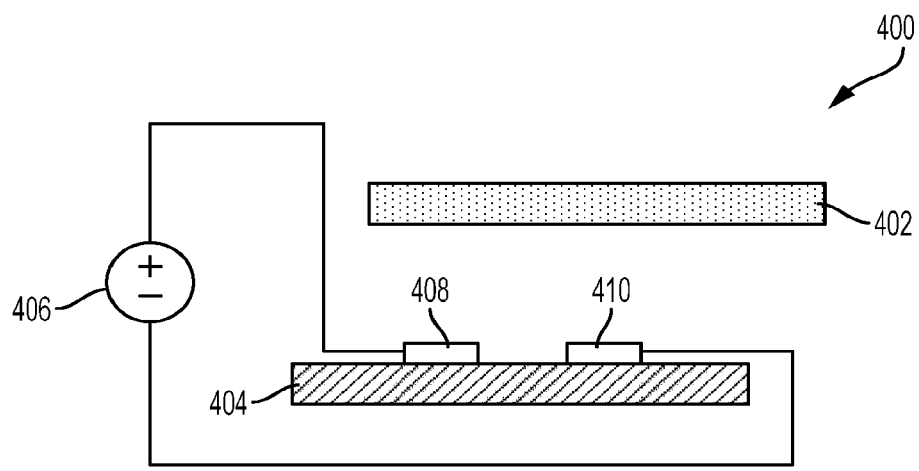
FIGS. 4A-B illustrates a QMAX device that is functional with current flow, according to some embodiments.
Figure 4B:
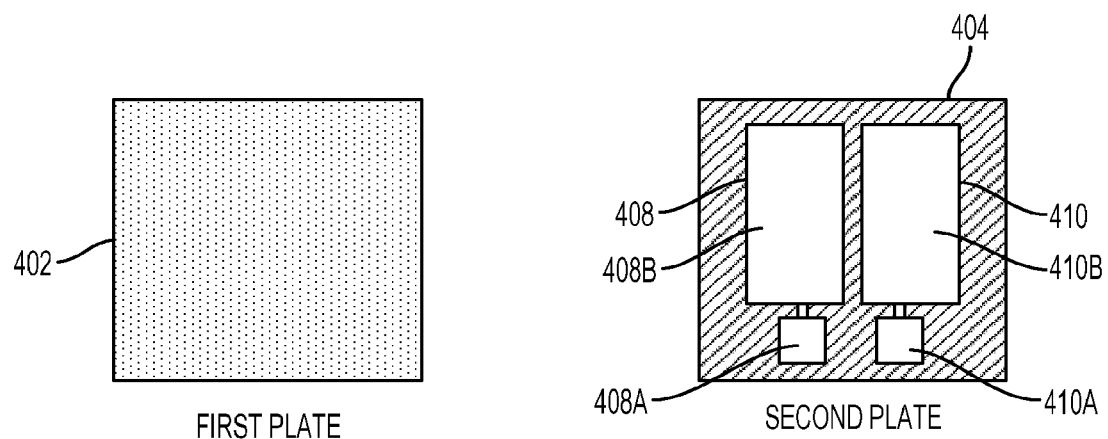

FIGS. 4A-B illustrate a QMAX device 400 that is functional with current flow, according to some embodiments. As described with respect to FIGS. 3A-B, QMAX device 400 can include similarly named components: first plate 402, second plate 404, power source 406, and electrodes 408 and 410. Further, like QMAX device 300 of FIGS. 3A-B, each of electrodes 408 and 410 can include respective contact pads 408A and 410A and respective measurement pads 408B and 410B. In some embodiments, in contrast to FIGS. 3A-B, both of electrodes 408 and 410 can be placed inside, on the inner surface, of only one of first plate 402 or second plate 404. For example, as shown in FIGS. 4A-B, both of electrodes 408 and 410 are placed on the inner surface of second plate 404. In some embodiments, all of the electrodes (e.g., electrodes 408 and 410) of QMAX device 400 are placed on only one of the first plate 402 or second plate 404.

In some embodiments, the width of each of electrodes 408 and 410 is much larger than the height of each electrode 408 and 410 and much larger than the gap between two adjacent electrodes 408 and 410. In some embodiments, the length and width of each of electrodes 408 and 410 are substantially larger than the gap between two adjacent electrodes (e.g., electrodes 408 and 410) when first plate 402 and second plate 404 are pressed together in the closed configuration of QMAX device 400. In some embodiments, the length and/or the width of each of the electrodes 408 and 410 (e.g. the measurement pads 408B and 410B) are at least about 2 times, about 5 times, about 10 times, about 20 times, about 30 times, about 40 times, about 50 times, about 75 times, about 100 times, about 150 times, about 200 times, about 300 times, about 400 times, about 600 times, about 600 times, about 700 times, about 800 times, about 900 times, about 1000 times, about 5000 times, about 10000 times, about 5000 times, about 100000 times, about 500000 times, or about 1000000 times larger than the gap between the two electrodes 408 and 410.

Figure 5A:
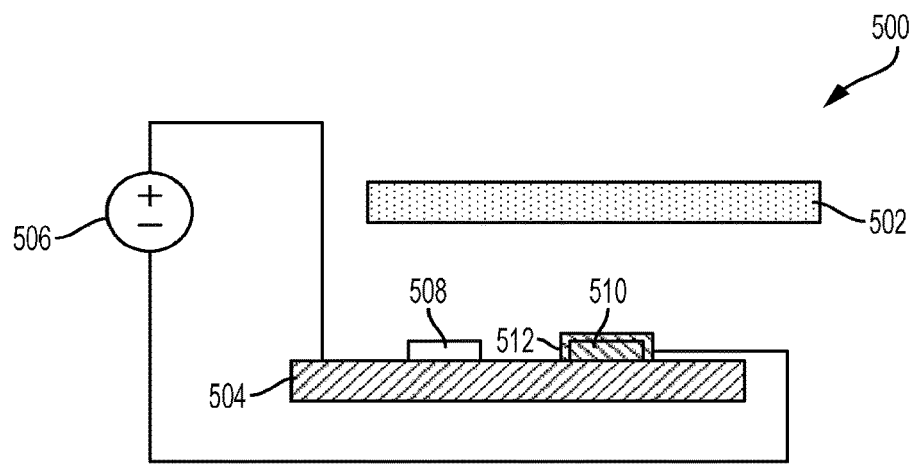
FIGS. 5A-B illustrates a QMAX device configured to measure analyte concentration in a fluid sample, according to some embodiments.
Figure 5B:
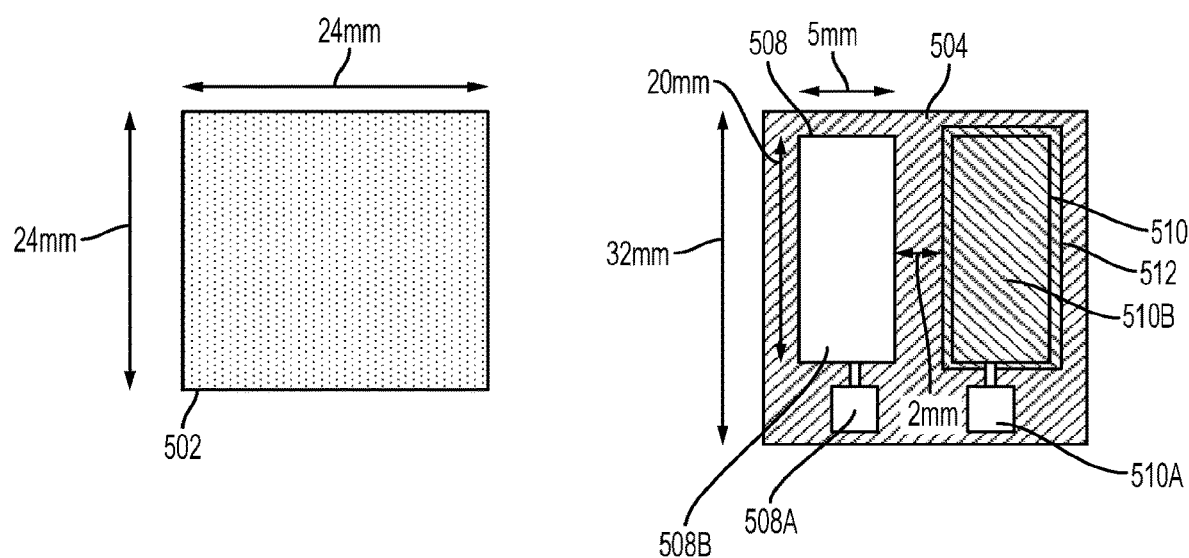

FIGS. 5A-B illustrates a QMAX device configured to measure analyte concentration of a fluid sample, according to some embodiments. As described with respect to FIGS. 4A-B, QMAX device 500 can include similarly named components: first plate 502, second plate 504, power source 506, electrode 508 (e.g., contact pad 508A and measurement pad 508B), and electrode 510 (e.g., contact pad 510A and measurement pad 510B). While the specific placement and number of electrodes 508 and 510 of QMAX device 500 are shown to be similar to the design shown in FIGS. 4A-B, the placement and number of electrodes 508-510 may instead be in one of the configurations as described or shown in any of FIG. 1A-B or 3A-B, according to some embodiments. In contrast to previously described embodiments, however, QMAX device 500 includes a barrier membrane 512 (e.g., an ion-selective membrane) that covers one of electrodes 508 or 510. For example, as shown in FIGS. 5A-B, barrier membrane 512 may cover electrode 510, specifically, measurement pad 510B of electrode 510. In some embodiments, to cover electrode 510, barrier membrane 512 can be coated on top of electrode 510. While example dimensions of first plate 502 and second plate 504 are shown in FIG. 5B, the dimensions may be adjusted according to specific design of the experiments, such as but not limited to the sample amount and the analyte within the fluid sample to be measured. In some embodiments, barrier membrane 512 has a contacting surface for contacting the fluid sample. In some embodiments, one of electrodes 508 and 510 (e.g., electrode 510) includes a perforated conductive sheet, which provides the function of a contacting surface of barrier membrane 512.

In some embodiments, as described with respect to FIGS. 1A-B, QMAX device 500 can include a measurement device to measure electric properties of the fluid sample when QMAX device 500 is in a closed configuration. For example, the measurement device can measure a current flowing through the fluid sample in a layer of substantially uniform thickness and flowing between electrodes 508 and 510. In some embodiments, barrier membrane 512 can be composed to have ion selecting effects such that the current measured by the measurement device can reflect the concentration/amount of certain analytes, such as but not limited to ions, within the fluid sample. In particular, barrier membrane 512 can be configured to permit a selected analyte in the fluid sample from passing through barrier membrane 512 to be in electrical communication with at least one electrode (e.g., electrode 510) being covered by barrier membrane 512 as a result of power source 506 supplying a power. In some embodiments, barrier membrane 512 can be configured to allow the passing through of one or more selected analytes in the fluid sample and block the passing through of one or more different selected analytes in the fluid sample.

In some embodiments, to enable the selective effects of barrier membrane 512, barrier membrane 512 can be made of insoluble, infusible synthetic organic polymer matrix which is bound with chemicals that selectively allow certain analytes in the fluid sample to pass through barrier membrane 512. In some embodiments, barrier membrane 512 can be made of organic polymer matrix selected from the group consisting of poly(vinyl chloride) (PVC), polyvinylpyrrolidone, polydimethylsiloxane, perfluoropolyether, etc. In some embodiments, the chemicals that selectively allow passage of certain analytes can be chemicals selected from ETH 157 carrier, ETh 227 carrier, ETH 2120 carrier, a bis(12-crown-4) compound, hemispherand, valinomycin, BBPA, KTpClPB, and '70 o-nitrophenyl octyl ether, etc.

In some embodiments, to measure the analyte concentrations of the fluid sample, the measurement device can measure current flowing between electrodes 508 and 510 at a plurality of different voltages applied by power source 506 between electrodes 508 and 510. In some embodiments, the measurement device can be configured to measure an electron amount and current density passing between at least two electrodes (e.g., electrodes 508 and 510) to determine an analyte concentration of the fluid sample because the electron amount and current density is correlated to the concentration of the selected analyte in the sample liquid.

In some embodiments, the measurement device can be configured to measure an electrical impedance between at least two electrodes (e.g., electrodes 508 and 510) when powered by power source 506 to determine an analyte concentration of the fluid sample. In some embodiments, the electrical impedance measured between about frequencies 10 kHz to 1 MHz is correlated to the concentration of the selected analyte in the sample liquid.

In some embodiments, the inner surface of at least one of first plate 502 and second plate 504 can be coated with chemicals, which generate electrons in communication with a selected analyte in the fluid sample when electrodes 508 and 510 are powered by power source 506. In some embodiments, the measurement device can be configured to measure an electron amount and current density passing between at least two electrodes (e.g., electrodes 508 and 510) to determine an analyte concentration of the fluid sample because the electron amount and current density (as a result of the added chemical) is correlated to the concentration of the selected analyte in the sample liquid.

In some embodiments, the measurement device can be configured to measure one or more of the current, potential, conductance, and/or capacitance of the fluid sample compressed into a layer of uniform thickness. Accordingly, including barrier membrane 512 enables QMAX device 500 to measure analyte concentrations in the fluid sample.

Figure 6:
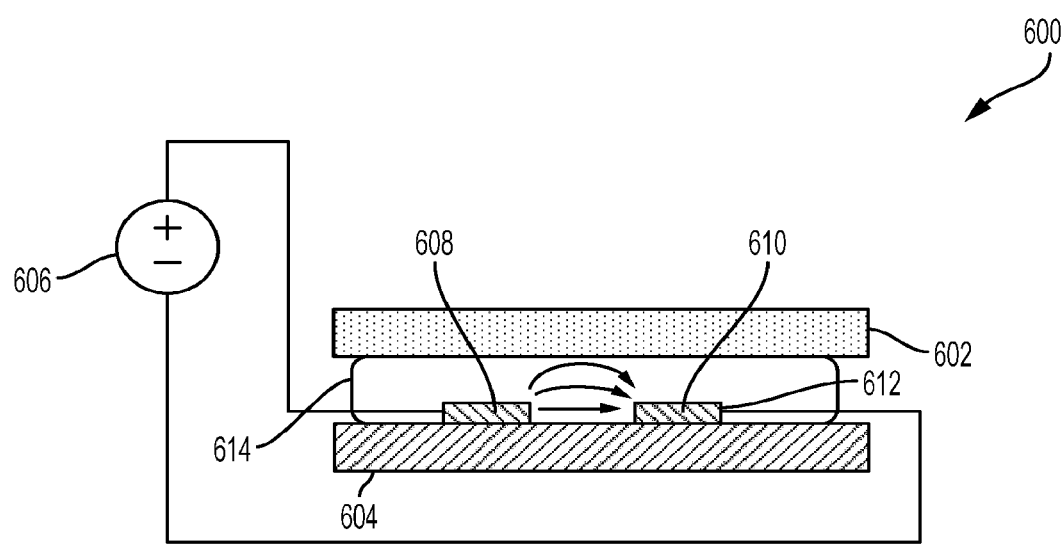
FIG. 6 illustrates a diagram showing how a QMAX device can be configured to measure analyte concentration in a fluid sample, according to some embodiments.

FIG. 6 illustrates a diagram showing how a QMAX device 600 can be configured to measure analyte concentration in a fluid sample, according to some embodiments. For ease of illustration, QMAX device 600 has similarly named and placed components as QMAX device 500 of FIGS. 5A-B: first plate 602, second plate 604, power source 606, electrode 608, electrode 610, and barrier membrane 612. In some embodiments, as described with respect to FIGS. 1A-B, a fluid sample can be deposited on, for example, the inner surface of second plate 604. Then, first plate 602 can be pressed over second plate 604 to compress the fluid sample into a layer of fluid sample 614 having a uniform thickness. In some embodiments, layer of fluid sample 614 covers both of electrodes 608 and 610. In some embodiments, the current (as shown by the arrows) flowing between and electrodes 608 and 610 can be measured at a plurality of voltages induced by power source 606 between electrodes 608 and 610. Barrier membrane 612 can be selected to enable the analyte concentration of fluid sample 614 to be measured, according to some embodiments.

FIGS. 7A-F illustrate diagrams of a QMAX device 700 configured to perform bio/chemical material 710 (e.g., nucleic acid) extraction from a fluid sample 708, according to some embodiments. In some embodiments, QMAX device 700 can be implemented as a QMAX device of any of FIG. 1A-B, 2A-C, 3A-B, or 4A-B. In some embodiments, QMAX device 700 can be as a QMAX device where first and second electrodes are positioned outside of the first and second plates, as described with respect to FIGS. 2A-C. For ease of illustration, the first and second electrodes are not depicted in FIGS. 7A-F.

Figure 7A:
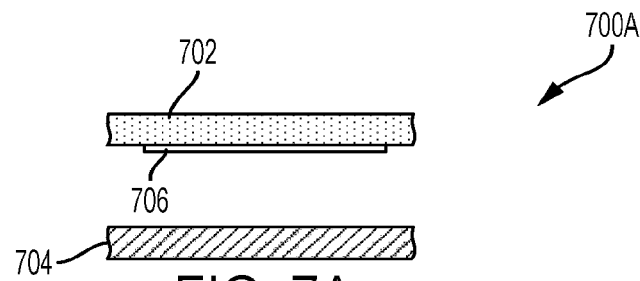
FIGS. 7A-F illustrate diagrams showing how a QMAX is configured to perform bio/chemical material extraction, according to some embodiments.

In FIG. 7A, QMAX device 700 includes first plate 702 and second plate 704 in an open configuration. In some embodiments, before bio/chemical material 710 can be extracted, fluid sample 708 needs to be lysed. In some embodiments, the lysing can be chemical, mechanical, or both. Some embodiments of such lysing have been described U.S. Provisional Application No. 62/456,528, which was filed on Feb. 8, 2017, and U.S. Provisional Application No. 62/456,596, which was filed on Feb. 8, 2017, all of which applications are incorporated herein by reference in their entireties for all purposes. In some embodiments, cell lysing reagent 706 can be attached to and dried on first plate 702 or second plate 704 to enable chemical lysing.

The term "cell lysing reagent" as used herein can include salts, detergents, enzymes, and other additives. In some embodiments, the term "salt" herein include but not limited to lithium salt (e.g. lithium chloride), sodium salt (e.g. sodium chloride), or potassium (e.g. potassium chloride) or any combination thereof. In some embodiments, the term "detergent" herein serves not only as cell lysing reagents, but also as nucleic acid binding reagents that facilitate released nucleic acids and cell-free nucleic acids to bind to the plate surface. The detergent can be any detergent, and a vast range are known and described in the literature. The detergent can be ionic, including anionic and cationic, non-ionic or zwitterionic. The term "ionic detergent" as used herein includes any detergent which is partly or wholly in ionic form when dissolved in water. Suitable anionic detergents include but are not limited to sodium dodecyl sulphate (SDS) or other alkali metal alkylsulphate salts or similar detergents, sarkosyl, or combinations thereof. In some embodiments, the detergent can be in a concentration of 0.2 to 30% (w/v), preferably 0.5 to 15%, or more preferably 1 to 10%. In some embodiments, the term "enzyme" herein includes but is not limited to lysozyme, cellulase, and proteinase. In some embodiments, the tem "additive" can include chelating agents and buffer components, including but not limited to EDTA, EGTA and other polyamino carboxylic acids, and some reducing agents, such as dithiotreitol (dTT), Tris, Bicine, Tricine, and phosphate buffers.

Figure 7B:
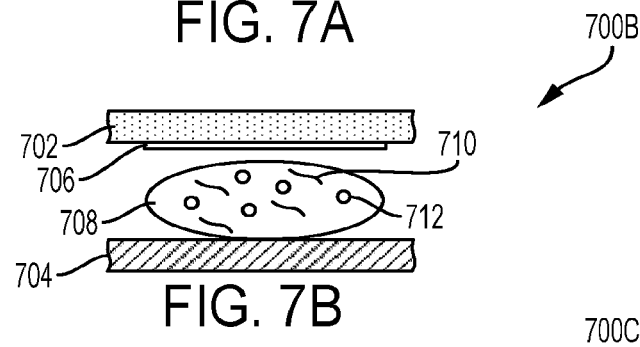

In FIG. 7B, fluid sample 708 can be deposited on either first plate 702 or second plate 704 such that fluid sample 708 comes in contact with the inner surface of first plate 702 or second plate 704. In some embodiments, fluid sample 708 can include bio/chemical material 710 (e.g., nucleic acids or cell-free nucleic acids) to be extracted and other components (e.g., cellular structures) 712.

Figure 7C:
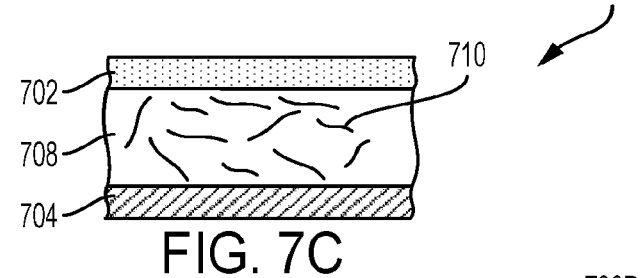

In FIG. 7C, similar to QMAX devices as described above with respect to FIGS. 1A-B, QMAX device 700 can be configured in the closed configuration by pressing first plate 702 and second plate 704 together. In some embodiments, a target component 712 (e.g., cellular structures) in fluid sample 708 can be chemically lysed by having cell lysing reagent 706 come into contact with fluid sample 708. In some embodiments, when in contact with fluid sample 708, cell lysing reagent 706 can be dissolved within fluid sample 708.

In some embodiments, when pressing first plate 702 and second plate 704 together, the spacers (not shown) on the inner surface of first plate 702 faces to the inner surface of second plate 704, and the spacers are sufficient to mechanically break target components 712 (e.g., cellular structures) in fluid sample 708 to release bio/chemical material 710. Therefore, cell lysing reagent 706 may not be used, in some embodiments.

Figure 7D:
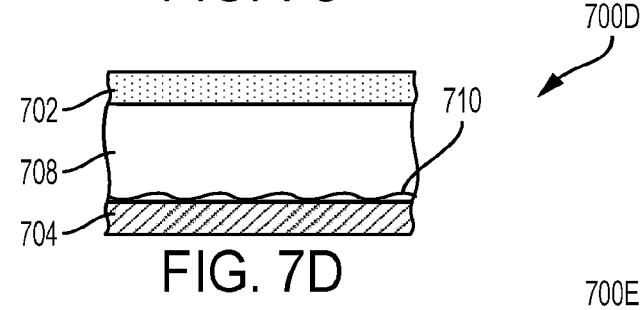

In FIG. 7D, an electric field can be applied between first plate 702 and second plate 704 via a first and a second electrode, respectively, coupled to first plate 702 and second plate 704. In some embodiments, second plate 704 can be rendered positively charged to capture the negatively charged bio/chemical material 710 on the inner surface of second plate 704. In some embodiments, once target components 712 are disrupted (i.e., lysed), the released bio/chemical material 710 can be captured nearly instantly.

In some embodiments, first plate 702 and second plate 704 can be pressed together to reduce a thickness of fluid sample 708 to 250 um or less, which greatly reduce the average diffusion time of bio/chemical material 710 from a location in fluid sample 708 to the electrically charge extraction surface of second plate 704, and hence greatly increases the extraction speed (and thus, reduces the extraction time)

In some embodiments where a power source that applies the electric field is DC, the anode of the power source connects to second plate 704 or a second electrode connected to second plate 704; and the cathode of the power source connects to first plate 702 or a first electrode connected to first plate 702.

In some embodiments, first plate 702 and second plate 704 need not be electrically charged by the power source. In some embodiments, second plate 704 can be chemically modified to exhibit electropositivity to allow binding of bio/chemical material 710 (having a negative charge) on the inner surface of second plate 704. Similarly, for bio/chemical material 710 that is positively charged, second plate 704 can be chemically modified to exhibit electronegativity to bind positively-charged bio/chemical material 710.

In some embodiments, to further enhance the ability of second plate 704 to capture bio/chemical material 710 in fluid sample 708, capture probes specific to bio/chemical material 710 to be extracted can be immobilized on the inner surface of second plate 704. In some embodiments where bio/chemical material 710 is nucleic acid, following the lysing process, bio/chemical material 710 can sequence dependently hybridize to the capture probes on the inner surface of second plate 704.

In some embodiments, "capture probe" as used herein can refer to oligonucleotides having a length between 1-200 bp, preferably between 5-50 bp, and more preferably between 10-20 bp. In some embodiments, capture probes have complementary sequence to nucleic acid sequences of interest in fluid sample 708. In some embodiments, identical capture probes can be immobilized on the inner surface of first plate 702. In some other embodiments, different capture probes having different base pair compositions are immobilized on the surface of first plate 702. In some embodiments, capture probes can be DNA, or RNA, or both, but preferably to be single strand DNA.

In some embodiments, "immobilize" as used herein refers to a process of anchoring the capture probe on the inner surface of a plate, such as second plate 704. In some embodiments, capture probes are anchored through covalent bond, where, for example, either 5' or 3' end of the capture probe is modified to facilitate coating on the inner surface of second plate 704. Commonly used 3' end modifications may include but are not limited to thiol, dithiol, amine, biotin, etc. In some other embodiments, capture probes can be passively absorbed on the inner surface of second plate 704.

In some embodiments, salts, including but not limited to sodium chloride and sodium citrate, and molecular crowding reagents, including but not limited to ficoll, dextran, or polyethylene glycol, can also be dried on the inner surface of second plate 704 to facilitate capturing nucleic acids from the sample.

Figure 7E:
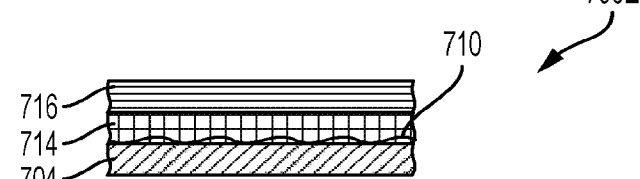

In FIG. 7E, first plate 702 can be peeled off from second plate 704 to enable the inner surface of second plate 704 to be cleaned by a sponge 716. In some embodiments, a "sponge" refers to a class of flexible porous materials that change pore sizes under different pressures. IN some embodiments, sponge 716 contains a washing reagent 714 that come in contact with the inner surface of second plate 704 to remove contaminates. In some embodiments, sponge 716 can come in contact with second plate 704 only one time, only two times, or more than two times to clean the inner surface of second plate 704 of the contaminants.

In some embodiments, "contaminate" as used herein can refer to compounds including but not limited to cell debris, proteins, non-specific nucleic acid, etc. that are detrimental to amplification reaction of bio/chemical material 710 captured in FIG. 7D.

In some embodiments, the washing is conducted by squeezing sponge 716 to release washing reagent 714 onto the inner surface of second plate 704 and releasing sponge 716 to reabsorb washing reagent 714. In some embodiments, "washing reagent" as used herein can refer to a solution that can take away contaminates without affecting the bounded bio/chemical material 710 on the inner surface of second plate 704. In some embodiments, washing reagent 714 includes low to moderate ionic strength buffers, including but not limited to 10 mM Tris-HCl or 40 mM sodium chloride.

Figure 7F:
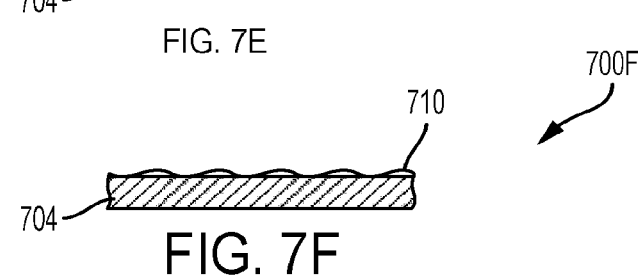

FIG. 7F shows bio/chemical material 710 captured by second plate 704 and washed of contaminants. In some embodiments, bio/chemical material 710 can be used in further biological applications, including but not limited to, nucleic acid amplification, nucleic acid hybridization and sequencing procedures.

In some embodiments, first plate 702 or second plate 704 of FIGS. 7A-F can include a storage site configured to store a reagent, which when contacting fluid sample 708, can diffuse in fluid sample 708. In some embodiments, the reagent can be cell lysing reagent 706 or washing reagent 714.

In some embodiments, sponge 716, cell lysing reagent 706, and washing reagent 714 are further described in U.S. Provisional Application No. 62/394,753, which was filed on Sep. 15, 2016, U.S. Provisional Application No. 62/456,488, which was filed on Feb. 8, 2017, and U.S. Provisional Application No. 62/456,287, which was filed on Feb. 8, 2017, all of which applications are incorporated by reference herein in their entireties for all purposes.

FIGS. 8A-C illustrate a QMAX device 800 configured to carry a sensing chip 806 for performing bio/chemical assay of a fluid sample 812, according to some embodiments. In some embodiments, QMAX device 800 includes: a first plate 802, a second plate 804, and sensing chip 806. Like QMAX device 100 as described with respect to FIGS. 1A-B, QMAX device 800 can be configured in an open configuration, as shown in FIG. 8A, and a closed configuration, as shown in FIG. 8C. In some embodiments, at least one of first plate 802 and second plate 804 is made from transparent materials. In some embodiments, like QMAX device 100 described above, first plate 802 or second plate 804 can include one or more location markers, one or more scale markers, or one or more imaging markers.

In some embodiments, first plate 802 includes a plurality of spacers 808, which may correspond to and have similar properties as spacers 106A-C as described with respect to FIGS. 1A-B. In some embodiments, spacers 808 can be positioned on only sensing chip 806 and not on the first plate 802 or second plate 804. In some embodiments, spacers 808 can be positioned on only the sample contact area of first plate 802 and not on second plate 804. In some embodiments, one or more spacers 808 can function as a location marker, a scale marker, or an imaging marker.

In some embodiments, second plate 804 includes a well 816 configured to host sensing chip 806 inside well 816. In some embodiments, sensing chip 806 can be composed of material that is dielectric, a metal, or a combination thereof. In some embodiments, sensing chip 806 can be composed of plastics.

In some embodiments, first plate 802 and second plate 804 can each have an average length, width, and thickness. In some embodiments, the thickness of first plate 802 and second plate 804 is at least about 50 nm, about 100 nm, about 200 nm, about 500 nm, about 1 um, about 2 um, about 5 um, about 10 um, about 20 um, about 30 um, about 50 um, about 70 um, about 100 um, about 120 um, about 150 um, about 200 um, about 300 um, about 400 um, about 500 um, or about 1 mm. In some embodiments, the thickness of first plate 802 and second plate 804 is less than about 3 mm, about 1 mm, about 500 um, about 400 um, about 300 um, about 200 um, about 150 um, about 120 um, about 100, about 70 um, about 50 um, about 30 um, about 20 um, about 10 um, about 5 um, about 2 um, about 1 um, about 500 um, about 200 nm, or about 100 nm. In some embodiments, the thickness of first plate 802 and second plate 804 is between about 50 nm-3 mm, about 500 nm-700 um, about 1 um-500 um, about 10 um-300 um, or about 20 um-250 um.

In some embodiments, the length or width of first plate 802 and second plate 804 is at least about 1 mm, about 3 mm, about 5 mm, about 6 mm, about 7 mm, about 8 mm, about 10 mm, about 15 mm, about 20 mm, about 30 mm, about 40 mm, about 50 mm, about 60 mm, about 70 mm, about 80 mm, about 90 mm, about 100 mm, or about 150 mm. In some embodiments, the length or width of first plate 802 and second plate 804 is less than about 200 mm, about 150 mm, about 100 mm, about 1 mm, about 500 um, about 400 um, about 300 um, about 200 um, about 150 um, about 90 um, about 80 mm, about 70 um, about 60 um, about 50 um, about 40 um, about 30 um, about 20 um, about 15 um, about 10 um, about 8 mm, about 7 mm, about 6 mm, about 5 mm, or about 3 mm. In some embodiments, the length or width of first plate 802 and second plate 804 is between about 1 mm-200 m or about 3 mm-80 mm.

In some embodiments, first plate 802 and second plate 804 can be connected by a hinge and/or have a recess notch for easy separation. In some embodiments, one plate has a dimension such that at least two of the edges are recessed from the corresponding edges of the other plate. In some embodiments, the plate with recessed edge is much thinner than the other plate. In some embodiments, the plate with recessed edge has a thickness from about 10 um-250 um, while the other plate has a thickness from about 300 um-1.5 mm.

FIG. 8A illustrates that when sensing chip 806 is hosted in well 816 of second plate 804, sensing chip has sensing surface 807 and surface offset 810. In some embodiments, sensing surface 807 is oriented and faces the same direction as the inner surface of second plate 804.

In some embodiments, surface offset 810 is the average distance between sensing surface 807 to the nearest surface of second plate 804. In some embodiments, the nearest sample contact surface of second plate 804 is the surface that is closest to sensing chip 806. If sensing surface 807 of sensing chip 806 is higher than that of the nearest surface of second plate 804, surface offset 810 may be positive, otherwise surface offset 810 may be negative.

In some embodiments, sensing surface 807 can be planar or nonplanar. In some embodiments, sensing surface 807 can be smooth or non-smooth. In some embodiments, sensing surface 807 includes a binding site that binds target analytes in fluid sample 812. In some embodiments, the binding site includes a capture agent to capture the target analytes. In some embodiments, the binding site includes an antibody or nucleic acid.

In some embodiments, sensing surface 807 has an amplification surface. In some embodiments, the amplification surface can selected from local surface plasmonic structures (e.g. D2PA), surface plasmonic surface, metallic surfaces, and a blend of metallic and dielectric layers or structures. In some embodiments, including local surface plasmonic structures (e.g. D2PA), an example amplification surface, can amplify the signals of light emitted and/or absorbed on sensing surface 807 to enable better sensing performance of sensing chip 806. In some embodiments, a capture agent can be immobilized on the amplification surface to enable sensing surface 807 to capture target analytes.

In some embodiments, surface offset 810 is substantially close to zero. In some embodiments, surface offset 810 is a positive or a negative value of at least about 10 nm, about 100 nm, about 500 nm, about 1 um, about 2 um, about 5 um, about 10 um, about 20 um, about 30 um, about 50 um, about 70 um, about 100 um, about 120 um, about 150 um, about 200 um, about 300 um, about 400 um, or about 500 um. In some embodiments, surface offset 810 is a positive or a negative value of less than about 1 mm, about 500 um, about 400 um, about 300 um, about 200 um, about 150 um, about 120 um, about 100 um, about 70 um, about 50 um, about 30 um, about 20 um, about 10 um, about 5 um, about 2 um, about 1 um, about 500 nm, about 100 nm, or about 50 nm. In some embodiments, surface offset 810 is a positive or a negative value of about 10 nm-1 mm, about 10 nm-50 um, about or about 100 nm-5 um.

In some embodiments, sensing chip 806 can have an average thickness of at least about 50 nm, about 100 nm, about 200 nm, about 500 nm, about 1 um, about 2 um, about 5 um, about 10 um, about 20 um, about 30 um, about 50 um, about 70 um, about 100 um, about 120 um, about 150 um, about 200 um, about 300 um, about 400 um, about 500 um, about 600 um, about 700 um, or about 1 mm. In some embodiments, sensing chip 806 can have an average thickness of less than about 3 mm, about 1 mm, about 700 um, about 600 um, about 500 um, about 400 um, about 300 um, about 200 um, about 150 um, about 120 um, about 100, about 70 um, about 50 um, about 30 um, about 20 um, about 10 um, about 5 um, about 2 um, about 1 um, about 500 um, about 200 nm, about 100 nm, or about 50 nm. In some embodiments, sensing chip 806 can have an average thickness of between about 50 nm-3 mm, about 500 nm-700 um, about 1 um-500 um, about 1 um-20 um, or about 20 um-100 um.

In some embodiments, sensing chip 806 can have a length or width of at least about 50 nm, about 100 nm, about 200 nm, about 500 nm, about 1 um, about 2 um, about 5 um, about 10 um, about 20 um, about 30 um, about 50 um, about 70 um, about 100 um, about 120 um, about 150 um, about 200 um, about 300 um, about 400 um, about 500 um, about 1 mm, about 3 mm, about 4 mm, about 5 mm, about 6 mm, about 7 mm, about 8 mm, about 10 mm, about 15 mm, or about 20 mm. In some embodiments, sensing chip 806 can have a length or width of less than about 30 mm, about 20 mm, about 15 mm, about 10 mm, about 8 mm, about 7 mm, about 6 mm, about 5 mm, about 4 mm, about 3 mm, about 1 mm, about 500 um, about 400 um, about 300 um, about 200 um, about 150 um, about 120 um, about 100 um, about 70 um, about 50 um, about 30 um, about 20 um, about 10 um, about 5 um, about 2 um, about 1 um, about 500 nm, about 200 nm, or about 100 nm. In some embodiments, sensing chip 806 can have a length or width of between about 50 nm-30 mm, about 1 um-10 mm, about 1 um-8 mm, about 1 um-150 um, 150 um-1 mm, or 1 mm-5 mm.

In some embodiments, well 816 has a lateral dimension: a length and a width, and a vertical dimension: a well depth. In some embodiments, the lateral dimension of well 816 is configured to be larger than the lateral dimension of sensing chip 806 such that, when sensing chip 806 is placed inside well 816, there exists a lateral distance between sensing chip 806 and well wall. In some embodiments, the well depth is configured to have a desired surface offset 810 between second plate 804 and sensing surface 807 of sensing chip 806.

Accordingly, in some embodiments, by including well 816 on QMAX 802 for hosting sensing chip 806, QMAX 802 can enable a user, e.g., a doctor or a researcher, to more easily assay liquid sample 812 and handle sensing chip 806 because QMAX 802 is much larger compared to sensing chip 806.

FIG. 8B illustrates fluid sample 812 can be deposited (e.g., dropped) between first plate 802 and second plate 804 when QMAX device 800 is configured in the open configuration, according to some embodiments. In some embodiments, in the open configuration, first plate 802 and second plate 804 are partially or completely separated apart and the average distance between the sample contact areas of first plate 802 and second plate 804 is greater than about 300 um. In some embodiments, fluid sample 812 can be deposited over sensing surface 807 of sensing chip 806. In some embodiments, second plate 804 includes an overflow barrier (e.g., a trench, a wall, or both a trench and a wall) configured to prevent fluid sample 812 from spilling out or off of second plate 804. In some embodiments, after fluid sample 812 is deposited between first plate 802 and second plate 804, first plate 802 can be placed over second plate 804 to cover fluid sample 812. In some embodiments, fluid sample 812 has a viscosity between about 0.1-4 mPa s.

FIG. 8C illustrates that first plate 802 and second plate 804 can be pressed together in the closed configuration to deform fluid sample 812 of FIG. 8B into a liquid film 814 between first plate 802 and second plate 804, according to some embodiments. In some embodiments, liquid film 814 is at least a portion of fluid sample 812 being compressed into a layer having a substantially uniform thickness. In some embodiments, in the closed configuration, the average distance between the sample contact areas of first plate 802 and second plate 804 is less than about 300 um. In some embodiments, the uniform thickness of liquid film 814 can be confined by first plate 802 and sensing surface 807, and regulated by spacers 808. In some embodiments, sensing chip 806 includes one or more spacers 808 that regulate the average spacing between the inner surface of first plate 802 and sensing surface 807 of sensing chip 806 in the closed configuration. In some embodiments, second plate 804 includes one or more spacers 808 that regulate the average spacing between the inner surface of first plate 802 and sensing surface 807 of sensing chip 806 in the closed configuration. In some embodiments, first plate 802 and second plate 804 can be pressed together using imprecision forces and/or is pressed together by hand or machine.

In some embodiments, QMAX device 800 includes a device adaptor that includes a housing, an attachment on the housing that allows the device adaptor to attached to a mobile phone with a camera, a slot in the housing that allows first plate 802 and second plate 804 in the closed configuration to slide into the slot and when the first and second plates are in the slot, an optical system in the housing is configured to have at least a part of the sample contact area be imaged by the camera.

In some embodiments, liquid film 814 has a uniform thickness sample area of at least about 5 mm2 (millimeter square), about 10 mm2, about 20 mm2, about 40 mm2, about 60 mm2, or about 80 mm2. In some embodiments, the uniform thickness sample area is less than about 150 mm2, about 80 mm2, about 60 mm2, about 40 mm2, about 20 mm2, or about 10 mm2. In some embodiments, the uniform thickness sample area is between about 5 mm2-150 mm2, about 5 mm2-10 mm2, about 10 mm2-20 mm2, about 20 mm2-40 mm2, about 40 mm2-60 mm2, about 60 mm2-80 mm2, or about 80 mm2-150 mm2.

In some embodiments, by operating QMAX 802 having first plate 802, second plate 804, and spacers 808 to compress liquid sample 812 as shown in FIG. 8C, QMAX 802 can be configured to produce a liquid film 814 of liquid sample 812 above sensing chip 806. Accordingly, the present disclosure, through the use of QMAX 808 as shown in FIGS. 8A-C, enables liquid film 814 having a thin layer of substantially uniform thickness to be generated over sensing chip 806. Further, a user, e.g., a researcher, may use QMAX 800 to more easily operate liquid sample 812 with sensing chip 806 having small dimensions, according to some embodiments.

In some embodiments, the thickness of liquid film 814 in the closed configuration is much thinner than the lateral dimension (e.g., an area) of sensing surface 807 of sensing chip 806, and the thickness is configured so that in the testing period, the saturation binding time is limited by the vertical diffusion across thickness of liquid film 814 such that the analytes that are many multiples of the thickness away from the binding sites on sensing surface 807 will have nearly no effects on the local binding.

In some embodiments, sensing surface 807 can be non-flat and first plate 802 can be configured to conform to a non-flat surface of sensing surface 807 to make the thickness of fluid sample 812 above sensing surface 807 have a substantially uniform thickness. In some embodiments, to enable sensing surface 807 to be non-flat, a flexibility of first plate 802, an inter-spacer distance of spacers 808, a geometry of spacers 808, or a combination thereof may need to be configured according to specific properties, as will be described below.

In some embodiments, to enable fluid sample 812 to be compressed into liquid film 814 having a uniform thickness, first plate 802 can be made from flexible material capable of bending 816. In some embodiments, first plate 802 can be composed of a flexible polymer such as one of polystyrene, PMMA, PC, COC, COP, or another plastic. In some embodiments, first plate 802 can be made from a flexible material having a thickness between about 10 um-200 um.

In some embodiments, QMAX device 800 can include first plate 802 being made from a flexible material such that QMAX device 800 has the property that a fourth power of the inter-spacer-distance (IDS) divided by the thickness (h) and the Young's modulus (E) of flexible first plate 802 (ISD$^4$/(hE)) is less than about $5 \times 10^6$ um$^3$/GPa, about $1 \times 10^6$ um$^3$/GPa, about $5 \times 10^5$ um$^3$/GPa, about $1 \times 10^5$ um$^3$/GPa, or about $1 \times 10^4$ um$^3$/GPa. In some embodiments, QMAX device 800 has the property that a fourth power of the inter-spacer-distance (IDS) divided by the thickness (h) and the Young's modulus (E) of the flexible plate (ISD$^4$/(hE)) is at least about $0.5 \times 10^4$ um$^3$/GPa, about $1 \times 10^5$ um$^3$/GPa, about $5 \times 10^5$ um$^3$/GPa, or about $1 \times 10^6$ um$^3$/GPa. In some embodiments, first plate 802 or second plate 804 each have a thickness in the range of 20 um to 250 um and Young's modulus of the plates in the range 0.1 to 5 GPa. In some embodiments, first plate 802 or second plate 804 have the property such that each a thickness of the flexible plate times the Young's modulus of the flexible plate is in the range 60 to 750 GPa-um.

In some embodiments, QMAX device 800 can include first plate 802 being made from a flexible material such that QMAX device 800 has the property that the thickness (h) times the Young's modulus (E) of flexible first plate 802 is in the range of about 60-750 GPa-um.

In some embodiments, a filling factor of spacers 808 can be defined as the ratio of the area of spacers 808 in contact with the layer of liquid film 814 (i.e., fluid sample 812 compressed into a layer of substantially uniform thickness) to the total plate area in contact with liquid film 814. In some embodiments, the total plate area includes the area of first plate 802 in contact with liquid film 814. In some embodiments, the total plate area includes the area of first plate 802 and second plate 804 in contact with liquid film 814.

In some embodiments, spacers 808 that regulate the uniform thickness of liquid film 814 have the property such that the Young's modulus of spacers 808 multiplied by the filling factor of spacers 808 is at least about 2 MPa, about 4 MPa, about 5 MPa, about 8 MPa, or about 10 MPa. In some embodiments, spacers 808 have the property such that the Young's modulus of spacers 808 multiplied by the filling factor of spacers 808 is less than about 15 MPa, about 10 MPa, about 8 MPa, about 5 MPa, or about 4 MPa.

In some embodiments, spacers 808 have a height that is between about 1.8 um-4 um, about 1.8 um-3.6 um, about 1.8 um-2.2 um, about 2 um-2.5 um, or about 2 um-3 um. In some embodiments, the height of spacers 808 is about 2 um, about 2.2 um, about 2.4 um, about 2.6 um, about 2.8 um, about 3 um, about 3.2 um, about 3.4 um, or about 3.6 um.

In some embodiments, the inter-spacer distance of spacers 808 is at least about two times larger than the size of an analyte in liquid film 814 where the size of the analyte is less than about 200 um.

In some embodiments, a ratio of the inter-spacer-distance to the spacer width of spacers 808 is at least about 1.5. In some embodiments, a ratio of the width to the height of spacers 808 is at least about 1, about 1.5, about 2, about 3, about 5, about 10, about 20, about 30, or about 50. In some embodiments, a ratio of the width to the height of spacers 808 is less than about 100, about 50, about 30, about 20, about 10, about 5, about 3, about 2, or about 1.5.

In some embodiments, spacers 808 are configured such that the filling factor of spacers 808 is at least about 1%, about 5%, about 10%, about 20%, about 30%, about 40%, about 50%, about 60%, or about 70%. In some embodiments, spacers 808 are configured such that the filling factor of spacers 808 is less than about 80%, about 70%, about 60%, about 50%, about 40%, about 30%, about 20%, about 10%, or about 5%. In some embodiments, spacers 808 are configured such that the filling factor of spacers 808 is between about 1%-80%, about 1%-5%, about 5%-50%, about 5%-10%, about 10%-20%, about 20%-30%, or about 50%-80%.

In some embodiments, spacers 808 are configured such that the filling factor of spacers 808 multiplied by the Young's modulus of spacers 808 is at least about 2 MPa, about 10 MPa, about 20 MPa, about 40 MPa, about 80 MPa, or about 120 MPa. In some embodiments, spacers 808 are configured such that the filling factor of spacers 808 multiplied by the Young's modulus of spacers 808 is less than about 150 MPa, about 120 MPa, about 80 MPa, about 40 MPa, about 20 MPa, or about 10 MPa. In some embodiments, spacers 808 are configured such that the filling factor of spacers 808 multiplied by the Young's modulus of spacers 808 is between about 2 MPa-150 MPa, about 2 MPa-10 MPa, about 10 MPa-20 MPa, about 20 MPa-40 MPa, about 40 MPa-80 MPa, about 80 MPa-120 MPa, or about 120 MPa-150 MPa.

In some embodiments, when a pressure is applied to first plate 802 in FIG. 8C, first plate 802 is flexible and spacers 808 are compressible. In other embodiments, first plate 802 is not flexible and spacers 808 are compressible. In further embodiments, first plate 802 is flexible and spacers 808 are not compressible.

In some embodiments, QMAX device 800 can include a first well for hosting a first sensing chip and a second well for hosting a second sensing chip. In these embodiments, the first sensing chip and the second sensing chip can have different dimensions. Further, in some embodiments, the first sensing chip can include a first reagent on its sensing surface and the second sensing chip can include a second reagent on its sensing surface. By doing so, QMAX device 800 can be configured to measure a two different characteristics of fluid sample 812.

Figure 9A:
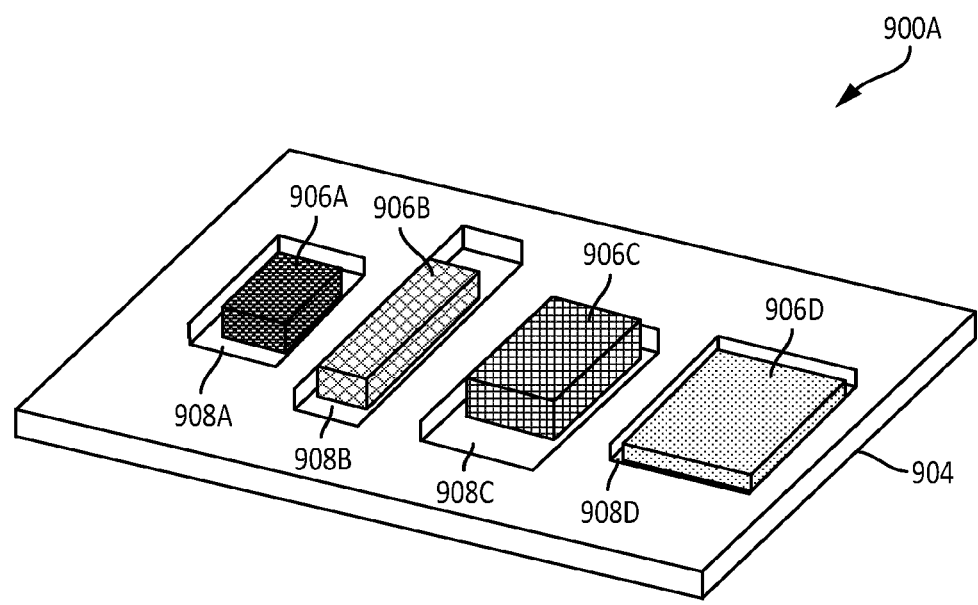
FIGS. 9A-C illustrate various perspectives of a QMAX device including a plate having a plurality of wells for hosting a corresponding plurality of sensing chips, according to some embodiments.
Figure 9B:
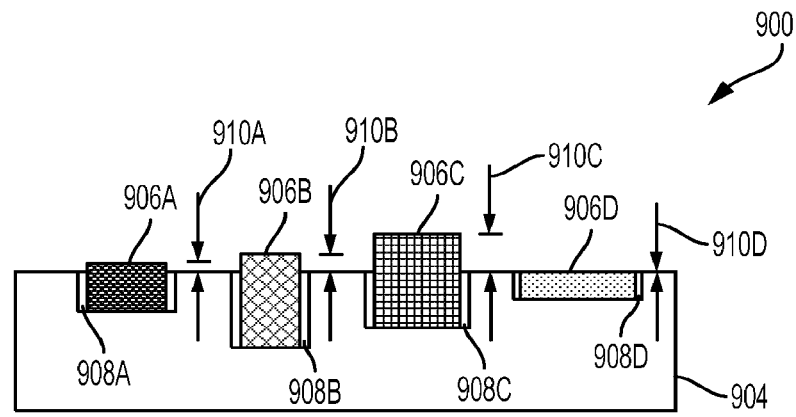
Figure 9C:
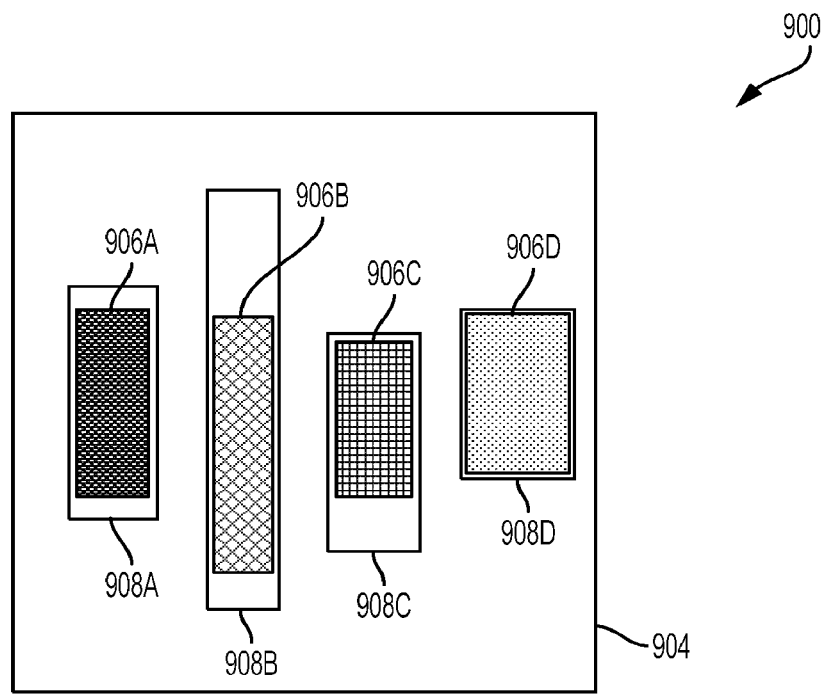

FIGS. 9A-C illustrate various perspectives of a QMAX device 900 including a plate 904 having a plurality of wells 908A-D for hosting a corresponding plurality of sensing chips 906A-D, according to some embodiments. In some embodiments, plate 904 may correspond to second plate 804 of FIGS. 8A-C. In some embodiments, two or more of sensing chips 906A-D may have different dimensions. Similarly, two or more of wells 908A-D may have different dimensions. In some embodiments, as depicted in FIG. 9B, each of sensing chips 906A-D may have corresponding surface offsets 910A-910D that may differ.

Figure 15:
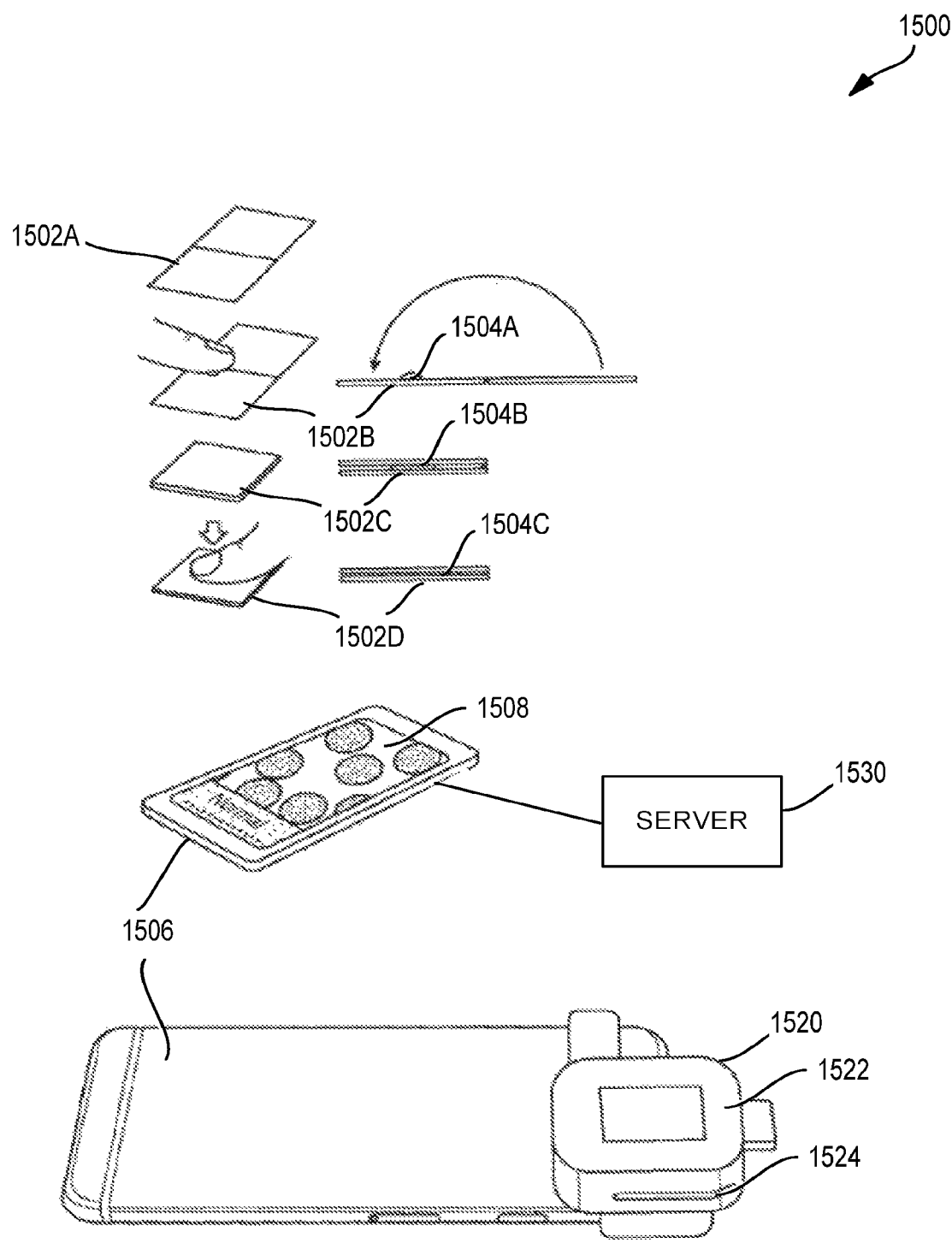
FIG. 15 illustrates a system for analyzing a fluid sample using a computing device, according to some embodiments.

FIG. 15 illustrates a system 1500 for analyzing a fluid sample 1504A-C using a computing device 1506, according to some embodiments. In some embodiments, system 1500 includes a QMAX device 1502A-D at various stages of interaction with fluid sample 1504A-C. In some embodiments, QMAX device 1502A-E may be any of the QMAX devices discussed above with respect to FIGS. 1-9.

In some embodiments, QMAX device 1502A-D includes a first plate and a second movable relative to each other to enter an open configuration (e.g., as shown by QMAX device 1502A-B) and a closed configuration (e.g., as shown by QMAX device 1502C-D). In some embodiments, QMAX device 1502A can be foldable. In some embodiments, the fluid sample 1504A can be deposited on the first plate or the second plate of QMAX device 1502B. As shown, fluid sample 1504A being deposited may be a blood sample from a pricked finger of a human. In some embodiments, the first and second plates can be pressed together into the closed configuration of QMAX device 1502C. In this closed configuration, fluid sample 1504A can start to become deformed or compressed as shown by fluid sample 1504B. In some embodiments, a pressing force can be exerted on the first plate or the second plate of QMAX device 1502D to compress fluid sample 1504B into fluid sample 1504C having a layer of substantially uniform thickness.

In some embodiments, QMAX device 1502D can be configured to sense a target bio/chemical material of fluid sample 1504C at the layer of substantially uniform thickness. For example, QMAX device 1502D may include an electrode configured to extract the bio/chemical material having an opposite polarity charge as the electrode, as discussed above with respect to FIG. 7. In other embodiments, the second plate of QMAX device 1502D may include a well for hosting a sensing chip configured to detect or bind to specific bio/chemical material, as discussed above with respect to FIGS. 8A-C and 14. In some embodiments, the first or second plate of QMAX device 1502D includes a binding site that binds a specific analyte or bio/chemical material where at least a part of fluid sample 1504C at the uniform thickness is over the binding site and is substantially less than the average lateral linear dimension of the binding site.

In some embodiments, system 1500 includes computing device 1506 configured to analyze fluid sample 1504C at the substantially uniform thickness. In some embodiments, computing device 1506 can be a mobile communication device such as a smartphone, a tablet, a smartwatch, among other portable devices.

In some embodiments, computing device 1506 includes a camera for capturing an image of a portion of fluid sample 1504C as compressed by QMAX device 1502D. In some embodiments, computing device 1506 includes one or more processors configured to process the captured image to detect an analyte in the closed configuration of QMAX device 1502D. For example, computing device can be configured to count a number of a specific analyte captured in the image, as discussed below with respect to FIG. 15.

In some embodiments, to enable the camera to image fluid sample 1504C, one or both of the first and second plates of QMAX device 1502D can be transparent. In some embodiments, a light source from either computing device 1506 or an external source can be directed at QMAX device 1502D to enable the camera to detect or image fluid sample 1504C.

In some embodiments, system 1500 includes adaptor device 1520 configured to assist computing device 1506 in imaging fluid sample 1504C. In some embodiments, adaptor device 1502 includes a housing 1522 having a slot 1524 to receive QMAX device 1502D in the closed configuration. Additionally, housing 1522 can be mounted to computing device 1506. In some embodiments, adaptor device 1520 includes optics for facilitating the imaging and/or signal processing of fluid sample 1504C by computing device 1506. In some embodiments, housing 1522 includes a mount configured to hold optics on computing device 1506. In some embodiments, an element of the optics in housing 1522 can be movable relative to housing 1522. In some embodiments, with or without the assistance of adaptor device 1520, computing device 1506 can be configured to receive an image 1508 of the imaging of fluid sample 1504C.

In some embodiments, computing device 1506 is configured to wirelessly communicate information associated with image 1508 (e.g., the actual image 1508) to server 1530. In some embodiments, computing device 1506 can be configured to communicate with server 1530 via WiFi or a cellular network. In some embodiments, server 1530 can be located in a cloud and accessed by computing device 1506 via a cloud network. In some embodiments, server 1530 can be configured to further analyze image 1508 or associated results. For example, server 1530 can include greater processing capability refine the analysis performed at computing device 1506. In some embodiments, server 1530 can be associated with a medical professional, a medical facility, or an insurance company. In some embodiments, server 1530 can be refine the results provided by computing device 1506 and provide information (e.g., the refined results) back to computing device 1506 via a wireless communication network. In some embodiments, the information received by the computing device 1506 can be a prescription, a diagnosis, or a recommendation from a medical processional.

Figure 10A:
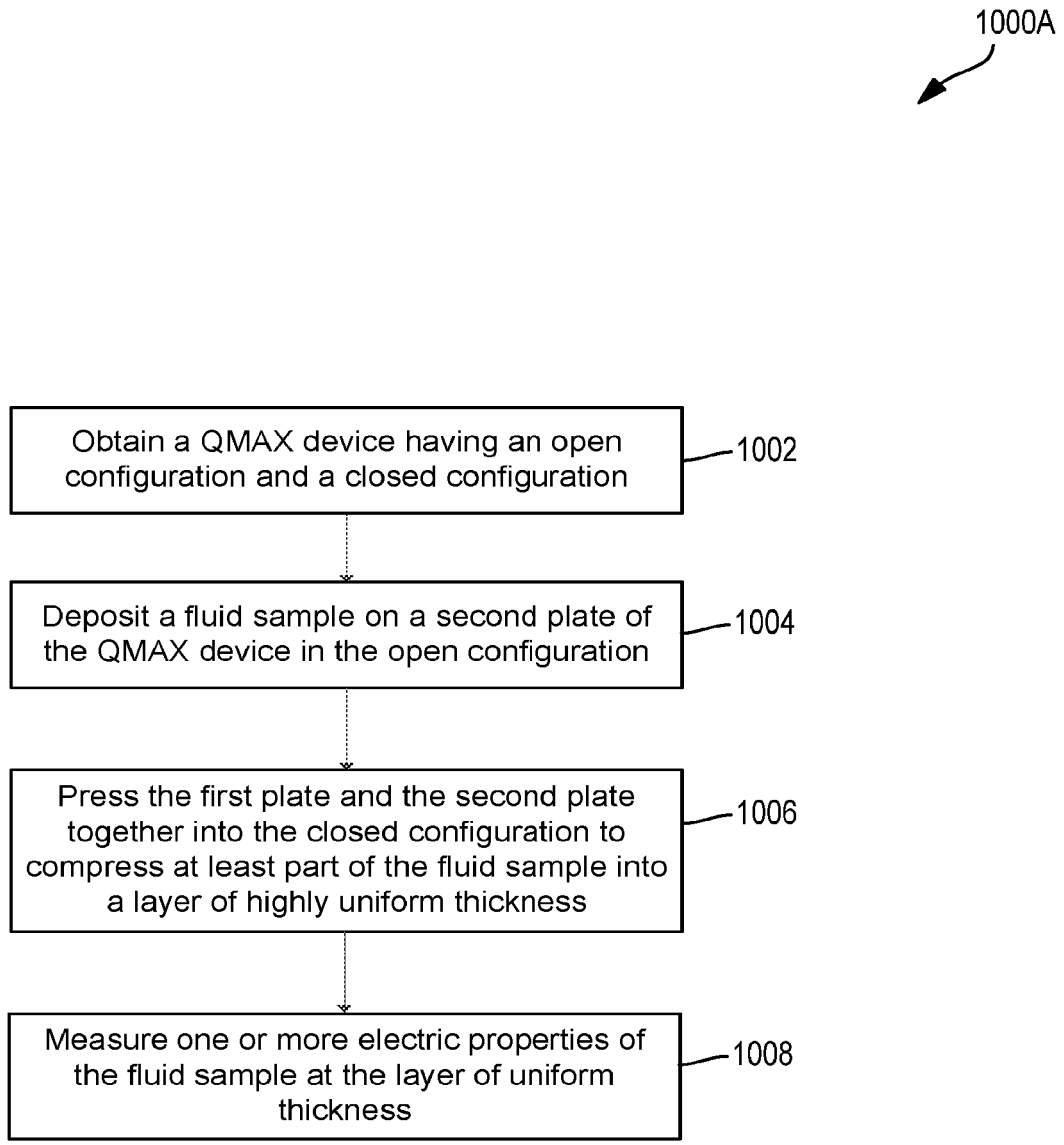
FIG. 10A illustrates a method for performing bio/chemical material assay of a fluid sample using a QMAX device, according to some embodiments.

FIG. 10A illustrates a method 1000A for performing bio/chemical material assay of a fluid sample using a QMAX device, according to some embodiments.

In step 1002, the QMAX device having an open configuration and a closed configuration is obtained. In some embodiments, the QMAX device includes a first plate, a second plate, and spacers fixed on one or both of the first and second plates. The spacers have a predetermined substantially uniform height. In some embodiments, the first and second plates are movable relative to each other into different configurations, including the open configuration and the closed configuration. The first and second plate each has a respective inner surface that has a sample contact area for contacting the fluid sample. In some embodiments, the first plate includes a first electrode and the second plate includes a second electrode, as shown in FIGS. 3A-B. In some embodiments, the first plate includes one or more first electrodes and the second plate includes one or more second electrodes, as shown in FIGS. 1A-B. In some embodiments, the second plate includes the first electrode and the second electrode, as shown in FIGS. 4A-B and 5A-B.

In step 1004, the fluid sample is deposited on the second plate when the QMAX device is in the open configuration. In some embodiments, in the open configuration, the first and second plates are partially or entirely separated apart and the spacing between the first and second plates is not regulated by the spacers. In some embodiments, the fluid sample can be deposited on both the first and second plates. In some embodiments, the fluid sample can be deposited at the center of the second plate.

In step 1006, the first and second plates are pressed together into the closed configuration to compress at least part of the fluid sample into a layer of substantially uniform thickness. In some embodiments, in the closed configuration, the layer of the at least part of the fluid sample is confined by the inner surfaces of the first and second plates and is regulated by the spacers. In some embodiments, by compressing the fluid sample, the first and second electrodes are in contact with the fluid sample at the layer of uniform thickness.

In step 1008, one or more electric properties of the fluid sample at the layer of uniform thickness are measured through the first and second electrodes. In some embodiments, the one or more electric properties include one or more of a current, a capacitance, a potential, a conductance, impedance, a permittivity, or combination thereof. In some embodiments, a voltage is induced between the first and second electrodes to enable the one or more electric properties of the fluid sample to be measured. In some embodiments, by applying electric potential to the first and second electrodes to induce the voltage, electrons in the sample liquid can be permitted to pass between the first and second electrodes. In some embodiments, the QMAX device includes a measuring device to measure the one or more electric properties such as permittivity of the fluid sample at the layer of substantially uniform thickness.

In some embodiments, the QMAX device includes a barrier membrane, such as barrier membrane 512 as described with respect to FIGS. 5A-B, to enable the measuring device to measure an electrolyte concentration of the fluid sample.

Figure 10B:
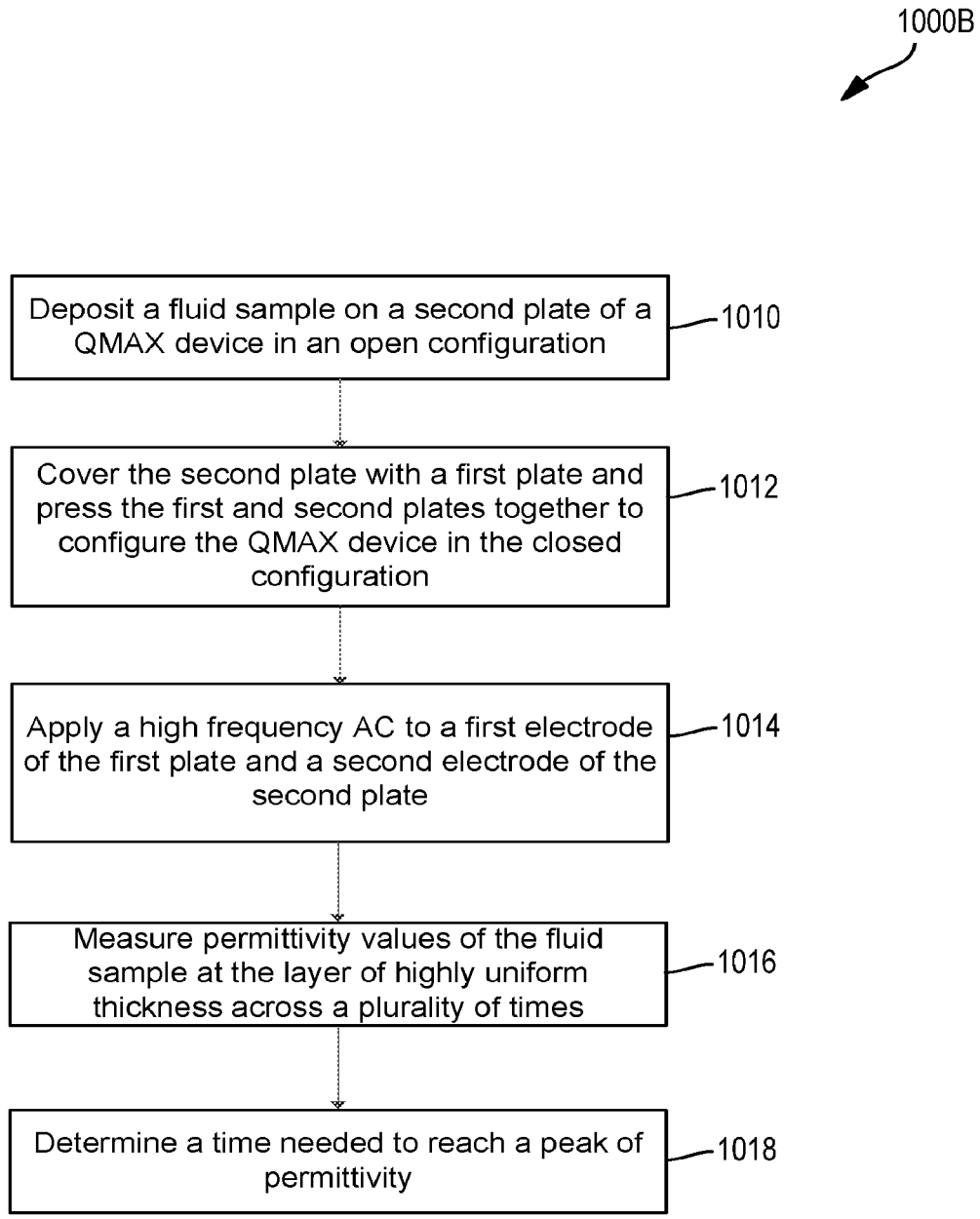
FIG. 10B illustrates a method for measuring permittivity of a fluid sample using a QMAX device, according to some embodiments.

FIG. 10B illustrates a method 1000B for measuring permittivity, an example electric property, of a fluid sample using a QMAX device, according to some embodiments. In some embodiments, the fluid sample can be a blood sample, as described with respect to FIGS. 1A-B, and the QMAX device can be configured to determine coagulation characteristics of the fluid sample based on the measured permittivity. In some embodiments, the QMAX device, as described with respect to method 1000A, can perform method 1000B. For example, the QMAX device includes a first plate, a second plate, and spacers fixed on one or both of the first and second plates. The spacers have a predetermined substantially uniform height. In some embodiments, the first and second plates are movable relative to each other into different configurations, including the open configuration and the closed configuration. The first and second plate each has a respective inner surface that has a sample contact area for contacting the fluid sample. In some embodiments, the first plate includes a first electrode and the second plate includes a second electrode. As discussed above with respect to FIG. 10A, other placement and numbers of the first and second electrodes are possible according to some embodiments.

In step 1010, the fluid sample is deposited on the second plate of the QMAX device in the open configuration. In some embodiments, the fluid sample is a blood sample that is deposited at the center of the second plate.

In step 1012, the first plate covers the second plate and the first and second plates are pressed together to configure the QMAX device in the closed configuration. In some embodiments, the fluid sample is compressed into a layer of substantially uniform thickness in the closed configuration.

In step 1014, a high frequency AC is applied by a power source to the first and second electrodes.

In step 1016, permittivity values of the fluid sample at the layer of substantially uniform thickness are measured in real time across a plurality of times. In some embodiments, the QMAX device includes a measurement device configured to measure the permittivity values at predetermined times, e.g., at 15 s, 30 s, 45 s, 1 min, etc.

In step 1018, a time needed to reach a peak of permittivity (Tpeak) is determined. In some embodiments, to determine the peak, the measurement device can be configured to determine the maximum permittivity value of the permittivity values being measured. In some embodiments, the QMAX device can be configured to determine coagulation characteristics of the fluid sample based on the peak of permittivity. In some embodiments, where the fluid sample is a blood sample, the permittivity parameters (e.g., the peak of permittivity) can be used to calculate PT or aPPT.

Figure 11:
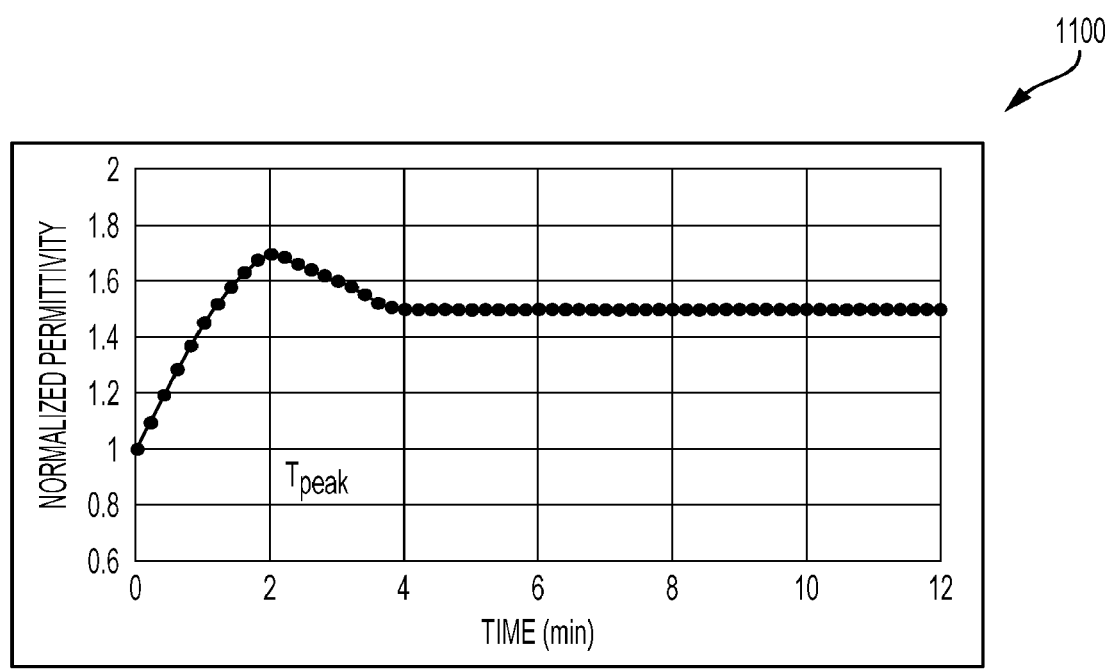
FIG. 11 illustrates a graph that shows representative measurement results of permittivity that was experimentally obtained using a QMAX device, according to some embodiments.

FIG. 11 illustrates a graph 1100 that shows representative measurement results of permittivity that was experimentally obtained using a QMAX device, according to some embodiments. In some embodiments, the measurement results were obtained using QMAX device 400 of FIGS. 4A-B. In some embodiments, to obtain the permittivity results, method 1000B was performed. In the experimental setup of FIG. 11, a blood sample was deposited on QMAX device 400 and a 1M Hz AC was applied to electrodes 408 and 410 of QMAX device 400 once first plate 402 and second plate 404 were pressed together to configure QMAX device 400 in a closed configuration. Then, as shown in graph 1100, permittivity was measured and normalized at a plurality of time periods ranging from 0 min to 12 min. In some embodiments, the plurality of permittivity values can be used as an indicator for blood coagulation properties. Further, in this experimental setup, the peak of normalized permittivity (Tpeak) is determined to be around 2 minutes, which may be used as an indicator for a coagulation property of the blood sample.

Figure 12A:
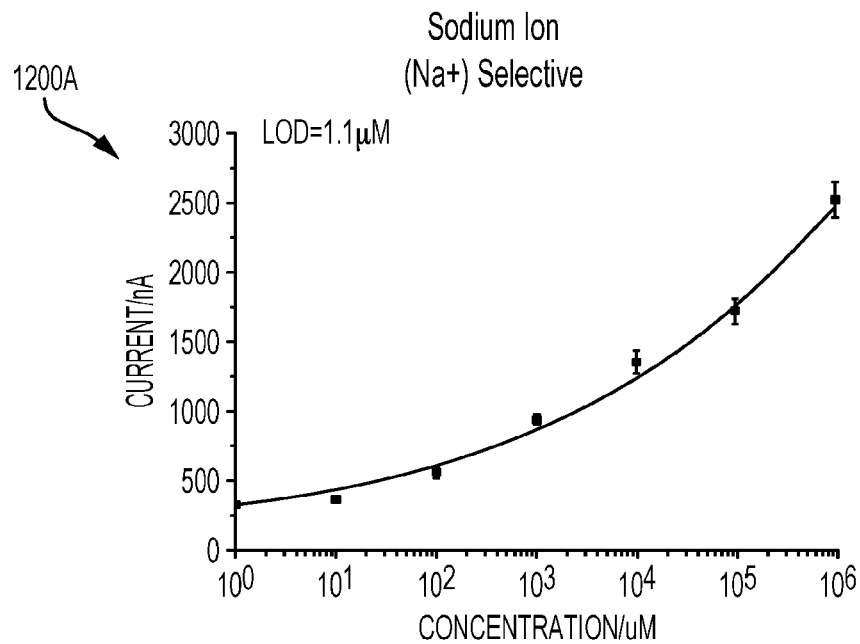
FIGS. 12A-B illustrate graphs that show representative measurement results of electrolyte concentrations that were experimentally obtained using a QMAX device, according to some embodiments.
Figure 12B:
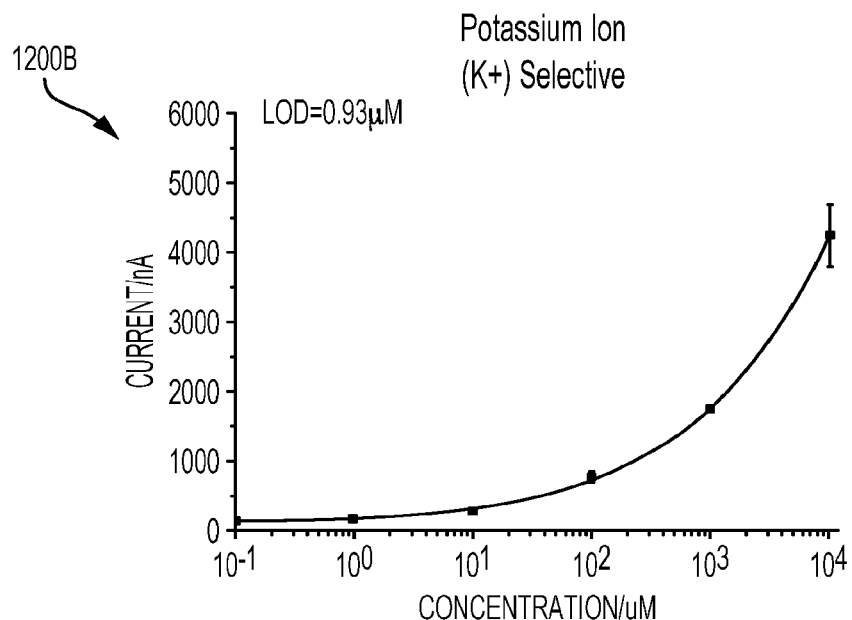

FIGS. 12A-B illustrate graphs 1200A-B that show representative measurement results of electrolyte concentrations of a fluid sample that were experimentally obtained using a QMAX device, according to some embodiments. In these examples, method 1000A of FIG. 10A was performed using QMAX device 500 of FIGS. 5A-B.

To obtain the representative results of graphs 1200A-B, QMAX device 500 having the following properties were used: (1) second plate 404 had dimensions of 32 mm×24 mm×1 mm, and includes electrode 508 and electrode 510 each made with gold; (2) each of electrode 508 and electrode 510 had two areas, one contact pad area (3 mm×3 mm×50 nm gold) and one measurement pad (20 mm×5 mm×50 nm gold); (3) a measurement area of electrode 510 was coated with an ion-selective barrier membrane 512 for different application (selective for ions such as but not limited to Na+, K+, etc.) with a thickness around 1 um; (4) barrier membrane 512 in FIG. 12A was Na+ selective membrane that contained 1 wt % ionophore ET H 2120.33 wt 5% PVC, and 66 wt % DOS; (5) barrier membrane 512 in FIG. 12B was K+ selective membrane that contained valinomycin 2.0 mg, BBPA 65.5 mg, KTpClPB 0.5 mg, PVC 33.0 mg. This mixture was dissolved in ca. 1 ml tetrahydrofuran; (6) first plate 502 included spacers made from a micro-pillar array with 30×40 um pillar size, 80 um inter spacing distance, and 30 um pillar height, made on 175 um thick PMMA film; (7) power source 506 was a DC electrical source with 0V to 10V range applied on electrodes 508 and 510; and (8) a current meter serially connected with one of electrodes 508 and 510 to monitor current flow.

To obtain the representative results of graphs 1200A-B, method 1000A was performed. In particular, the experiment setup included the following steps: (1) a drop of 12 uL NaCl and KCl solution fluid sample with concentrations between 0.1 uM to 1M was deposited on second plate 504; (2) first plate 502 was pressed onto second plate 504; (3) and current flow through electrodes 508 and 510 was measured at 1V. As shown in FIGS. 12A-B, a current value was measured and plotted at 1V bias versus different concentration of Na+ (graph 1200A) and K+(graph 1200B), showing LOD of Na+1.1 µM and K+0.93 µM, while the selectivity of sodium membrane (Na+:K+) is 14 and the selectivity of potassium membrane (K+:Na+) is 12.

Figure 13:
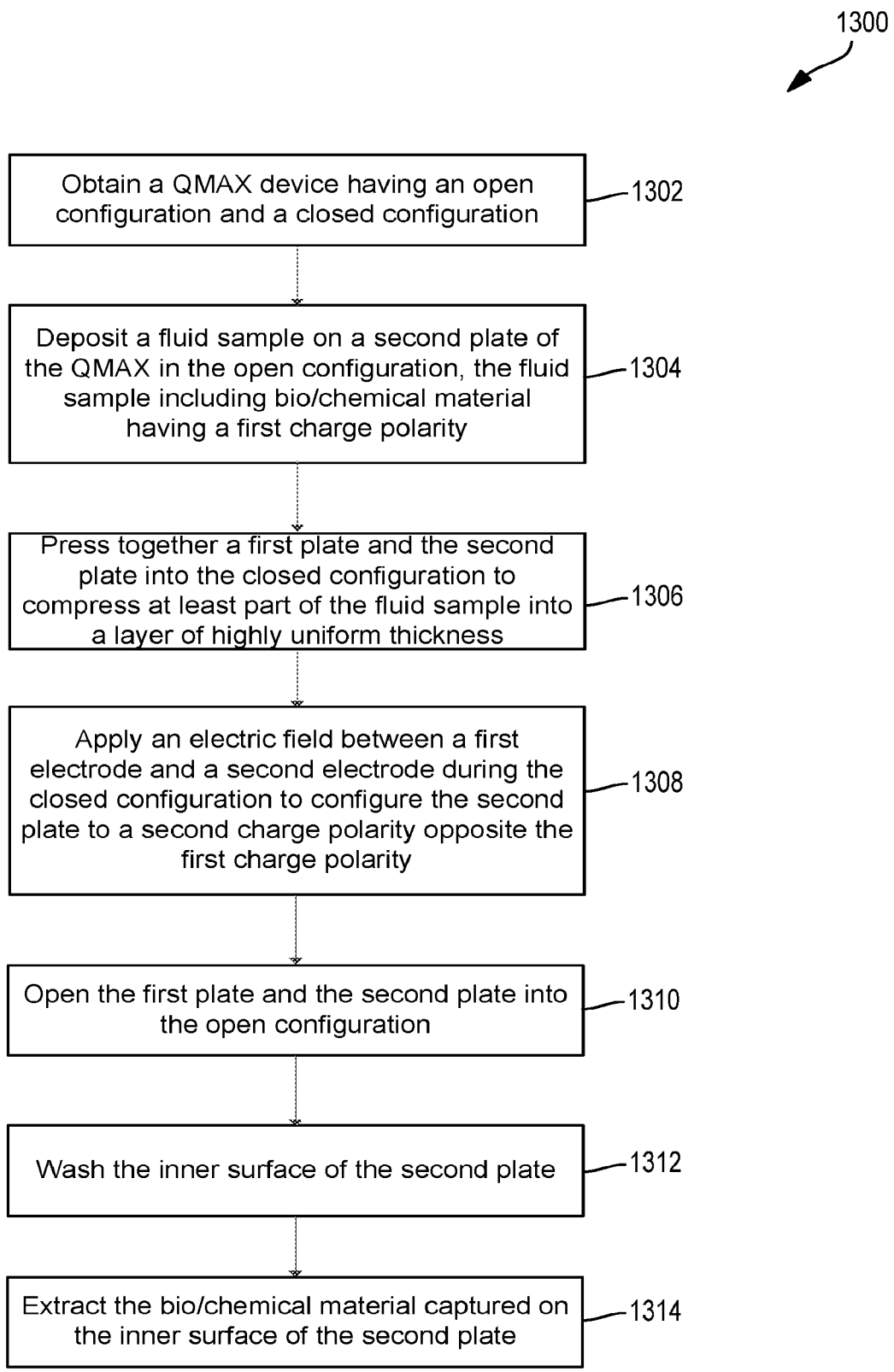
FIG. 13 illustrates a method for extracting charged bio/chemical material from a fluid sample using a QMAX device, according to some embodiments.

FIG. 13 illustrates a method 1300 for extracting charged bio/chemical material from a fluid sample using a QMAX device, according to some embodiments. In some embodiments, the charged material that can be extracted from the fluid sample can include, for example, nucleic acids such as but not limited to DNA and RNA.

In step 1302, the QMAX device having an open configuration and a closed configuration is obtained. In some embodiments, the QMAX device includes a first plate, a second plate, and spacers fixed on one or both of the first and second plates. The spacers have a predetermined substantially uniform height. In some embodiments, the first and second plates are movable relative to each other into different configurations, including the open configuration and the closed configuration. The first and second plate each has a respective inner surface that has a sample contact area for contacting the fluid sample. In some embodiments, the first plate includes a first electrode positioned on an outer surface of the first plate and the second plate includes a second electrode positioned on an outer surface of the second plate, as shown in FIG. 2A. In some embodiments, the first plate includes one or more first electrodes positioned on an outer surface of the first plate and the second plate includes one or more second electrodes positioned on an outer surface of the second plate, as shown in FIG. 2B. In some embodiments, the first electrode is positioned outside of and not in contact with the first plate and the second electrode is positioned outside of and not in contact with the second plate, as shown in FIG. 2C.

In step 1304, the fluid sample is deposited on the second plate when the QMAX device is in the open configuration. In some embodiments, in the open configuration, the first and second plates are partially or entirely separated apart and the spacing between the first and second plates is not regulated by the spacers. In some embodiments, the fluid sample can be deposited on one of or both of the first and second plates. In some embodiments, the fluid sample includes the charged bio/chemical material having a first charge polarity. In some embodiments, the charged bio/chemical material can be one of nucleic acid, a protein, a molecule, a virus, bacteria, cell, or nanoparticles.

In step 1306, the first and second plates are pressed together into the closed configuration to compress at least part of the fluid sample into a layer of substantially uniform thickness. In some embodiments, in the closed configuration, the layer of the at least part of the fluid sample is confined by the inner surfaces of the first and second plates and is regulated by the spacers. Further, the layer of substantially uniform thickness can be substantially stagnant relative to the first and second plates, according to some embodiments.

In some embodiments, the fluid sample can be a biological sample such as, for example, blood. In these embodiments, the charged bio/chemical material in the fluid sample may be nucleic acids, which have a negative charge. In some embodiments, a target component of the fluid sample is lysed to release the nucleic acids. In some embodiments, the uniform height of the spacers is configured to allow the first and second plates to lyse the target component in the fluid sample while the fluid sample is compressed into the layer of uniform thickness in the closed configuration of the QMAX. In some embodiments, the target component is cells in the fluid sample. In some embodiments, the target component is blood cells in the fluid sample. As described with respect to FIGS. 1A-B, the fluid sample may be whole blood or serum blood. Further, the fluid sample may be a blood sample having one or more added coagulation regulates, according to some embodiments.

In step 1308, an electric field is applied by a power source between the first and second electrodes for a period of time during the closed configuration to configure the second plate to a second charge polarity opposite the first charge polarity of the bio/chemical material. In some embodiments, the electric field is controllable by the power source. In some embodiments, the second plate becomes conductive with a voltage bias applied by the first and second electrodes, which enables the second plate to become charged to the polarity opposite that of the charged bio/chemical material.

In some embodiments, the bio/chemical material can be a negatively-charged component such as nucleic acids. In these embodiments, the power source can be configured to adjust the electric filed to render the second plate positively charged to enable the second plate to capture the negatively-charged components of the nucleic acids at the inner surface of the second plate.

In some embodiments, the electrostatic interaction between the charged bio/chemical material and the opposite charged surface of the second plate makes the charged bio/chemical material immobilized at the opposite charged surface. In some embodiments, after a period of time has elapsed, most of the charged bio/chemical material in the fluid sample would have diffused to the sample contact area of the opposite charged surface and become immobilized at that opposite charged surface until a saturation extraction is reached.

In step 1310, the first and second plates are opened into the open configuration.

In step 1312, the inner surface of the second plate is washed. In some embodiments, the inner surface is washed of contaminates and other un-captured components. In some embodiments, the inner surface is washed with a sponge. In some embodiments, the sponge includes flexible porous material having pores that are deformable and having a size and surface properties configured to absorb the washing medium into the material or release the washing medium out of the material, when the shape of the pores are changed. In some embodiments, washing the inner surface with the sponge includes pressing the sponge with a force (and changing the shape of the pores) to release a washing medium in the sponge onto the inner surface and then removing the force (and changing the shapes of the pores) to allow the sponge to reabsorb the washing medium.

In step 1314, the bio/chemical material captured on the inner surface of the second plate washed of contaminates is extracted for further analysis.

In some embodiments, a detection agent can be added to the charged bio/chemical material and the detection agent can be configured to bind to an analyte of the bio/chemical material to produce a detectable signal. In some embodiments where the charged bio/chemical material is nucleic acids, the detection agent can be a polymerase chain reaction (PCR) medium added to the captured nucleic acids to conduct a PCR reaction. In some embodiments, the PCR reaction is performed by changing a temperature of the second plate by electromagnetic signals. In some embodiments, the temperature can be changed by electric signals from the second electrode and induced by the power source. In some embodiments, the PCR reaction is performed by changing a light emitted on the second plate.

Figure 14:
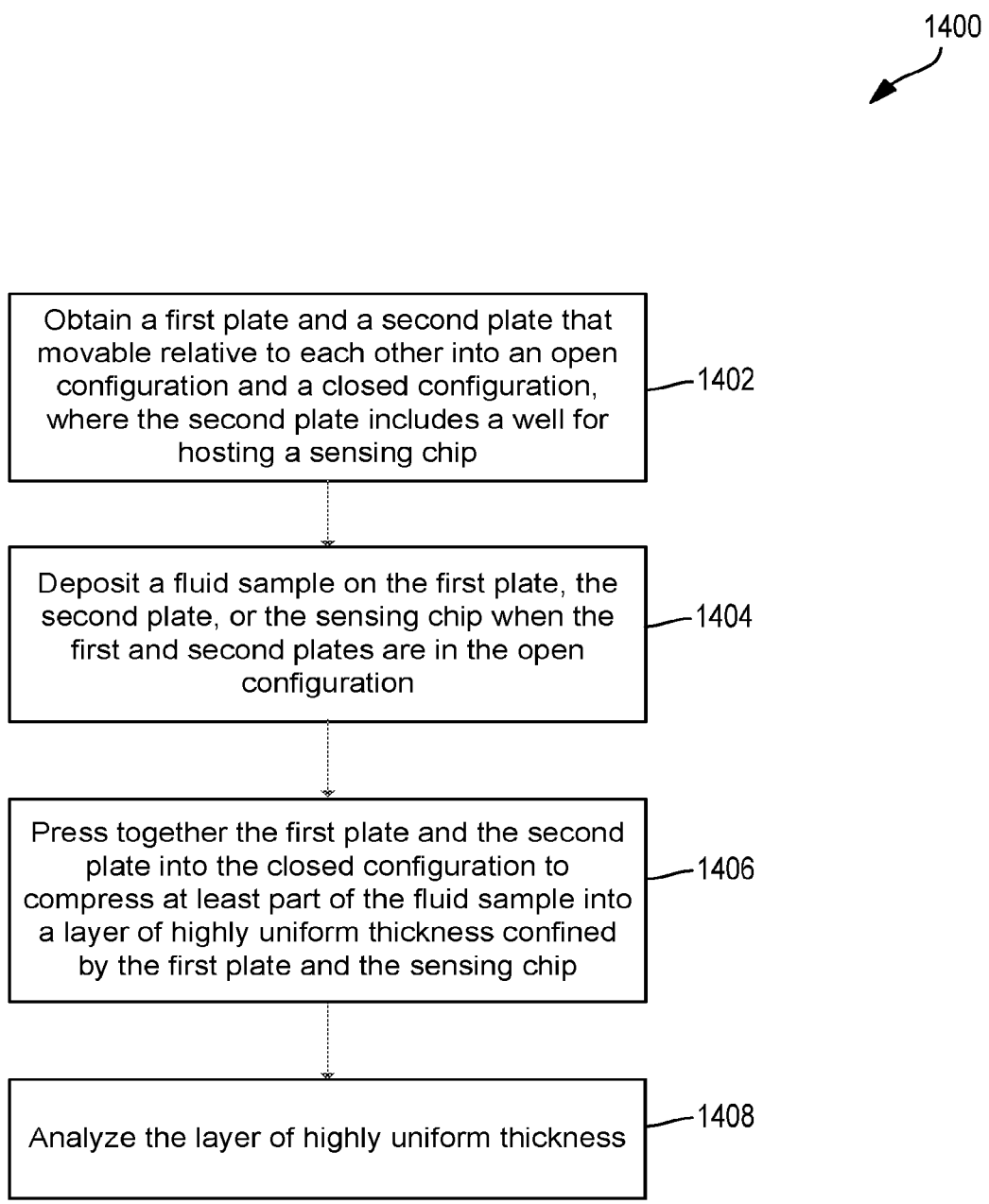
FIG. 14 illustrates a method for hosting a sensing chip on a QMAX device, according to some embodiments.

FIG. 14 illustrates a method 1400 for hosting a sensing chip using a QMAX device, according to some embodiments. In some embodiments, the QMAX device can be QMAX device 800, as described with respect to FIGS. 8A-B.

In step 1402, a first plate and a second plate of the QMAX device are obtained that are movable relative to each other into a plurality of configurations, including an open configuration and a closed configuration. In some embodiments, one or both of the first and second plates are flexible. In some embodiments, the first plate includes, on a first inner surface, a sample contacting area for contacting a fluid sample. In some embodiments, the second plate includes, on a second inner surface, a well and the sensing chip placed inside the well. The sensing chip has a sensing surface for contacting the fluid sample. In some embodiments, one or more of the first plate, the second plate, and the sensing chip include spacers that are permanently fixed on a respective sample contact area. In some embodiments, only the sensing chip includes the spacers.

In step 1404, the fluid sample is deposited on the first plate, the second plate, or the sensing chip when the first and second plates are in the open configuration. In some embodiments, in the open configuration, the first and second plates are partially or entirely separated apart and the spacing between the first and second plates is not regulated by the spacers. In some embodiments, the fluid sample can be deposited on the sensing surface of the sensing chip.

In step 1406, the first and second plates are pressed together into the closed configuration to compress at least part of the fluid sample into a layer of substantially uniform thickness. In some embodiments, pressing together the first and second plates cause the first plate and the sensing chip to compress the fluid sample into the layer of substantially uniform thickness. In some embodiments, in the closed configuration, the layer of substantially uniform thickness is confined by the first inner surface (e.g., the sample contact area) of the first plate and the sensing surface of the sensing chip and is regulated by the first plate, the sensing chip, and the spacers. Further, the layer of substantially uniform thickness can be substantially stagnant relative to the first and second plates, according to some embodiments.

In step 1408, the sensing chip can be configured to analyze the fluid sample compressed into the layer of substantially uniform thickness. In some embodiments, sensing chip can be configured to analyze the fluid sample compressed into the layer of substantially uniform thickness in less than about 60 seconds or about 10 seconds. In some embodiments, the sensing chip can include a dry binding site of a predetermined area to bind and immobilize specific analytes in the layer. In some embodiments, analyzing the fluid sample includes detecting a predetermined analyte in the fluid sample. In some embodiments, the predetermined analyzte can be a biomarker. In some embodiments, the analyze can be nucleic acid, a protein, a cell type, or metabolite. In some embodiments, analyzing the fluid sample includes counting an amount of a specific analyte. For example, analyzing the fluid sample can include counting a number of any of the following analyzed in the fluid sample: red blood cells, white blood cells, neutrophils, lymphocytes, monocytes, eosoniphils, and basophils.

In some embodiments, the QMAX device can be configured to be operable with an adaptor device to enable at least a part of the contact area to be further analyzed by a computing device (e.g., a mobile device) including an imaging device (e.g., a camera). In some embodiments, the part of the contact area to be further analyzed can be the sensing surface of the sensing chip. In some embodiments, the adaptor further includes a slot in the housing that allows the first and second plates in the closed configuration to slide into the slot to enable the imaging device of the computing device to image the at least part of the contact area. In some embodiments, the computing device can be configured to analyze the image of the at least part of the contact area to count a number of a specific type of analyze captured by the sensing chip.

In some embodiments, to aid in further analysis such as analysis of images taking by the imaging device, the QMAX device can include a dry reagent coated on the first inner surface of the first plate or the second inner surface of the second plate. In some embodiments, the dry reagent can be a releasable agent that is released into the fluid sample upon coming into contact with the fluid sample. In some embodiments, the QMAX device can include a release time control material on the first inner surface or the second inner surface that delays the time at which the releasable dry reagent is released into the fluid sample. In some embodiments, the release time control material delays the release of the dry reagent by at least about 3 seconds.

In some embodiments, the dry reagent can include an anticoagulant or a staining reagent (e.g., a cell stain) for interacting with the target analyte (e.g., nucleic acids) in the fluid sample. In some embodiments, the dry reagent can include a labeled reagent or a fluorescently-labeled reagent configured to diffuse in the fluid sample to stain the target analyte. In some embodiments, by staining the target analyte via the dry reagent, the image of the at least part of the contact area can be more easily analyzed.

Figure 16:
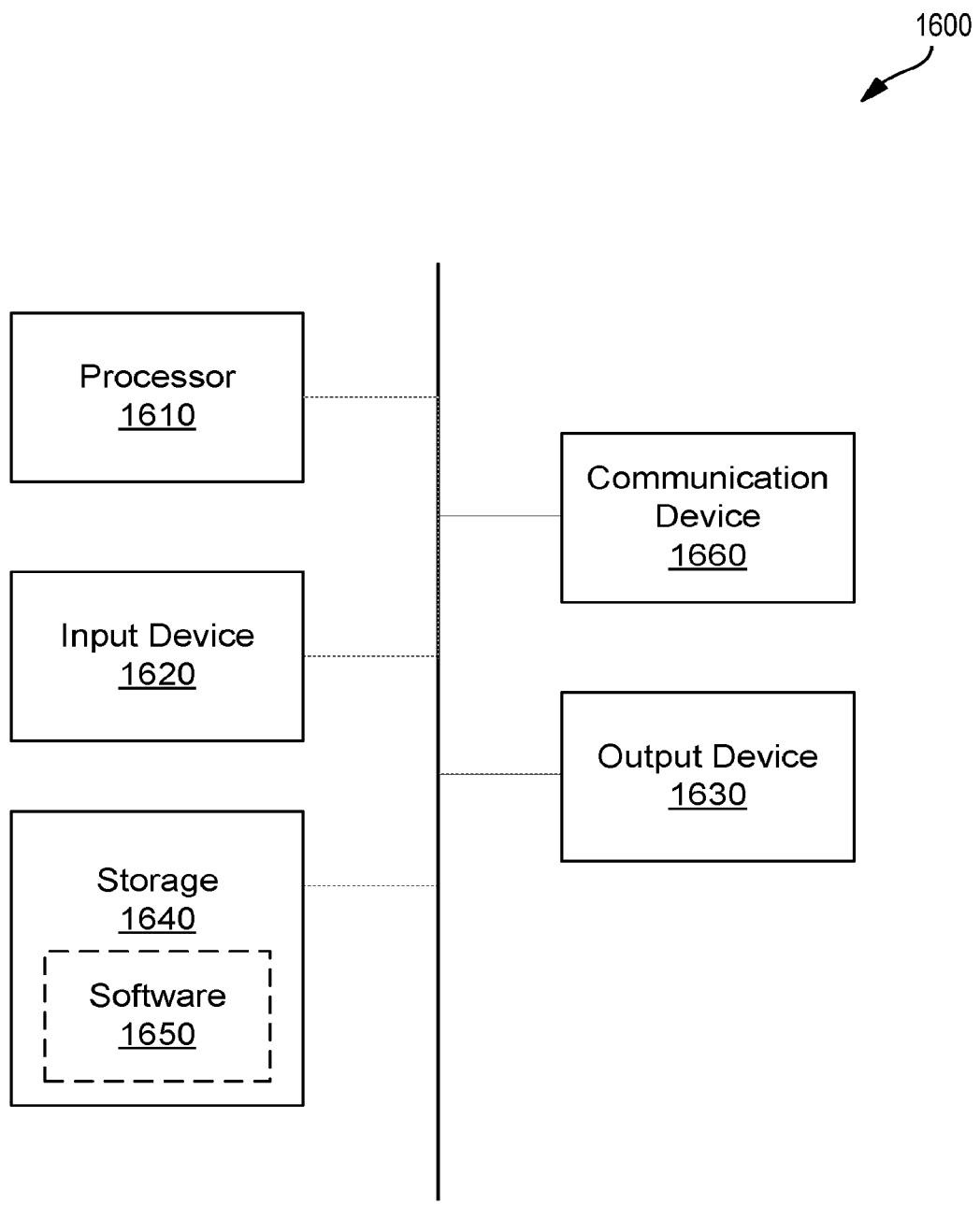
FIG. 16 illustrates an example of a computer, in accordance with one embodiment.

FIG. 16 illustrates an example of a computer in accordance with one embodiment. Computer 1600 can be a component of a system for analyzing a fluid sample such as computing device 1512 or server 1530 from FIG. 15, according to some embodiments.

Computer 1600 can be a host computer connected to a network. Computer 1600 can be a client computer or a server. As shown in FIG. 16, computer 1600 can be any suitable type of microprocessor-based device, such as a personal computer, workstation, server, Internet Of Things device, or handheld computing device, such as a phone or tablet. The computer can include, for example, one or more of processor 1610, input device 1620, output device 1630, storage 1640, and communication device 1660. Input device 1620 and output device 1630 can generally correspond to those described above and can either be connectable or integrated with the computer.

Input device 1620 can be any suitable device that provides input, such as a touch screen or monitor, keyboard, mouse, or voice-recognition device. Output device 1630 can be any suitable device that provides output, such as a touch screen, monitor, printer, disk drive, or speaker.

Storage 1640 can be any suitable device that provides storage, such as an electrical, magnetic, or optical memory, including a RAM, cache, hard drive, CD-ROM drive, tape drive, or removable storage disk. Communication device 1660 can include any suitable device capable of transmitting and receiving signals over a network, such as a network interface chip or card. The components of the computer can be connected in any suitable manner, such as via a physical bus or wirelessly. Storage 1640 can be a non-transitory computer-readable storage medium comprising one or more programs, which, when executed by one or more processors, such as processor 1610, cause the one or more processors to execute one or more steps of methods described herein.

Software 1650, which can be stored in storage 1640 and executed by processor 1616, can include, for example, the programming that embodies the functionality of the present disclosure (e.g., as embodied in the systems, computers, servers, and/or devices as described above). In some embodiments, software 1650 can include a combination of servers such as application servers and database servers.

Software 1650 can also be stored and/or transported within any computer-readable storage medium for use by or in connection with an instruction execution system, apparatus, or device, such as those described above, that can fetch and execute instructions associated with the software from the instruction execution system, apparatus, or device. In the context of this disclosure, a computer-readable storage medium can be any medium, such as storage 1640, that can contain or store programming for use by or in connection with an instruction execution system, apparatus, or device.

Software 1650 can also be propagated within any transport medium for use by or in connection with an instruction execution system, apparatus, or device, such as those described above, that can fetch and execute instructions associated with the software from the instruction execution system, apparatus, or device. In the context of this disclosure, a transport medium can be any medium that can communicate, propagate, or transport programming for use by or in connection with an instruction execution system, apparatus, or device. The transport-readable medium can include, but is not limited to, an electronic, magnetic, optical, electromagnetic, or infrared wired or wireless propagation medium.

Computer 1600 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Computer 1600 can implement any operating system suitable for operating on the network. Software 1650 can be written in any suitable programming language, such as C, C++, Java, or Python. In various embodiments, application software embodying the functionality of the present disclosure can be deployed in different configurations, such as in a client/server arrangement or through a Web browser as a Web-based application or Web service, for example.

Embodiments and Related Disclosures

The present disclosure includes a variety of embodiments, which can be combined in multiple ways as long as the various components do not contradict one another. The embodiments should be regarded as a single invention file: each filing has other filing as the references and is also referenced in its entirety and for all purpose, rather than as a discrete independent. These embodiments include not only the disclosures in the current file, but also the documents that are herein referenced, incorporated, or to which priority is claimed.

Definitions

The terms used in describing the devices, systems, and methods herein are defined in the current application, or in PCT Application (designating U.S.) Nos. PCT/US2016/046437 and PCT/US2016/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which are incorporated herein by reference in their entireties for all purposes.

The terms "CROF Card (or card)", "COF Card", "QMAX-Card", "Q-Card", "CROF device", "COF device", "QMAX-device", "CROF plates", "COF plates", and "QMAX-plates" are interchangeable, except that in some embodiments, the COF card may not include spacers; and the terms refer to a device that comprises a first plate and a second plate that are movable relative to each other into different configurations (including an open configuration and a closed configuration), and that includes spacers (except some embodiments of the COF card) that regulate the spacing between the plates. The term "X-plate" refers t=o one of the two plates in a CROF card, wherein the spacers are fixed to this plate. More descriptions of the COF Card, CROF Card, and X-plate are given in the provisional application serial nos. 62/456,065, filed on Feb. 7, 2017, which is incorporated herein by reference in its entirety for all purposes.

Q-Card, Spacer and Uniform Sample Thickness, and Amplification Surfaces

The devices, systems, and methods herein disclosed can include or use Q-cards, spacers, and uniform sample thickness embodiments for sample detection, analysis, and quantification. In some embodiments, the Q-card includes spacers, which help to render at least part of the sample into a layer of high uniformity. The structure, material, function, variation and dimension of the spacers, as well as the uniformity of the spacers and the sample layer, are herein disclosed, or listed, described, and summarized in PCT Application (designating U.S.) Nos. PCT/US2016/046437 and PCT/US2016/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456, 504, which was filed on Feb. 8, 2017, all of which applications are incorporated herein by reference in their entireties for all purposes.

Hinges, Opening Notches, Recessed Edge and Sliders

The devices, systems, and methods herein disclosed can include or use Q-cards for sample detection, analysis, and quantification. In some embodiments, the Q-card comprises hinges, notches, recesses, and sliders, which help to facilitate the manipulation of the Q card and the measurement of the samples. The structure, material, function, variation and dimension of the hinges, notches, recesses, and sliders are herein disclosed, or listed, described, and summarized in PCT Application (designating U.S.) Nos. PCT/US2016/046437 and PCT/US2016/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein by reference in their entireties for all purposes.

In some embodiments of QMAX, the sample contact area of one or both of the plates comprises a compressed open flow monitoring surface structures (MSS) that are configured to monitoring how much flow has occurred after COF. For examples, the MSS comprises, in some embodiments, shallow square array, which will cause friction to the components (e.g. blood cells in a blood) in a sample. By checking the distributions of some components of a sample, one can obtain information related to a flow, under a COF, of the sample and its components.

The depth of the MSS can be $\frac{1}{1000}$, $\frac{1}{100}$, $\frac{1}{10}$, $\frac{1}{5}$, $\frac{1}{2}$ of the spacer height or in a range of any two values, and in either protrusion or well form.

Q-Card, Sliders, and Smartphone Detection System

The devices, systems, and methods herein disclosed can include or use Q-cards for sample detection, analysis, and quantification. In some embodiments, the Q-cards are used together with sliders that allow the card to be read by a smartphone detection system. The structure, material, function, variation, dimension and connection of the Q-card, the sliders, and the smartphone detection system are herein disclosed, or listed, described, and summarized in PCT Application (designating U.S.) Nos. PCT/US2016/046437 and PCT/US2016/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456, 504, which was filed on Feb. 8, 2017, all of which applications are incorporated herein by reference in their entireties for all purposes.

Dimensions

The devices, apparatus, systems, and methods herein disclosed can include or use a QMAX device, which can comprise plates and spacers, as discussed above with respect to FIGS. 1-9 and 15 In some embodiments, the dimension of the individual components of the QMAX device and its adaptor are listed, described and/or summarized in PCT Application (designating U.S.) No. PCT/US2016/046437 filed on Aug. 10, 2016, and U.S. Provisional Application Nos. 62,431,639 filed on Dec. 9, 2016, and 62/456,287 filed on Feb. 8, 2017, which are all hereby incorporated by reference by their entireties.

In some embodiments, further to the dimensions of the various components of QMAX device described above, the dimensions can be as listed in the Tables below:

| | Plates: | |
|---|---|---|
| Parameters | Embodiments | Preferred Embodiments |
| Shape | round, ellipse, rectangle, triangle, polygonal, ring-shaped, or any superposition of these shapes; the two (or more) plates of the QMAX card can have the same size and/or shape, or different size and/or shape; | at least one of the two (or more) plates of the QMAX card has round corners for user safety concerns, wherein the round corners have a diameter of 100 um or less, 200 um or less, 500 um or less, 1 mm or less, 2 mm or less, 5 mm or less, 10 mm or less, 50 mm |

Plates:

| Parameters | Embodiments | Preferred Embodiments |
|---|---|---|
| Thickness | the average thickness for at least one of the plates is 2 nm or less, 10 nm or less, 100 nm or less, 200 nm or less, 500 nm or less, 1000 nm or less, 2 μm (micron) or less, 5 μm or less, 10 μm or less, 20 μm or less, 50 μm or less, 100 μm or less, 150 μm or less, 200 μm or less, 300 μm or less, 500 μm or less, 800 μm or less, 1 mm (millimeter) or less, 2 mm or less, 3 mm or less, 5 mm or less, 10 mm or less, 20 mm or less, 50 mm or less, 100 mm or less, 500 mm or less, or in a range between any two of these values | For at least one of the plates is in the range of 0.5 to 1.5 mm; around 1 mm; in the range of 0.15 to 0.2 mm; or around 0.175 mm |
| Lateral Area | For at least one of the plate is 1 mm2 (square millimeter) or less, 10 mm2 or less, 25 mm2 or less, 50 mm2 or less, 75 mm2 or less, 1 cm2 (square centimeter) or less, 2 cm2 or less, 3 cm2 or less, 4 cm2 or less, 5 cm2 or less, 10 cm2 or less, 100 cm2 or less, 500 cm2 or less, 1000 cm2 or less, 5000 cm2 or less, 10,000 cm2 or less, 10,000 cm2 or less, or in a range between any two of these values | For at least one plate of the QMAX card is in the range of 500 to 1000 mm2; or around 750 mm2. |
| Lateral Linear Dimension (width, length, or diameter, etc.) | For at least one of the plates of the QMAX card is 1 mm or less, 5 mm or less, 10 mm or less, 15 mm or less, 20 mm or less, 25 mm or less, 30 mm or less, 35 mm or less, 40 mm or less, 45 mm or less, 50 mm or less, 100 mm or less, 200 mm or less, 500 mm or less, 1000 mm or less, 5000 mm or less, or in a range between any two of these values | For at least one plate of the QMAX card is in the range of 20 to 30 mm; or around 24 mm |
| Recess width | 1 um or less, 10 um or less, 20 um or less, 30 um or less, 40 um or less, 50 um or less, 100 um or less, 200 um or less, 300 um or less, 400 um or less, 500 um or less, 7500 um or less, 1 mm or less, 5 mm or less, 10 mm or less, 100 mm or less, or 1000 mm or less, or in a range between any two of these values. | In the range of 1 mm to 10 mm; Or About 5 mm |

Hinge:

| Parameters | Embodiments | Preferred Embodiments |
|---|---|---|
| Number | 1, 2, 3, 4, 5, or more | 1 or 2 |
| Length of Hinge Joint | 1 mm or less, 2 mm or less, 3 mm or less, 4 mm or less, 5 mm or less, 10 mm or less, 15 mm or less, 20 mm or less, 25 mm or less, 30 mm or less, 40 mm or less, 50 mm or less, 100 mm or less, 200 mm or less, or 500 mm or less, or in a range between any two of these values | In the range of 5 mm to 30 mm. |
| Ratio (hinge joint length vs. aligning plate edge length | 1.5 or less, 1 or less, 0.9 or less, 0.8 or less, 0.7 or less, 0.6 or less, 0.5 or less, 0.4 or less, 0.3 or less, 0.2 or less, 0.1 or less, 0.05 or less or in a range between any two of these values. | In the range of 0.2 to 1; or about 1 |
| Area | 1 mm2 or less, 5 mm2 or less, 10 mm2 or less, 20 mm2 or less, 30 mm2 or less, 40 mm2 or less, 50 mm2 or less, 100 mm2 or less, 200 mm2 or less, 500 mm2 or less, or in a range between any of the two values | In the range of 20 to 200 mm2; or about 120 mm2 |
| Ratio (hinge area vs. plate area) | 1 or less, 0.9 or less, 0.8 or less, 0.7 or less, 0.6 or less, 0.5 or less, 0.4 or less, 0.3 or less, 0.2 or less, 0.1 or less, 0.05 or less, 0.01 or less or in a range between any two of these values | In the range of 0.05 to 0.2, around 0.15 |
| Max. Open Degree | 15 or less, 30 or less, 45 or less, 60 or less, 75 or less, 90 or less, 105 or less, 120 or less, 135 or less, 150 or less, 165 or less, 180 or less, 195 or less, 210 or less, 225 or less, 240 or less, 255 or less, 270 or less, 285 or less, 300 or less, 315 or less, 330 or less, 345 or less or 360 or less degrees, or in a range between any two of these values | In the range of 90 to 180 degrees |
| No. of Layers | 1, 2, 3, 4, 5, or more | 1 or 2 |
| Layer thickness | 0.1 um or less, 1 um or less, 2 um or less, 3 um or less, 5 um or less, 10 um or less, 20 um or less, 30 um or less, 50 um or less, 100 um or less, 200 um or less, 300 um or less, 500 um or less, 1 mm or less, 2 mm or less, and a range between any two of these values | In the range of 20 um to 1 mm; or Around 50 um |
| Angle-maintaining | Limiting the angle adjustment with no more than ±90, ±45, ±30, ±25, ±20, ±15, ±10, ±8, ±6, ±5, ±4, ±3, ±2, or ±1, or in a range between any two of these values | No more than ±2 |

| Notch: | | |
|---|---|---|
| Parameters | Embodiments | Preferred Embodiments |
| Number | 1, 2, 3, 4, 5, or more | 1 or 2 |
| Shape | round ellipse, rectangle, triangle, polygon, ring-shaped, or any superposition or portion of these shapes. | Part of a circle |
| Positioning | Any location along any edge except the hinge edge, or any corner joint by non-hinge edges | |
| Lateral Linear Dimension (Length along the edge, radius, etc.) | 1 mm or less, 2.5 mm or less, 5 mm or less, 10 mm or less, 15 mm or less, 20 mm or less, 25 mm or less, 30 mm or less, 40 mm or less, 50 mm or less, or in a range between any two of these values | In the range of 5 mm to 15 mm or about 10 mm |
| Area | 1 mm2 (square millimeter) or less, 10 mm2 or less, 25 mm2 or less, 50 mm2 or less, 75 mm2 or less or in a range between any two of these values. | In the range of 10 to 150 mm2; or about 50 mm2 |

| Trench: | | |
|---|---|---|
| Parameters | Embodiments | Preferred Embodiments |
| Number | 1, 2, 3, 4, 5, or more | 1 or 2 |
| Shape | Closed (round, ellipse, rectangle, triangle, polygon,ring-shaped, or any superposition or portion of these shapes) or open-ended (straight line, curved line, arc, branched tree, or any other shape with open endings); | |
| Length | 0.001 mm or less, 0.005 mm or less, 0.01 mm or less, 0.05 mm or less, 0.1 mm or less, 0.5 mm or less, 1 mm or less, 2 mm or less, 5 mm or less, 10 mm or less, 20 mm or less, 50 mm or less, 100 mm or less, or in a range between any two of these values | |
| Cross-sectional Area | 0.001 mm2 or less, 0.005 mm2 or less, 0.01 mm2 or less, 0.05 mm2 or less, 0.1 mm2 or less, 0.5 mm2 or less, 1 mm2 or less, 2 mm2 or less, 5 mm2 or less, 10 mm2 or less, 20 mm2 or less, or in a range between any two of these values. | |
| Volume | 0.1 uL or less, 0.5 uL or more, 1 uL or more, 2 uL or more, 5 uL or more, 10 uL or more, 30 uL or more, 50 uL or more, 100 uL or more, 500 uL or more, 1 mL or more, or in a range between any two of these values | In the range of 1 uL to 20 uL; or About 5 uL |

| Receptacle Slot | | |
|---|---|---|
| Parameters | Embodiments | Preferred Embodiments |
| Shape of receiving area | round, ellipse, rectangle, triangle, polygon, ring-shaped, or any superposition of these shapes; | |
| Difference between sliding track gap size and card thickness | 100 nm, 500 nm, 1 um, 2 um, 5 um, 10 um, 50 um, 100 um, 300 um, 500 um, 1 mm, 2 mm, 5 mm, 1 cm, or in a range between any two of the values. | In the range of 50 to 300 um; or about 75 um |

Spacer Dimensions

The term "spacer filling factor" or "filling factor" refers to the ratio of the spacer contact area to the total plate area", wherein the spacer contact area refers, at a closed configuration, the contact area that the spacer's top surface contacts to the inner surface of a plate, and the total plate area refers the total area of the inner surface of the plate that the flat top of the spacers contact. Since there are two plates and each spacer has two contact surfaces each contacting one plate, the filling fact is the filling factor of the smallest.

For example, if the spacers are pillars with a flat top of a square shape (10 um×10 um), a nearly uniform cross-section and 2 um tall, and the spacers are periodic with a period of 100 um, then the filing factor of the spacer is 1%. If in the above example, the foot of the pillar spacer is a square shape of 15 um×15 um, then the filling factor is still 1% by the definition.

The method or device of any prior embodiment, wherein the spacers have pillar shape and nearly uniform cross-section.

The method or device of any prior embodiment, wherein the inter spacer distance (SD) is equal or less than about 120 um (micrometer).

The method or device of any prior embodiment, wherein the inter spacer distance (SD) is equal or less than about 100 um (micrometer).

The method or device of any prior embodiment, wherein the fourth power of the inter-spacer-distance (ISD) divided by the thickness (h) and the Young's modulus (E) of the flexible plate (ISD$^4$/(hE)) is 5×10$^6$ um$^3$/GPa or less.

The method or device of any prior embodiment, wherein the fourth power of the inter-spacer-distance (ISD) divided by the thickness (h) and the Young's modulus (E) of the flexible plate (ISD$^4$/(hE)) is 5×10$^5$ um$^3$/GPa or less.

The method or device of any prior embodiment, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one).

The method or device of any prior embodiment, wherein the spacers have pillar shape, a substantially flat top surface, a predetermined substantially uniform height, and a predetermined constant inter-spacer distance that is at least about 2 times larger than the size of the analyte, wherein the Young's modulus of the spacers times the filling factor of the spacers is equal or larger than 2 MPa, wherein the filling factor is the ratio of the spacer contact area to the total plate area, and wherein, for each spacer, the ratio of the lateral dimension of the spacer to its height is at least 1 (one), wherein the fourth power of the inter-spacer-distance (ISD) divided by the thickness (h) and the Young's modulus (E) of the flexible plate (ISD$^4$/(hE)) is 5×10$^6$ um$^3$/GPa or less.

The device of any prior device embodiment, wherein the ratio of the inter-spacing distance of the spacers to the average width of the spacer is 2 or larger, and the filling factor of the spacers multiplied by the Young's modulus of the spacers is 2 MPa or larger.

The method or device of any prior embodiment, wherein the spacers have a shape of pillars and a ratio of the width to the height of the pillar is equal or larger than one. The method or device of any prior embodiment, wherein the spacers have a shape of pillar, and the pillar has substantially uniform cross-section.

Dimensions of Sample Compressed into a Layer

Further, in addition to the embodiments described above with respect to the sample compressed into a layer of substantially uniform thickness (e.g., layer 112B, 614, 708, or liquid film 814), the layer of uniform thickness may have the following dimensions, according to some embodiments:

The device of any prior device embodiment, wherein the layer of uniform thickness sample is uniform over a lateral area that is at least 1 mm2.

The device of any prior device embodiment, wherein the layer of uniform thickness sample is uniform over a lateral area that is at least 3 mm2.

The device of any prior device embodiment, wherein the layer of uniform thickness sample is uniform over a lateral area that is at least 5 mm2.

The device of any prior device embodiment, wherein the layer of uniform thickness sample is uniform over a lateral area that is at least 10 mm2.

The device of any prior device embodiment, wherein the layer of uniform thickness sample is uniform over a lateral area that is at least 20 mm2.

The device of any prior device embodiment, wherein the layer of uniform thickness sample is uniform over a lateral area that is in a range of 20 mm2 to 100 mm2.

The device of any prior device embodiment, wherein the layer of uniform thickness sample has a thickness uniformity of up to +/−5% or better.

The device of any prior device embodiment, wherein the layer of uniform thickness sample has a thickness uniformity of up to +/−10% or better.

The device of any prior device embodiment, wherein the layer of uniform thickness sample has a thickness uniformity of up to +/−20% or better.

The device of any prior device embodiment, wherein the layer of uniform thickness sample has a thickness uniformity of up to +/−30% or better.

Detection Methods

The devices, systems, and methods herein disclosed can include or be used in various types of detection methods. The detection methods are herein disclosed, or listed, described, and summarized in PCT Application (designating U.S.) Nos. PCT/US2016/046437 and PCT/US2016/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein by reference in their entireties for all purposes.

Labels, Capture Agent and Detection Agent

The devices, systems, and methods herein disclosed can employ various types of labels, capture agents, and detection agents that are used for analytes detection. The labels are herein disclosed, or listed, described, and summarized in PCT Application (designating U.S.) Nos. PCT/US2016/046437 and PCT/US2016/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein by reference in their entireties for all purposes.

Analytes

The devices, systems, and methods herein disclosed can be applied to manipulation and detection of various types of analytes (including biomarkers). The analytes are herein disclosed, or listed, described, and summarized in PCT Application (designating U.S.) Nos. PCT/US2016/046437 and PCT/US2016/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein by reference in their entireties for all purposes. For example, analytes can include molecules (e.g., a protein, peptides, DNA, RNA, nucleic acid, or other molecule), cells, tissues, viruses, and nanoparticles with different shapes, according to some embodiments. In some embodiments, the analytes can include white blood cells, red blood cells, or platelets. In some embodiments, the analytes can be proteins, peptides, nucleic acids, synthetic compounds, or inorganic compounds.

Sample

As described in the disclosure herein, the term "sample" can refer to samples obtained in the fields of biology (e.g., human biology), veterinary, agriculture, foods, environments, or drug testing. The sample can be freshly obtained, or stored or treated in any desired or convenient way, for example by dilution or adding buffers, or other solutions or solvents. Cellular structures can exist in the sample, such as human cells, animal cells, plant cells, bacteria cells, fungus cells, and virus particle.

In some embodiments, the sample is a biological sample from a human that is selected from hair, finger nail, ear wax, breath, connective tissue, muscle tissue, nervous tissue, epithelial tissue, cartilage, cancerous sample, or bone. In some embodiments, the sample may include cells, tissues, bodily fluids, or stool. In some embodiments, the sample refer to a biological sample that includes but not limited to human bodily fluids, such as whole blood, plasma, serum, urine, saliva, and sweat, and cell cultures (mammalian, plant, bacteria, or fungi). In some embodiments, the sample is a biological sample selected from amniotic fluid, aqueous humour, vitreous humour, blood (e.g., whole blood, fractionated blood, plasma or serum), breast milk, cerebrospinal fluid (CSF), cerumen (earwax), chyle, chime, endolymph, perilymph, feces, breath, gastric acid, gastric juice, lymph, mucus (including nasal drainage and phlegm), pericardial fluid, peritoneal fluid, pleural fluid, pus, rheum, saliva, exhaled breath condensates, sebum, semen, sputum, sweat, synovial fluid, tears, vomit, and urine.

In some embodiments, the samples relates to the detection, purification and quantification of chemical compounds or biomolecules that correlates with the stage of certain diseases.

In some embodiments, the samples is related to infectious and parasitic disease, injuries, cardiovascular disease, cancer, mental disorders, neuropsychiatric disorders, pulmonary diseases, renal diseases, and other and organic diseases.

In some embodiments, the samples is related to the detection, purification and quantification of microorganism.

In some embodiments, the samples is related to virus, fungus and bacteria from environment, e.g., water, soil, or biological samples.

In some embodiments, the samples is related to the detection, quantification of chemical compounds or biological samples that pose hazard to food safety or national security, e.g. toxic waste, anthrax.

In some embodiments, the samples is related to quantification of vital parameters in medical or physiological monitor.

In some embodiments, the samples is related to glucose, blood, oxygen level, total blood count.

In some embodiments, the samples is related to the detection and quantification of specific DNA or RNA from biosamples.

In some embodiments, the samples is related to the sequencing and comparing of genetic sequences in DNA in the chromosomes and mitochondria for genome analysis.

In some embodiments, the samples is related to detect reaction products, e.g., during synthesis or purification of pharmaceuticals.

Nucleic Acid

As described in the disclosure herein, the term "nucleic acid" can refer to any DNA or RNA molecule, or a DNA/RNA hybrid, or mixtures of DNA and/or RNA. The term "nucleic acid" therefore is intended to include but is not limited to genomic or chromosomal DNA, plasmid DNA, amplified DNA, cDNA, total RNA, mRNA and small RNA. The term "nucleic acid" is also intended to include natural DNA and/or RNA molecule, or synthetic DNA and/or RNA molecule. In some embodiments, cell-free nucleic acids are present in the sample, as used herein "cell-free" indicates nucleic acids are not contained in any cellular structures. In some other embodiments, nucleic acids are contained within cellular structures, which include but not limited to human cells, animal cells, plant cells, bacterial cells, fungi cells, and/or viral particles. In some embodiments, nucleic acids can be in a form of cell-free nucleic acids, within cellular structures, or a combination thereof. In some further embodiments, nucleic acids are purified before being introduced onto the inner surface of the first plate or the second plate. In yet further embodiments, nucleic acids can be within a complex associated with other molecules, such as proteins and lipids.

Applications (Field and Samples)

The devices, systems, and methods herein disclosed can be used for various applications (fields and samples). The applications are herein disclosed, or listed, described, and summarized in PCT Application (designating U.S.) Nos. PCT/US2016/046437 and PCT/US2016/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein by reference in their entireties for all purposes.

In some embodiments, the devices, apparatus, systems, and methods herein disclosed are used in a variety of different application in various field, wherein determination of the presence or absence, quantification, and/or amplification of one or more analytes in a sample are desired. For example, in certain embodiments the subject devices, apparatus, systems, and methods are used in the detection of proteins, peptides, nucleic acids, synthetic compounds, inorganic compounds, organic compounds, bacteria, virus, cells, tissues, nanoparticles, and other molecules, compounds, mixtures and substances thereof. The various fields in which the subject devices, apparatus, systems, and methods can be used include, but are not limited to: diagnostics, management, and/or prevention of human diseases and conditions, diagnostics, management, and/or prevention of veterinary diseases and conditions, diagnostics, management, and/or prevention of plant diseases and conditions, agricultural uses, veterinary uses, food testing, environments testing and decontamination, drug testing and prevention, and others.

The applications of the present invention include, but are not limited to: (a) the detection, purification, quantification, and/or amplification of chemical compounds or biomolecules that correlates with certain diseases, or certain stages of the diseases, e.g., infectious and parasitic disease, injuries, cardiovascular disease, cancer, mental disorders, neuropsychiatric disorders and organic diseases, e.g., pulmonary diseases, renal diseases, (b) the detection, purification, quantification, and/or amplification of cells and/or microorganism, e.g., virus, fungus and bacteria from the environment, e.g., water, soil, or biological samples, e.g., tissues, bodily fluids, (c) the detection, quantification of chemical compounds or biological samples that pose hazard to food safety, human health, or national security, e.g. toxic waste, anthrax, (d) the detection and quantification of vital parameters in medical or physiological monitor, e.g., glucose, blood oxygen level, total blood count, (e) the detection and quantification of specific DNA or RNA from biological samples, e.g., cells, viruses, bodily fluids, (f) the sequencing and comparing of genetic sequences in DNA in the chromosomes and mitochondria for genome analysis or (g) the detection and quantification of reaction products, e.g., during synthesis or purification of pharmaceuticals.

In some embodiments, the subject devices, apparatus, systems, and methods are used in the detection of nucleic acids, proteins, or other molecules or compounds in a sample. In certain embodiments, the devices, apparatus, systems, and methods are used in the rapid, clinical detection and/or quantification of one or more, two or more, or three or more disease biomarkers in a biological sample, e.g., as being employed in the diagnosis, prevention, and/or management of a disease condition in a subject. In certain embodiments, the devices, apparatus, systems, and methods are used in the detection and/or quantification of one or more, two or more, or three or more environmental markers in an environmental sample, e.g. sample obtained from a river, ocean, lake, rain, snow, sewage, sewage processing runoff, agricultural runoff, industrial runoff, tap water or drinking water. In certain embodiments, the devices, apparatus, systems, and methods are used in the detection and/or quantification of one or more, two or more, or three or more foodstuff marks from a food sample obtained from tap water, drinking water, prepared food, processed food or raw food.

In some embodiments, the subject device is part of a microfluidic device. In some embodiments, the subject devices, apparatus, systems, and methods are used to detect a fluorescence or luminescence signal. In some embodiments, the subject devices, apparatus, systems, and methods include, or are used together with, a communication device, such as but not limited to: mobile phones, tablet computers and laptop computers. In some embodiments, the subject devices, apparatus, systems, and methods include, or are used together with, an identifier, such as but not limited to an optical barcode, a radio frequency ID tag, or combinations thereof.

In some embodiments, the sample is a diagnostic sample obtained from a subject, the analyte is a biomarker, and the measured amount of the analyte in the sample is diagnostic of a disease or a condition. In some embodiments, the subject devices, systems and methods further include receiving or providing to the subject a report that indicates the measured amount of the biomarker and a range of measured values for the biomarker in an individual free of or at low risk of having the disease or condition, wherein the measured amount of the biomarker relative to the range of measured values is diagnostic of a disease or condition.

In some embodiments, the sample is an environmental sample, and wherein the analyte is an environmental marker. In some embodiments, the subject devices, systems and methods includes receiving or providing a report that indicates the safety or harmfulness for a subject to be exposed to the environment from which the sample was obtained. In some embodiments, the subject devices, systems and methods include sending data containing the measured amount of the environmental marker to a remote location and receiving a report that indicates the safety or harmfulness for a subject to be exposed to the environment from which the sample was obtained.

In some embodiments, the sample is a foodstuff sample, wherein the analyte is a foodstuff marker, and wherein the amount of the foodstuff marker in the sample correlate with safety of the foodstuff for consumption. In some embodiments, the subject devices, systems and methods include receiving or providing a report that indicates the safety or harmfulness for a subject to consume the foodstuff from which the sample is obtained. In some embodiments, the subject devices, systems and methods include sending data containing the measured amount of the foodstuff marker to a remote location and receiving a report that indicates the safety or harmfulness for a subject to consume the foodstuff from which the sample is obtained.

The present disclosure find use in a variety of different applications in various fields, where determination of the presence or absence, and/or quantification of one or more analytes in a sample are desired. For example, the present inventions finds use in the detection of atoms, molecules, proteins, peptides, nucleic acids, synthetic compounds, inorganic compounds, organic compounds, bacteria, virus, cells, tissues, nanoparticles, and the like. The sample can be a sample in various fields, that include, but not limited to, human, veterinary, agriculture, foods, environments, health, wellness, beauty, and others.

Cloud

The devices, systems, and methods herein disclosed can employ cloud technology for data transfer, storage, and/or analysis. The related cloud technologies are herein disclosed, or listed, described, and summarized in PCT Application (designating U.S.) Nos. PCT/US2016/046437 and PCT/US2016/051775, which were respectively filed on Aug. 10, 2016 and Sep. 14, 2016, U.S. Provisional Application No. 62/456,065, which was filed on Feb. 7, 2017, U.S. Provisional Application No. 62/456,287, which was filed on Feb. 8, 2017, and U.S. Provisional Application No. 62/456,504, which was filed on Feb. 8, 2017, all of which applications are incorporated herein by reference in their entireties for all purposes.

Additional Descriptions

The foregoing description sets forth exemplary methods, parameters and the like. It should be recognized, however, that such description is not intended as a limitation on the scope of the present disclosure but is instead provided as a description of exemplary embodiments. The illustrative embodiments described above are not intended to be exhaustive or to limit the disclosure to the precise forms disclosed. Many modifications and variations are possible in view of the above teachings. The embodiments were chosen and described to best explain the principles of the disclosed techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. In the foregoing description of the disclosure and embodiments, reference is made to the accompanying drawings, in which are shown, by way of illustration, specific embodiments that can be practiced. It is to be understood that other embodiments and examples can be practiced, and changes can be made without departing from the scope of the present disclosure.

Although the foregoing description uses terms first, second, etc. to describe various elements, these elements should not be limited by the terms. These terms are only used to distinguish one element from another.

It must be noted that as used herein and in the appended embodiments, the singular forms "a", "an", and "the" include plural referents unless the context clearly dictates otherwise, e.g., when the word "single" is used. For example, reference to "an analyte" includes a single analyte and multiple analytes, reference to "a capture agent" includes a single capture agent and multiple capture agents, reference to "a detection agent" includes a single detection agent and multiple detection agents, and reference to "an agent" includes a single agent and multiple agents.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function. Similarly, subject matter that is recited as being configured to perform a particular function may additionally or alternatively be described as being operative to perform that function.

As used herein, the phrase, "for example," the phrase, "as an example," and/or simply the terms "example" and "exemplary" when used with reference to one or more components, features, details, structures, embodiments, and/or methods according to the present disclosure, are intended to convey that the described component, feature, detail, structure, embodiment, and/or method is an illustrative, non-exclusive example of components, features, details, structures, embodiments, and/or methods according to the present disclosure. Thus, the described component, feature, detail, structure, embodiment, and/or method is not intended to be limiting, required, or exclusive/exhaustive; and other components, features, details, structures, embodiments, and/or methods, including structurally and/or functionally similar and/or equivalent components, features, details, structures, embodiments, and/or methods, are also within the scope of the present disclosure.

The term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entities specifically identified.

Reference to "about" a value or parameter herein includes (and describes) variations that are directed to that value or parameter per se. For example, description referring to "about X" includes description of "X". In addition, reference to phrases "less than", "greater than", "at most", "at least", "less than or equal to", "greater than or equal to", or other similar phrases followed by a string of values or parameters is meant to apply the phrase to each value or parameter in the string of values or parameters. For example, a statement that the protein has at least about 2 amino acids, about 10 amino acids, or about 50 amino acids means that the protein has at least about 2 amino acids, at least about 10 amino acids, or at least about 50 amino acids.

This application discloses several numerical ranges in the text and figures. The numerical ranges disclosed inherently support any range or value within the disclosed numerical ranges, including the endpoints, even though a precise range limitation is not stated verbatim in the specification because this disclosure can be practiced throughout the disclosed numerical ranges.

Reference to "substantially" herein can mean that the variation is less than about 30%, about 20%, about 10%, about 5%, about 1%, about 0.5%, about 0.25%, about 0.1%, about 0.05%, about 0.01%, or about 0.005%.

Where numerical ranges are mentioned herein, this disclosure includes embodiments in which the endpoints are included, embodiments in which both endpoints are excluded, and embodiments in which one endpoint is included and the other is excluded. It should be assumed that both endpoints are included unless indicated otherwise. Furthermore, unless otherwise indicated or otherwise evident from the context and understanding of one of ordinary skill in the art.

In the event that any patents, patent applications, or other references are incorporated by reference herein and (1) define a term in a manner that is inconsistent with and/or (2) are otherwise inconsistent with, either the non-incorporated portion of the present disclosure or any of the other incorporated references, the non-incorporated portion of the present disclosure shall control, and the term or incorporated disclosure therein shall only control with respect to the reference in which the term is defined and/or the incorporated disclosure was present originally.

The invention claimed is:

1. A device, comprising:
   a first plate and a second plate, wherein:
      the first and second plates are movable relative to each other into an open configuration and a closed configuration,
      each of the first and second plates respectively comprise an inner surface that has a sample contact area for contacting a fluid sample, and
      at least one of the plates is flexible;
   spacers that are fixed on at least one of the first and second plates and have a predetermined substantially uniform height; and
   a first and a second electrode fixed to at least one of the first and second plates;
   wherein in the open configuration, the first and second plates are partially or entirely separated apart to enable the fluid sample to be deposited on at least one of the first and second plates, wherein a spacing between the first and second plates is not regulated by the spacers; and
   wherein in the closed configuration, which is configured after the fluid sample is deposited on at least one of the first and second plates in the open configuration, at least part of the fluid sample is compressed by the first and second plates into a layer of substantially uniform thickness and is substantially stagnant relative to the first and second plates, wherein the layer is confined by the inner surfaces of the first and second plates and is regulated by the spacers, and wherein the at least part of the sample is between the first plate and the second plate and the average spacing between the inner surfaces of the first and second plates is less than 200 μm.

2. The device of claim 1, wherein the first and second electrodes are made from a metal including gold, copper, silver, aluminum, or a mixture thereof, or an alloy thereof.

3. The device of claim 1, wherein the first and second electrodes are made from conductive metallic oxide or metallic compound that is selected from the group consisting of: indium tin oxide (ITO), zinc oxide (ZnO), titanium oxide (TiOx), molybdenum dioxide ($MoO_2$), lithium fluoride (LiF), and a combination thereof.

4. The device of claim 1, wherein the first and second electrodes are made from conductive small molecule and conductive polymer that is selected from poly(3,4-ethylenedioxythiophene) poly(styrenesulfonate) (PECOT:PSS), fullerene derivatives (as C60), aluminum tris (8-hydroxyquinoline)(Alq3), and a combination thereof.

5. The device of claim 1, wherein an inter-spacer distance for the spacers is between 7 μm and 200 μm.

6. The device of claim 1, wherein an inter-spacer distance for the spacers is between 120 μm and 200 μm.

7. The device of claim 1, wherein the width of any of the electrodes is at least 2 times, 5 times, 10 times, 50 times, 100 times, 500 times, or 1000 times larger than the height of the electrode.

8. The device of claim 1, wherein the width of any of the electrodes is at least 2 times, 5 times, 10 times, 50 times, 100 times, 500 times, or 1000 times larger than the gap between any two adjacent electrodes.

9. The device of claim 1, wherein the height of any of the electrodes is less than 1 nm, 10 nm, 50 nm, 100 nm, 500 nm, 1 μm, 10 μm, 50 μm, 100 μm, 500 μm, 1 mm, 5 mm, or 10 mm.

10. The device of claim 1, wherein the width of any of the electrodes is less than 1 nm, 10 nm, 50 nm, 100 nm, 500 nm, 1 μm, 10 μm, 50 μm, 100 μm, 500 μm, 1 mm, 5 mm, 10 mm, 50 mm, or 100 mm.

11. The device of claim 1, wherein the gap between any two adjacent electrodes is less than 1 nm, 10 nm, 50 nm, 100 nm, 500 nm, 1 μm, 10 μm, 50 μm, 100 μm, 500 μm, 1 mm, 5 mm, 10 mm, 50 mm, or 100 mm.

12. The device of claim 1, wherein the first electrode is fixed on the inner surface of the first plate and the second electrodes is fixed on the inner surface of the second plate.

13. The device of claim 1, wherein the first and second electrodes are both fixed on only one of the first and second plates.

14. The device of claim 1, wherein the first electrode is fixed on the outer surface of the first plate and the second electrodes is fixed on the outer surface of the second plate.

15. The device of claim 1, wherein the first electrode is fixed on the outer surface of the first plate and the second electrodes is fixed on the inner surface of the second plate.

16. The device of claim 1, comprising:
   a power source configured to induce a voltage between the first and second plates in the closed configuration.

17. The device of claim 16, wherein the voltage is less than 0.2V, 0.2V, 0.5V, 1V, 5V, 10V; 50V, 100V, 110V, 150V, 200V, 220V, 500V, or 1000V.

18. The device of claim 16, wherein the power source comprises an AC source having a frequency that is less than 10 Hz, 100 Hz, 1000 Hz, 10 kHz, 100 kHz, 1 MHz, or 1 GHz.

19. The device of claim 16, wherein the first and second electrodes are in ionic communication with the fluid sample in the layer after the voltage is induced.

20. The device of claim 1, wherein the first and second electrodes are configured to detect an electric property of the fluid sample in the layer.

21. The device of claim 20, wherein the electric properties include one or more of conductance, current, potential, impedance, capacitance, or a permittivity.

22. The device of claim 1, comprising:
a measuring device connected to at least one of the first and second electrodes to measure the electric property.

23. The device of claim 22, wherein the measuring device is configured to measure the electric property after the fluid sample is deposited at a time of 10 s, 30 s, 60 s, 2 min, 3 min, 5 min, 8 min, 10 min, 15 min, 20 min, or 30 min.

24. The device of claim 1, comprising:
a barrier membrane that covers the second electrode, wherein the barrier membrane is configured to allow one or more selected analytes in the fluid sample to pass through the barrier membrane and block other analytes.

25. The device of claim 24, wherein the barrier membrane comprises an insoluble, infusible synthetic organic polymer matrix which is bound with a chemical that selectively allow the one or more selected analytes in the fluid sample to pass through the barrier membrane.

26. The device of claim 24, wherein the barrier membrane comprises an organic polymer matrix selected from the group consisting of poly(vinyl chloride) (PVC), polyvinylpyrrolidone, polydimethylsiloxane, and perfluoropolyether.

27. The device of claim 25, wherein the chemical is selected from the group consisting of: ETH 157 carrier, ETh 227 carrier, ETH 2120 carrier, a bis(12-crown-4) compound, hemispherand, valinomycin, BBPA, KTpClPB, and '70 o-nitrophenyl octyl ether.

28. The device of claim 24, wherein the barrier membrane is coated on top of the second electrode.

29. The device of claim 1, wherein the fluid sample comprises whole blood or serum blood, comprising:
a measuring device connected to at least one of the first and second electrodes to measure a permittivity of the fluid sample at the layer; and
a calculation unit configured to calculate a prothrombin time (PT) or an activated partial thromboplastin time (aPTT) of the fluid sample based on the measured permittivity.

30. The device of claim 1, wherein the height of the spacer is less than 1 μm, 10 μm, 100 μm, or 1 cm.

31. The device of claim 1, wherein the first or second plate comprises a round corner having a diameter less than 100 μm, 200 μm, 500 μm, 1 mm, 2 mm, 5 mm, 10 mm, or 50 mm.

32. The device of claim 1, wherein the first or second plate comprises a round corner having a diameter in a range between any two values selected from a group consisting of 100 μm, 200 μm, 500 μm, 1 mm, 2 mm, 5 mm, 10 mm, and 50 mm.

33. The device of claim 1, wherein the first or second plate comprises an average thickness in a range from 0.5 mm to 1.5 mm or in a range from 0.15 mm to 0.2 mm.

34. The device of claim 1, wherein the first or second plate comprises an average thickness of about 1 mm or about 0.175 mm.

35. The device of claim 1, wherein the first or second plate comprises a lateral area in a range from 500 mm$^2$ to 1000 mm$^2$.

36. The device of claim 1, wherein the first or second plate comprises a lateral area of about 750 mm$^2$.

37. The device of claim 1, wherein the first or second plate comprises a lateral linear dimension in a range from 20 mm to 30 mm.

38. The device of claim 1, wherein the first or second plate comprises a lateral linear dimension of about 24 mm.

39. The device of claim 1, wherein the first or second plate comprises a recess width in a range from 1 mm to 10 mm.

40. The device of claim 1, wherein the layer of substantially uniform thickness comprises an average thickness between 0.01 μm and 200 μm.

41. The device of claim 1, wherein the fluid sample comprises amniotic fluid, aqueous humour, vitreous humour, breast milk, cerebrospinal fluid (CSF), cerumen (earwax), chyle, chime, endolymph, perilymph, feces, gastric acid, gastric juice, lymph, mucus, nasal drainage, phlegm), pericardial fluid, peritoneal fluid, pleural fluid, pus, rheum, sebum, semen, sputum, sweat, synovial fluid, tears, vomit, urine or exhaled condensate.

42. A method of analyzing electric properties of a fluid sample, comprising:
obtaining the device of claim 1;
depositing the fluid sample on at least one of the first and second plates in the open configuration;
pressing the first and second plates together into the closed configuration to compress at least part of the fluid sample into a layer of substantially uniform thickness; and
using the first and second electrodes to measure an electric property of the fluid sample at the layer of substantially uniform thickness.

43. The method of claim 42, wherein the electric property comprises conductance, current, potential, capacitance, or permittivity.

44. The method of claim 42, wherein the electric property is measured for a predetermined number of times at predetermined time periods after pressing the first and second plates together.

45. The method of claim 42, wherein the fluid sample comprises blood serum, whole blood, blood with added $Ca^{2+}$, or blood with added citrate acid or salt.

46. The method of claim 42, wherein the electric property comprises permittivity of the fluid sample, comprising:
assessing coagulation of the fluid sample based on the permittivity.

47. The method of claim 46, wherein the assessing the coagulation comprises:
assessing prothrombin time (PT) or activated partial thromboplastin time (aPTT) of the fluid sample.

48. The device of claim 1,
wherein the sample contact area is configured to be capable of being charged, by an electric field, to an electrical polarity that is opposite to that of the charged bio/chemical material.

49. The device of claim 48, wherein the electric field is provided by two or more electrodes coupled to the first or second plate.

50. The device of claim 48, wherein the two or more electrodes are positioned outside of the first and second plates when the first and second plates are in the closed configuration.

51. The device of claim 48, wherein the two or more electrodes are positioned inside of the first and second plates when the first and second plates are in the closed configuration.

52. The device of claim 48, wherein at least one of the spacers comprise one of the two or more electrodes.

53. The device of claim 48, wherein the two or more electrodes are on the inner surfaces of the first or second plates.

54. The device of claim 48, wherein the two or more electrodes are on the outer surfaces of the first or second plates.

55. The device of claim 48, wherein an inter-spacer distance for the spacers is between 7 μm and 200 μm.

56. The device of claim 48, wherein an inter-spacer distance for the spacers is between 120 μm and 200 μm.

57. The device of claim 48, wherein the width of any of the electrodes is at least 2 times, 5 times, 10 times, 50 times, 100 times, 500 time, or 1000 times larger than the height of the electrode.

58. The device of claim 48, wherein the width of any of the electrodes is at least 2 times, 5 times, 10 times, 50 times, 100 times, 500 times, or 1000 times larger than the gap between any two adjacent electrodes.

59. The device of claim 48, wherein the height of any of the electrodes is less than 1 nm, 10 nm, 50 nm, 100 nm, 500 nm, 1 μm, 10 μm, 50 μm, 100 μm, 500 μm, 1 mm, 5 mm, or 10 mm.

60. The device of claim 48, wherein the width of any of the electrodes is less than 1 nm, 10 nm, 50 nm, 100 nm, 500 nm, 1 μm, 10 μm, 50 μm, 100 μm, 500 μm, 1 mm, 5 mm, 10 mm, 50 mm, or 100 mm.

61. The device of claim 48, wherein the gap between any two adjacent electrodes is less than 1 nm, 10 nm, 50 nm, 100 nm, 500 nm, 1 μm, 10 μm, 50 μm, 100 μm, 500 μm, 1 mm, 5 mm, 10 mm, 50 mm, or 100 mm.

62. The device of claim 48, wherein the height of the spacer is less than 1 μm, 10 μm, 100 μm, or 1 cm.

63. The device of claim 48, wherein the fluid sample comprises blood serum or whole blood.

64. The device of claim 48, wherein the first or second plate comprises a round corner having a diameter less than 100 μm, 200 μm, 500 μm, 1 mm, 2 mm, 5 mm, 10 mm, or 50 mm.

65. The device of claim 48, wherein the first or second plate comprises a round corner having a diameter in a range between any two values selected from a group consisting of 100 μm, 200 μm, 500 μm, 1 mm, 2 mm, 5 mm, 10 mm, and 50 mm.

66. The device of claim 48, wherein the first or second plate comprises an average thickness in a range from 0.5 mm to 1.5 mm or in a range from 0.15 mm to 0.2 mm.

67. The device of claim 48, wherein the first or second plate comprises an average thickness of about 1 mm or about 0.175 mm.

68. The device of claim 48, wherein the first or second plate comprises a lateral area in a range from 500 mm² to 1000 mm².

69. The device of claim 48, wherein the first or second plate comprises a lateral area of about 750 mm².

70. The device of claim 48, wherein the first or second plate comprises a lateral linear dimension in a range from 20 mm to 30 mm.

71. The device of claim 48, wherein the first or second plate comprises a lateral linear dimension of about 24 mm.

72. The device of claim 48, wherein the first or second plate comprises a recess width in a range from 1 mm to 10 mm.

73. The device of claim 48, wherein the layer of substantially uniform thickness comprises an average thickness between 0.01 μm and 200 μm.

74. A method for extracting charged bio/chemical materials from a fluid sample, comprising:
obtaining the device of claim 49;
depositing, at the open configuration, a fluid sample comprising a bio/chemical material that has a first charge polarity;
pressing the first and second plates together into the closed configuration to compress at least part of the fluid sample into a layer of substantially uniform thickness; and
applying an electric field to charge a sample contact surface on the inner surface of the second plate to second electrical polarity that is opposite of the first electrical polarity, wherein the bio/chemical material is captured at the sample contact area.

75. The method of claim 74, comprising:
opening the first plate and the second plate in to the open configuration; and
washing the sample contact area of the second plate to remove contaminates from the bio/chemical material captured at the sample contact area.

76. The method of claim 75, wherein washing the sample contact area comprises using a sponge including a washing reagent to remove the contaminates.

77. The method of claim 74, comprising:
washing the inner surface of the second plate with a sponge comprising flexible porous material having pores that are deformable and have size and surface properties configured to absorb a liquid into the material or release a liquid out of the material, when the shape of the pores are changed.

78. The method of claim 74, comprising:
pressing the sponge to release washing reagent contained in the sponge with a force and removing the force to allow the sponge to re-absorb the washing reagent.

79. The method of claim 74, comprising:
adding a detection reagent to the captured bio/chemical material, wherein the detection reagent is configured to bind to an analyte in the bio/chemical material to produce a detectable signal.

80. The method of claim 74, wherein the bio/chemical material comprises nucleic acid having a negative polarity charge.

81. The method of claim 74, wherein the spacers have a substantially uniform height, comprising:
allowing the first and second plates to lyse the bio/chemical material in the bio/chemical sample when the first and second plates are in the closed configuration.

82. The method of claim 74, wherein the bio/chemical material comprises blood cells.

83. The method of claim 74, wherein the bio/chemical material comprises nucleic acids, comprising:
adding a polymerase chain reaction (PCR) medium to the captured bio/chemical material; and
conducting a PCR reaction.

84. The method of claim 83, comprising:
conducting the PCR reaction by changing a temperature of the first or second plate by applying electromagnetic signals to the first or second plates.

85. The method of claim 74, comprising:
changing a temperature of the first or second plate by emitting light on the first or second plate.

86. The method of claim 83, comprising:
conducting the PCR reaction by changing a temperature of the first or second plate by electric signals from the first or second electrode.

87. The method of claim 74, wherein the sample contact area comprises a reagent storage area that comprises a reagent that, upon coming in contact to the fluid sample, is capable of diffusing in the fluid sample.

88. The method of claim 87, wherein the reagent comprises a lysing reagent or a detection agent.

89. The device of claim 1, wherein
the second plate comprises, on a second inner surface, a well configured to host a sensing chip inside the well, wherein the sensing chip has a sensing surface, wherein the sensing surface of the sensing chip is in the same direction as the second inner surface of the second plate,
the spacers are fixed on at least one of the first inner surface of the first plate, the second inner surface of the second plate, or the sensing surface of the sensing chip;
wherein the substantially uniform thickness of the layer is confined by the sample contact area of the first plate and the sensing surface of the sensing chip, and is regulated by the first plate, the sensing chip, and the spacers.

90. The device of claim 89, further comprising a device adaptor
for analyzing a fluid sample using the sensing chip, comprising:
a housing;
an attachment on the housing that allows the device adaptor to attach to a computing device with an imaging device;
a slot in the housing that allows the first and second plates in the closed configuration to slide into the slot and when the first and second plates are in the slot, the optical system is configured to have at least a part of the sample contact area be imaged by the imaging device.

91. The device of claim 89, wherein the fluid sample comprises blood serum or whole blood.

92. The device of claim 89, wherein the first or second plate comprises a round corner having a diameter less than 100 µm, 200 µm, 500 µm, 1 mm, 2 mm, 5 mm, 10 mm, or 50 mm.

93. The device of claim 89, wherein the first or second plate comprises a round corner having a diameter in a range between any two values selected from a group consisting of 100 µm, 200 µm, 500 µm, 1 mm, 2 mm, 5 mm, 10 mm, and 50 mm.

94. The device of claim 89, wherein the first or second plate comprises an average thickness in a range from 0.5 mm to 1.5 mm or in a range from 0.15 mm to 0.2 mm.

95. The device of claim 89, wherein the first or second plate comprises an average thickness of about 1 mm or about 0.175 mm.

96. The device of claim 89, wherein the first or second plate comprises a lateral area in a range from 500 mm$^2$ to 1000 mm$^2$.

97. The device of claim 89, wherein the first or second plate comprises a lateral area of about 750 mm$^2$.

98. The device of claim 89, wherein the first or second plate comprises a lateral linear dimension in a range from 20 mm to 30 mm.

99. The device of claim 89, wherein the first or second plate comprises a lateral linear dimension of about 24 mm.

100. The device of claim 89, wherein the first or second plate comprises a recess width in a range from 1 mm to 10 mm.

101. The device of claim 89, wherein the layer of substantially uniform thickness comprises an average thickness between 0.01 µm and 200 µm.

102. The device of claim 89, wherein the average thickness of the sensing chip is in a range of 50 nm, 100 nm, 200 nm, 500 nm, 1 µm, 2 µm, 5 µm, 10 µm, 20 µm, 30 µm, 50 µm, 70 µm, 100 µm, 120 µm, 150 µm, 200 µm, 300 µm, 400 µm, 500 µm, 1 mm, or 3 mm.

103. The device of claim 89, wherein the average thickness of the sensing chip is in a range of 500 nm-700 µm.

104. The device of claim 89, wherein the average thickness of the sensing chip is in a range of 1 µm-500 µm.

105. The device of claim 89, wherein a length or a width of the sensing chip is in a range between 50 nm-30 mm.

106. The device of claim 89, wherein a length or a width of the sensing chip is in a range between 1 µm and 10 mm or 1 µm and 8 mm.

107. The device of claim 89, wherein the sensing surface comprises a binding site to bind a target analyte in the fluid sample.

108. The device of claim 89, wherein the sensing surface comprises an amplification surface selected from the group consisting of local surface plasmonic structures, surface plasmonic surface, metallic surfaces, and a blend of metallic and dielectric layers or structures.

109. The device of claim 89, wherein a fourth power of an inter-spacer-distance (IDS) divided by the thickness (h) and the Young's modulus (E) of the flexible plate (ISD$^4$/(hE)) is less than or equal to 5×10$^6$ µm$^3$/GPa, 1×10$^6$ µm$^3$/GPa, or 5×10$^5$ µm$^3$/GPa.

110. The device of claim 89, wherein the Young's modulus of the spacers multiplied by the filling factor of the spacers is at least 2 MPa, and a fourth power of an inter-spacer-distance (IDS) divided by the thickness (h) and the Young's modulus (E) of the flexible plate (ISD$^4$/(hE)) is 1×10$^5$ µm$^3$/GPa or less.

111. The device of claim 89, wherein the Young's modulus of the spacers multiplied by the filling factor of the spacers is at least 2 MPa, and a fourth power of an inter-spacer-distance (IDS) divided by the thickness (h) and the Young's modulus (E) of the flexible plate (ISD$^4$/(hE)) is 1×10$^4$ µm$^3$/GPa.

112. The device of claim 89, wherein the fluid sample comprises a viscosity in the range of 0.1 to 4 (mPa s).

113. The device of claim 89, wherein the spacer height is in the range of 2 µm to 2.5 µm, 1.8 µm to 2.2 µm, or 2 µm to 3 µm.

114. The device of claim 89, wherein the spacer height is about 2 µm, 2.2 µm, 2.4 µm, 2.6 µm, 2.8 µm, 3 µm, 3.2 µm, 3.4 µm, or 3.6 µm.

115. The device of claim 89, wherein the sample contact area has an area of 5 mm$^2$ (millimeter square) to 150 mm$^2$.

116. The device of claim 89, wherein the sample contact area has an area of 5 mm$^2$ to 10 mm$^2$, 10 mm$^2$ to 20 mm$^2$, or 20 mm$^2$ to 40 mm$^2$.

117. The device of claim 89, wherein the sample contact area has an area of 40 mm$^2$ to 60 mm$^2$, 60 mm$^2$ to 80 mm$^2$, or 80 mm$^2$ to 150 mm$^2$.

118. The device of claim 89, wherein an inter-spacer distance is at least about 2 times larger than a size of a target analyte in the fluid sample, up to 200 µm.

119. The device of claim 89, wherein a ratio of an inter-spacer-distance to the spacer width is at least 1.5.

120. The device of claim 89, wherein a ratio of an inter-spacer-distance to the spacer width is at least 1.

121. The device of claim 89, wherein a ratio of the width to the height of the spacers is 1.5 or larger.

122. The device of claim 89, wherein a ratio of the width to the height of the spacer is 2 or larger.

123. The device of claim 89, wherein a ratio of the width to the height of the spacer is larger than 2, 3, 5, 10, 20, 30, or 50.

124. The device of claim 89, wherein the force that presses the two plates into the closed configuration is an imprecise pressing force.

125. The device of claim 89, wherein the spacers are configured, such that the filling factor is in the range of 1% to 5%.

126. The device of claim 89, wherein the spacers are configured, such that the filling factor is in the range of 5% to 10%.

127. The device of claim 89, wherein the spacers are configured, such that the filling factor is in the range of 10% to 20%.

128. The device of claim 89, wherein the spacers are configured, such that the filling factor is in the range of 20% to 30%.

129. The device of claim 89, wherein the spacers are configured, such that the filling factor is less than 5%, 10%, 20%, 30%, 40%, or 50%.

130. The device of claim 89, wherein the spacers are configured, such that the filling factor is greater than 50%, 60%, 70%, 80%.

131. The device of claim 89, wherein the spacers are configured, such that the filling factor multiplies the Young's modulus of the spacers is in the range of 2 MPa and 10 MPa.

132. The device of claim 89, wherein the spacers are configured, such that the filling factor multiplies the Young's modulus of the spacers is in the range of 10 MPa and 150 MPa.

133. A method for analyzing a fluid sample using a sensing device, comprising:
obtaining the device of claim 1; wherein:
the first and second plates are flexible;
the second plate comprises, on inner surface, a chip hosting well and a sensing chip inside the hosting well, wherein the sensing chip has sensing surface,
the second plate comprises, on inner surface including the sensing surface of the sensing chip;
one or both of the plates, the sensing surface of the sensing chip, or all of them comprise the spacers that are permanently fixed on its respective sample contact area;
depositing the fluidic sample on one or both of the plates, the sensing chip, or all of them when the plates are configured in the open configuration;
forcing the two plates into the closed configuration.

134. The method of claim 133, comprising:
inserting the first and second plates in the closed configuration into a slot in a device adaptor, wherein the device adaptor comprises: a housing; an attachment on the housing that allows the device adaptor to attach to a computing device with an imaging device; and the slot in the housing that allows the first and second plates in the closed configuration to slide into the slot.

135. The method of claim 134, wherein the device adaptor comprises an optical system, comprising: when the first and second plates are in the slot, configuring the optical system to enable at least a part of the sample contact area be imaged by the imaging device.

136. The method of claim 134, comprising:
assaying an analyte in the fluid sample deposited on the first or second plate to generate a result; and
communicating the result from the computing device to a server located remotely from the computing device.

137. The method of claim 133, wherein the analyte comprises a molecule (e.g., a protein, peptides, DNA, RNA, nucleic acid, or other molecule), cells, tissues, viruses, and nanoparticles with different shapes.

138. The method of claim 136, wherein the assaying comprises performing a white blood cells differential assay.

139. The method of claim 136, wherein the method comprises:
analyzing the results at the server to provide an analyzed result; and
wirelessly communicating the analyzed result from the server to the computing device.

140. The method of claim 134, wherein the computing device receives a prescription, diagnosis or a recommendation from a medical professional from the server.

* * * * *